United States Patent
Zeng et al.

(10) Patent No.: US 10,682,297 B2
(45) Date of Patent: Jun. 16, 2020

(54) LIPOSOMES, EMULSIONS, AND METHODS FOR CRYOTHERAPY

(71) Applicant: Zeltiq Aesthetics, Inc., Pleasanton, CA (US)

(72) Inventors: Like Zeng, Pleasanton, CA (US); Joel N. Jimenez Lozano, Dublin, CA (US); Leonard C. DeBenedictis, Dublin, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 335 days.

(21) Appl. No.: 15/498,867

(22) Filed: Apr. 27, 2017

(65) Prior Publication Data
US 2017/0326042 A1    Nov. 16, 2017

Related U.S. Application Data

(60) Provisional application No. 62/334,330, filed on May 10, 2016.

(51) Int. Cl.
*A61K 8/14* (2006.01)
*A61K 8/34* (2006.01)
(Continued)

(52) U.S. Cl.
CPC .............. *A61K 8/14* (2013.01); *A61F 7/0085* (2013.01); *A61K 8/345* (2013.01); *A61K 9/0014* (2013.01); *A61K 9/127* (2013.01); *A61P 17/10* (2018.01); *A61Q 19/00* (2013.01); *A61Q 19/06* (2013.01); *A61Q 19/08* (2013.01); *A61B 2090/0463* (2016.02); *A61F 2007/0052* (2013.01); *A61F 2007/0056* (2013.01); *A61F 2007/0076* (2013.01); *A61F 2007/0086* (2013.01);
(Continued)

(58) Field of Classification Search
None
See application file for complete search history.

(56) References Cited

U.S. PATENT DOCUMENTS

| 681,806 A | 9/1901 | Mignault et al. |
| 889,810 A | 6/1908 | Robinson et al. |

(Continued)

FOREIGN PATENT DOCUMENTS

| AU | 2011253768 A1 | 6/2012 |
| CA | 2441489 A1 | 3/2005 |

(Continued)

OTHER PUBLICATIONS

"ThermaCool Monopolar Capacitive Radiofrequency, The one choice for nonablative tissue tightening and contouring", Thermage, Inc. Tech Brochure, Nov. 30, 2005, 8 pgs.

(Continued)

*Primary Examiner* — Kaitlyn E Smith
(74) *Attorney, Agent, or Firm* — Perkins Coie LLP

(57) ABSTRACT

A method and system in accordance with a particular embodiments of the technology includes applying a substance onto skin of a human subject. The applied substance can include a freezing point depressant and a liposome, an oil-in-water emulsion, a water-in-oil emulsion, or an oil-in-oil emulsion and can be configured to protect or target tissue. The substance and a surface of the skin can be cooled using the applicator to treat acne and other skin conditions.

19 Claims, 36 Drawing Sheets

(51) Int. Cl.
  *A61Q 19/06* (2006.01)
  *A61Q 19/08* (2006.01)
  *A61Q 19/00* (2006.01)
  *A61K 9/127* (2006.01)
  *A61F 7/00* (2006.01)
  *A61P 17/10* (2006.01)
  *A61K 9/00* (2006.01)
  *A61K 9/107* (2006.01)
  *A61F 7/02* (2006.01)
  *A61B 90/00* (2016.01)

(52) U.S. Cl.
  CPC .............. *A61F 2007/0093* (2013.01); *A61F 2007/0096* (2013.01); *A61F 2007/0219* (2013.01); *A61K 9/107* (2013.01); *A61K 2800/805* (2013.01)

(56) References Cited

U.S. PATENT DOCUMENTS

| | | |
|---|---|---|
| 1,093,868 A | 4/1914 | Leighty |
| 2,516,491 A | 7/1950 | Swastek |
| 2,521,780 A | 9/1950 | Dodd et al. |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | William et al. |
| 3,282,267 A | 11/1966 | Eidus |
| 3,341,230 A | 9/1967 | Louis |
| 3,502,080 A | 3/1970 | Hirschhorn |
| 3,587,577 A | 6/1971 | Zubkov et al. |
| 3,591,645 A | 7/1971 | Selwitz |
| 3,692,338 A | 9/1972 | Didier |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,008,910 A | 2/1977 | Roche |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,758,217 A | 7/1988 | Gueret |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan et al. |
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,558,376 A | 9/1996 | Woehl |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |

(56) References Cited

U.S. PATENT DOCUMENTS

| | | |
|---|---|---|
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,802,865 A | 9/1998 | Strauss |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,853,364 A | 12/1998 | Baker et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | MacHold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |

(56) References Cited

U.S. PATENT DOCUMENTS

| | | |
|---|---|---|
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 9,149,322 B2 | 10/2015 | Knowlton |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0068874 A1 | 6/2002 | Zuckerwar et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |

(56) References Cited

U.S. PATENT DOCUMENTS

| | | |
|---|---|---|
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1* | 11/2007 | Levinson .................. A61F 7/10 607/96 |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0047360 A1* | 2/2010 | Klaveness ............ A61K 31/132 424/520 |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0241023 A1 | 9/2010 | Gilbert |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |

(56) References Cited

U.S. PATENT DOCUMENTS

| | | |
|---|---|---|
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0288537 A1 | 11/2011 | Halaka |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0283022 A1 | 10/2015 | Lee et al. |
| 2015/0328077 A1 | 11/2015 | Levinson |
| 2015/0328478 A1* | 11/2015 | McDaniel ............ A61B 18/203 607/89 |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0185081 A1 | 7/2018 | O'neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 U | 6/1985 |

(56) References Cited

FOREIGN PATENT DOCUMENTS

| | | |
|---|---|---|
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-57.

(56) References Cited

OTHER PUBLICATIONS

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.
Burge, S.M. et al., "Hair Follicle Destruction and Regeneration in Guinea Pig Skin after Cutaneous Freeze Injury," Cryobiology, 27(2), 1990, pp. 153-163.
Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.
Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.
Donski, P. K. et al., "The Effects of Cooling no. Experimental Free Flap Survival," British Journal of Plastic Surgery, vol. 33, 1980, pp. 353-360.
Duck, F. A., Physical Properties of Tissue, Academic Press Ltd., chapters 4 & 5, 1990, pp. 73-165.
Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.
Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-80.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.

Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002, pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: the Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: an Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: The Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis-a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.

(56) References Cited

OTHER PUBLICATIONS

Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica,vol. 28, Issue 6, 1987, pp. 779-782.
Peterson, L. J. et al., "Bilateral Fat Necrosis of the Scrotum," Journal of Urology, vol. 1161976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly (ethylene glycol) and Poly (ethylene oxide)," http://www.sigmaaldrich.com/materials-sience/materialscience-;products.htmi?TablePage=2020411 0, accessed Oct. 19, 2012.
Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

Skin Prep: Pore Strips
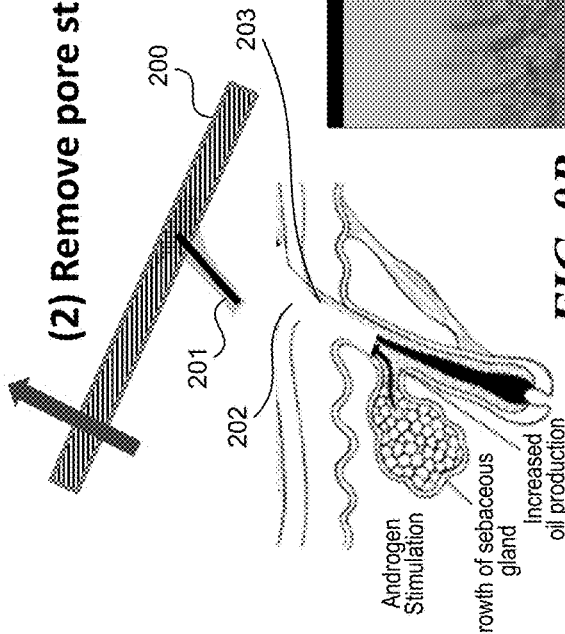
(1) Place Pore Strip
FIG. 9A
(2) Remove pore strip
FIG. 9B
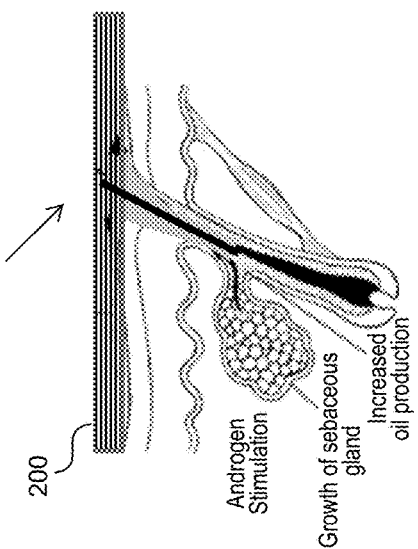
(3) Infuse pore with water or other solution
FIG. 9C
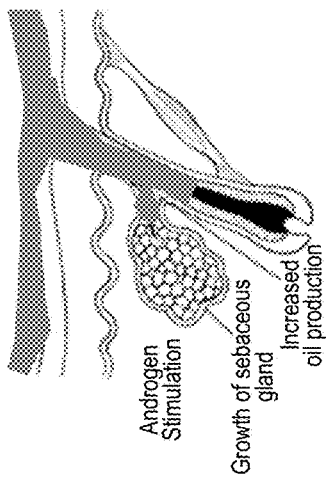

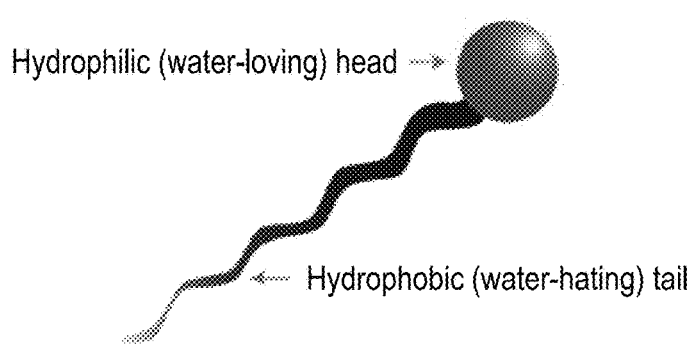
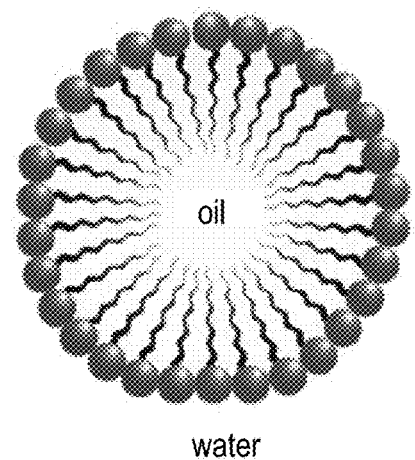
FIG. 12A  FIG. 12B
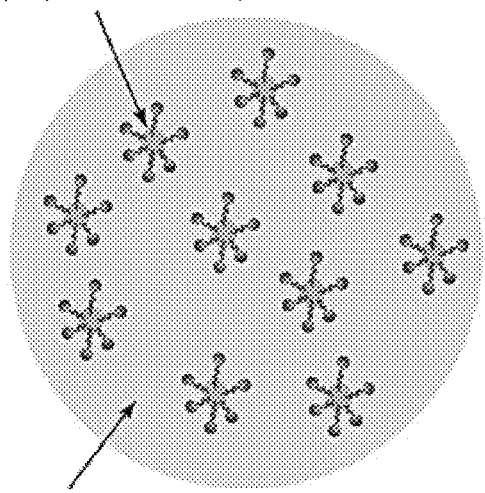
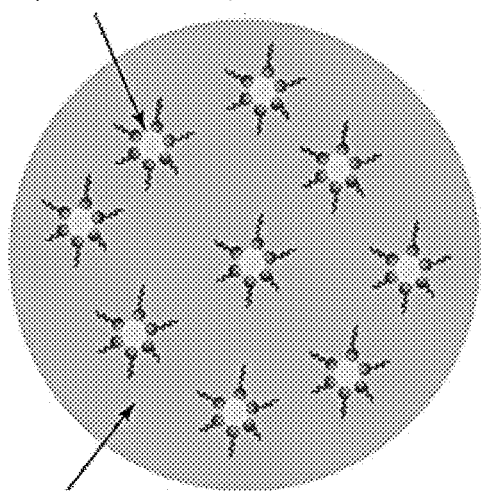
FIG. 13A  FIG. 13B

| Fat | Melt/Freeze Point Temperature |
|---|---|
| Cottonseed Oil | -55F (-48C) |
| Flax Seed Oil | -11F (-24C) |
| Almond Oil | 0F (-18C) |
| Sunflower Oil | 1F (-17C) |
| Safflower Oil | 2F (-17C) |
| Soybean Oil | 3F (-16C) |
| Corn Oil | 12F (-11C) |
| Canola Oil | 14F (-10C) |
| Grapeseed Oil | 14F (-10C) |
| Rice Bran Oil | 14-23F (-5 to -10C) |
| Hemp Seed Oil | 18F (-8C) |
| Olive Oil | 21F (-6C) |
| Sesame Oil | 21F (-6C) |
| Peanut Oil | 37F (3C) |
| Palm Kernel Oil | 75F (24C) |
| Coconut Oil | 77F (25C) |
| Cocoa Butter | 93-100F (34 to 38C) |
| Palm Oil | 95F (35C) |

*FIG. 14*

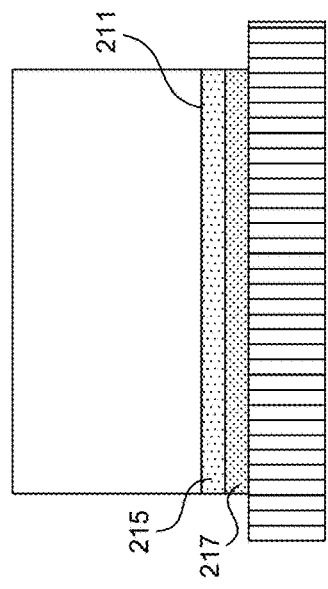
FIG. 20A
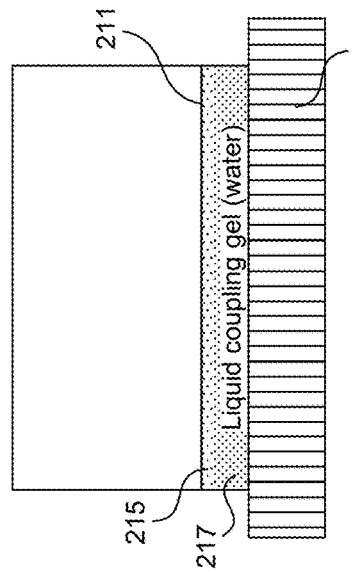
FIG. 20B
FIG. 20C
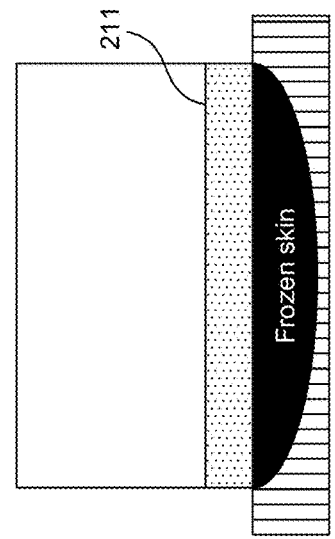
FIG. 20D
FIG. 20E
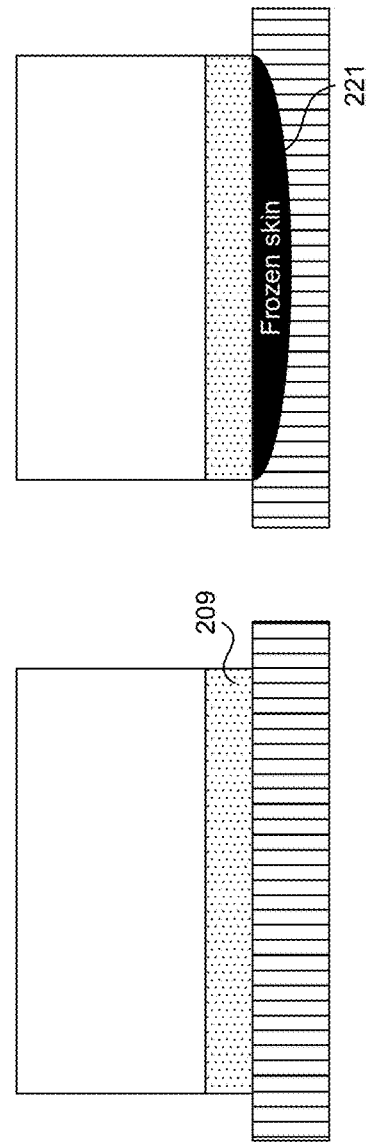
FIG. 20F

LIPOSOMES, EMULSIONS, AND METHODS FOR CRYOTHERAPY

CROSS-REFERENCE TO RELATED APPLICATION

The present application claims the benefit of and priority under 35 U.S.C. § 119(e) to U.S. Provisional Patent Application No. 62/334,330, filed May 10, 2016, which is incorporated herein by reference in its entirety.

INCORPORATION BY REFERENCE

The following U.S. Patent Applications and U.S. Patents are incorporated herein by reference in their entireties:

U.S. Pat. No. 7,854,754 entitled "COOLING DEVICE FOR REMOVING HEAT FROM SUBCUTANEOUS LIPID-RICH CELLS";

U.S. Pat. No. 8,337,539 entitled "COOLING DEVICE FOR REMOVING HEAT FROM SUBCUTANEOUS LIPID-RICH CELLS";

U.S. Patent Publication No. 2013/0158636 entitled "COOLING DEVICE FOR REMOVING HEAT FROM SUBCUTANEOUS LIPID-RICH CELLS";

U.S. Pat. No. 8,192,474 entitled "TISSUE TREATMENT METHODS";

U.S. Patent Publication No. 2013/0066309 entitled "TISSUE TREATMENT METHODS";

U.S. Patent Publication No. 2015/0328077 entitled "TISSUE TREATMENT METHODS";

U.S. Pat. No. 9,132,031 entitled "COOLING DEVICE HAVING A PLURALITY OF CONTROLLABLE COOLING ELEMENTS TO PROVIDE A PREDETERMINED COOLING PROFILE";

U.S. Pat. No. 9,375,345 entitled "COOLING DEVICE HAVING A PLURALITY OF CONTROLLABLE COOLING ELEMENTS TO PROVIDE A PREDETERMINED COOLING PROFILE";

U.S. Publication No. 2015/0342780 entitled "COOLING DEVICE HAVING A PLURALITY OF CONTROLLABLE COOLING ELEMENTS TO PROVIDE A PREDETERMINED COOLING PROFILE";

U.S. Patent Publication No. 2008/0077201 entitled "COOLING DEVICES WITH FLEXIBLE SENSORS";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Patent Publication No. 2014/0005760 entitled "CRYOPROTECTANT FOR USE WITH A TREATMENT DEVICE FOR IMPROVED COOLING OF SUBCUTANEOUS LIPID-RICH CELLS";

U.S. Patent Publication No. 2007/0270925 entitled "METHOD AND APPARATUS FOR NON-INVASIVELY REMOVING HEAT FROM SUBCUTANEOUS LIPID RICH CELLS INCLUDING A COOLANT HAVING A PHASE TRANSITION TEMPERATURE";

U.S. Patent Publication No. 2009/0118722 entitled "METHOD AND APPARATUS FOR COOLING SUBCUTANEOUS LIPID-RICH CELLS OR TISSUE";

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Patent Publication No. 2013/0079684 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Pat. No. 9,408,745 entitled "MONITORING THE COOLING OF SUBCUTANEOUS LIPID-RICH CELLS, SUCH AS THE COOLING OF ADIPOSE TISSUE";

U.S. Patent Publication No. 2013/0116758 entitled "MONITORING THE COOLING OF SUBCUTANEOUS LIPID-RICH CELLS, SUCH AS THE COOLING OF ADIPOSE TISSUE";

U.S. Pat. No. 8,523,927 entitled "SYSTEM FOR TREATING LIPID-RICH REGIONS";

U.S. Patent Publication No. 2014/0067025 entitled "SYSTEM FOR TREATING LIPID-RICH REGIONS";

U.S. Patent Publication No. 2009/0018624 entitled "LIMITING USE OF DISPOSABLE SYSTEM PATIENT PROTECTION DEVICES";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Pat. No. 8,275,442 entitled "TREATMENT PLANNING SYSTEMS AND METHODS FOR BODY CONTOURING APPLICATIONS";

U.S. Patent Publication No. 2013/0158440 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Pat. No. 8,676,338 entitled "COMBINED MODALITY TREATMENT SYSTEMS, METHODS AND APPARATUS FOR BODY CONTOURING APPLICATIONS";

U.S. Patent Publication No. 2014/0316393 entitled "COMBINED MODALITY TREATMENT SYSTEMS, METHODS AND APPARATUS FOR BODY CONTOURING APPLICATIONS";

U.S. Pat. No. 8,603,073 entitled "SYSTEMS AND METHODS WITH INTERRUPT/RESUME CAPABILITIES FOR COOLING SUBCUTANEOUS LIPID-RICH CELLS";

U.S. Patent Publication No. 2013/0245731 entitled "SYSTEMS AND METHODS WITH INTERRUPT/RESUME CAPABILITIES FOR COOLING SUBCUTANEOUS LIPID-RICH CELLS";

U.S. Pat. No. 8,702,774 entitled "DEVICE, SYSTEM AND METHOD FOR REMOVING HEAT FROM SUBCUTANEOUS LIPID-RICH CELLS";

U.S. Patent Publication No. 2014/0257443 entitled "DEVICE, SYSTEM AND METHOD FOR REMOVING HEAT FROM SUBCUTANEOUS LIPID-RICH CELLS";

U.S. Patent Publication No. 2014/0257443 entitled "COMPOSITIONS FOR USE WITH A SYSTEM FOR IMPROVED COOLING OF SUBCUTANEOUS LIPID-RICH TISSUE";

U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";

U.S. Pat. No. 6,041,787 entitled "USE OF CRYOPROTECTIVE AGENT COMPOUNDS DURING CRYOSURGERY";

U.S. Pat. No. 6,032,675 entitled "FREEZING METHOD FOR CONTROLLED REMOVAL OF FATTY TISSUE BY LIPOSUCTION";

U.S. Pat. No. 9,314,368 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Pat. No. 9,545,523 entitled "MULTI-MODALITY TREATMENT SYSTEMS, METHODS AND APPARATUS FOR ALTERING SUBCUTANEOUS LIPID-RICH TISSUE";

U.S. Patent Publication No. 2014/0277302 entitled "TREATMENT SYSTEMS WITH FLUID MIXING SYSTEMS AND FLUID-COOLED APPLICATORS AND METHODS OF USING THE SAME";

U.S. Patent Publication No. 2015/0216720 entitled "TREATMENT SYSTEMS, METHODS, AND APPARATUSES FOR IMPROVING THE APPEARANCE OF SKIN AND PROVIDING FOR OTHER TREATMENTS";

U.S. Patent Publication No. 2015/0216816 entitled "COMPOSITIONS, TREATMENT SYSTEMS AND METHODS FOR IMPROVED COOLING OF LIPID-RICH TISSUE";

U.S. Patent Publication No. 2015/0216719 entitled "TREATMENT SYSTEMS AND METHODS FOR TREATING CELLULITE AND FOR PROVIDING OTHER TREATMENTS";

U.S. patent application Ser. No. 14/662,181 entitled "TREATMENT SYSTEMS, DEVICES, AND METHODS FOR COOLING TARGETED TISSUE";

U.S. patent application Ser. No. 14/710,407 entitled "TREATMENT SYSTEMS WITH ADJUSTABLE GAP APPLICATORS AND METHODS FOR COOLING TISSUE";

U.S. Patent Publication No. 2016/0054101 entitled "TREATMENT SYSTEMS, SMALL VOLUME APPLICATORS, AND METHODS FOR TREATING SUBMENTAL TISSUE";

U.S. Patent Publication No. 2016/0051308 entitled "STRESS RELIEF COUPLINGS FOR CRYOTHERAPY APPARATUSES";

U.S. Patent Publication No. 2016/0089550 entitled "TREATMENT SYSTEMS, METHODS, AND APPARATUSES FOR ALTERING THE APPEARANCE OF SKIN";

U.S. Patent Publication No. 2017/0007309 entitled "TREATMENT SYSTEMS AND METHODS FOR AFFECTING GLANDS AND OTHER TARGETED STRUCTURES";

U.S. Patent Publication No. 2016/0317346 entitled "SYSTEMS AND METHODS FOR MONITORING COOLING OF SKIN AND TISSUE TO IDENTIFY FREEZE EVENTS";

U.S. patent application Ser. No. 15/271,121 entitled "TRANSCUTANEOUS TREATMENT SYSTEMS, COOLING DEVICES, AND METHODS FOR COOLING NERVES";

U.S. patent application Ser. No. 15/296,853 entitled "VASCULAR TREATMENT SYSTEMS, COOLING DEVICES, AND METHODS FOR COOLING VASCULAR STRUCTURES";

U.S. patent application Ser. No. 15/400,885 entitled "TEMPERATURE-DEPENDENT ADHESION BETWEEN APPLICATOR AND SKIN DURING COOLING OF TISSUE";

U.S. Provisional Patent Application Ser. No. 62/334,213 entitled "SKIN FREEZING SYSTEMS FOR TREATING ACNE AND SKIN CONDITIONS";

U.S. Provisional Patent Application Ser. No. 62/334,317 entitled "HYDROGEL SUBSTANCES AND METHODS OF CRYOTHERAPY";

U.S. Provisional Patent Application Ser. No. 62/334,337 entitled "PERMEATION ENHANCERS AND METHODS OF CRYOTHERAPY"; and U.S. Provisional Patent Application Ser. No. 62/297,054 entitled "COOLING CUP APPLICATORS WITH CONTOURED HEADS AND LINER ASSEMBLIES".

TECHNICAL FIELD

The present disclosure relates generally to systems for cooling tissue. In particular, several embodiments are directed to treatment systems, methods, and substances for controllably cooling tissue to treat acne or other conditions.

BACKGROUND

Exocrine glands found in the skin have a role in maintaining skin health, including lubricating, waterproofing, cleansing and/or cooling the skin or hair follicles of the body by excreting water-based, oily and/or waxy substances through skin pores or hair follicles. Overproduction and/or oversecretion of these substances by certain exocrine glands, such as sebaceous glands and sudoriparous glands (e.g., sweat glands), can cause unappealing skin disorders that have proved difficult to treat. For example, overproduction of sebum, a waxy substance produced and secreted by sebaceous glands, can lead to the formation of comedones (e.g., blackheads, whiteheads, etc.) and other inflammatory conditions of the skin associated with acne (e.g., inflamed papules, pustules, nodules, etc.), which can potentially lead to scarring of the skin. Overproducing sebaceous glands associated with hair follicles are mostly found in highly visible regions of the body, such as along the face, neck, upper chest, shoulders and back.

Hyperhidrosis is a condition associated with excessive sweating caused by the overproduction and secretion of sweat from sweat glands in the skin of mammals. Excessive sweating from eccrine sweat glands, which are distributed almost all over the body, can cause discomfort and embarrassment. For example, focal hyperhidrosis can occur on the palms of the hands, soles of the feet, face and scalp. Apocrine sweat glands, particularly in the axilla (i.e., armpits), have oil-producing cells that can contribute to undesirable odor.

Treatments for these and other skin and tissue conditions are often ineffective, non-lasting, and/or have undesirable side-effects.

BRIEF DESCRIPTION OF THE DRAWINGS

The patent or application file contains at least one drawing executed in color. Copies of this patent or patent application publication with color drawings will be provided by the Office upon request and payment of the necessary fee.

Many aspects of the present invention can be better understood with reference to the following drawings. Identical reference numbers identify similar elements or acts. The sizes and relative positions of elements in the drawings are not necessarily drawn to scale.

FIGS. 9A-9C show stages of a method for preparing a treatment site in accordance with an embodiment of the disclosed technology.

FIG. 12A shows an emulsifier or surfactant with a hydrophilic head and a hydrophobic tail.

FIG. 12B shows an agent entrapped by emulsifiers.

FIGS. 13A and 13B show an oil-in-water emulsion and a water-in-oil emulsion.

FIG. 14 is a table with melting/freezing point temperatures for fats.

FIGS. 20A-20F illustrate stages of one method of freezing tissue without supercooling.

DETAILED DESCRIPTION

A. Overview

Figure 1:
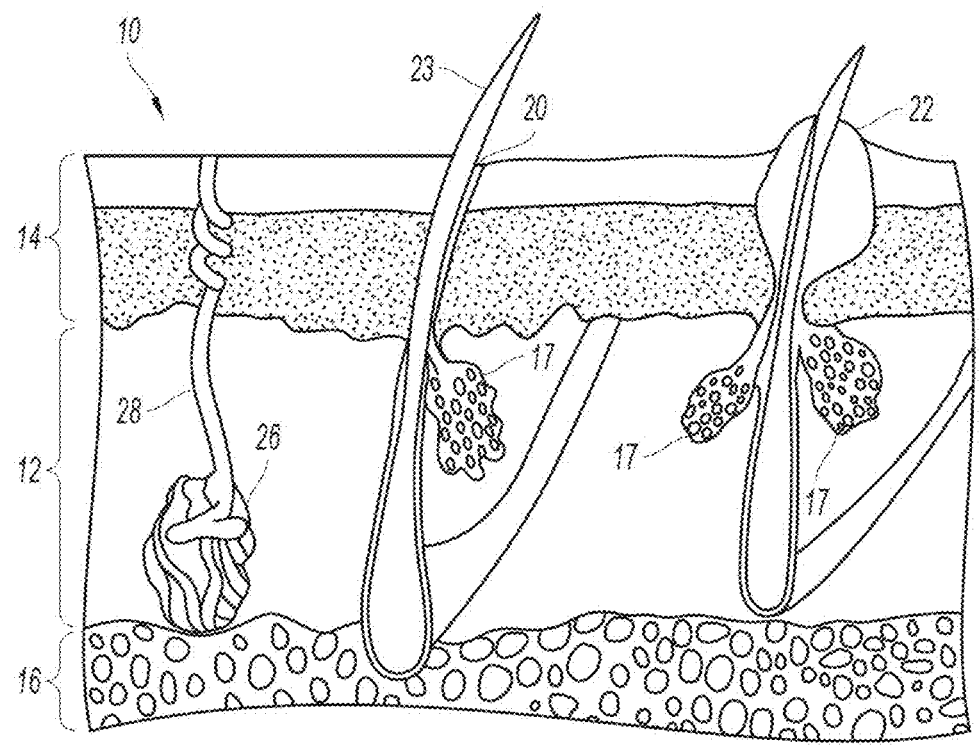
FIG. 1 is a schematic cross-sectional view of the skin, dermis, and subcutaneous tissue of a subject.

The present disclosure describes treatment systems and substances for improving the appearance, function and health of tissue and for performing other treatments. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the technology but are not described in detail.

Various aspects of the technology are directed to cooling a surface of a patient's skin to produce a cooling event (e.g., a partial freeze event, a total freeze event, etc.) that affects tissue, cells, structures, appendages, or targeted features. Systems disclosed herein can target glands (e.g., exocrine glands, sebaceous glands, sweat glands, sudoriparous glands, etc.), structures in the skin (e.g., hair follicles, superficial nerves, etc.), and/or layer(s) of tissue (e.g., dermal layer, epidermal layer, subcutaneous layer, sub-layer(s) of the epidermis, dermis, subcutaneous, etc.). In some embodiments, the cooling event reduces or limits overproduction and/or oversecretion of exocrine glands to treat comedones and/or other inflammatory conditions of the skin associated with acne, such as inflamed papules, pustules, nodules, etc. For example, the cooling event can cause an effective amount of thermal injury to glands to reduce or limit overproduction and/or oversecretion by those glands to reduce or eliminate acne or other skin conditions. The cooling event can include freezing a region of the dermal layer containing the targeted exocrine glands without affecting non-targeted tissue. Treatment applicators can be configured for use along the face, neck, upper chest, shoulders, back, and other treatment sites and can target specific layers in the skin, subcutaneous tissue, specific structures, particular cells, etc.

In some embodiments, a method for treating a subject's skin includes applying a coupling media to the skin. The coupling media can include a freezing point depressant and either a liposome, an oil-in-water emulsion, a water-in-oil emulsion, or an oil-in-oil emulsion containing the freezing point depressant to enhance delivery of the freezing point depressant to the skin. The coupling media and a surface of the skin can be cooled with an applicator to a temperature below 0° C. to treat the skin.

In one embodiment, a method for treating a subject's skin includes applying a coupling media to a surface of the subject's skin such that an ice nucleating agent contained in the applied coupling media does not directly contact epidermal cells for a period of time. An applicator is applied to the subject's skin. The coupling media and the surface of the skin are cooled to lower a temperature of the surface of the skin below 0° C. to cause a freeze event initiated by the ice nucleating agent so as to freeze the skin. In one procedure, an applied is held against the skin while the applicator cools the skin.

In another embodiment, a system for treating a subject includes an applicator and a controller. The applicator can be configured to reduce a temperature of a target region beneath a surface of the subject's skin to reduce the temperature of target tissue from a natural body temperature to a temperature for freezing the target tissue. The coupling media can include a freezing point depressant and either a liposome, an oil-in-water emulsion, a water-in-oil emulsion, or oil-in-oil emulsion containing the freezing point depressant to enhance delivery of the freezing point depressant to the skin. The controller can be programmed to cause the applicator to cool the coupling media and a surface of the skin to a temperature below 0° C. to freeze the skin for a period of time.

At least some of the embodiments disclosed herein can be for cosmetically beneficial treatments. As such, some treatment procedures may be for the sole purpose of altering a treatment site to conform to a cosmetically desirable look, feel, size, shape or other desirable cosmetic characteristic or feature. Accordingly, cosmetic procedures can be performed without providing any or minimal therapeutic effect. For example, some treatment procedures may be directed to goals, such as the reduction of acne, that do not include restoration of health, physical integrity, or the physical well-being of a subject. In some embodiments, methods can target skin irregularities, wrinkles, and sebaceous glands to treat acne; sweat glands to treat hyperhidrosis; hair follicles to injure and remove hair; or other targeted cells to change a subject's appearance or address a condition. Treatments may have therapeutic outcomes (whether intended or not), such as, psychological benefits, alteration of body hormone levels (by the reduction of adipose tissue), etc. Various aspects of the methods disclosed herein can include cosmetic treatment methods for achieving a cosmetically beneficial alteration of a portion of tissue within the target region. Such cosmetic methods can be administered by a non-medically trained person. The methods disclosed herein can also be used to (a) improve the appearance of skin by tightening the skin, improving skin tone and texture, eliminating or reducing wrinkles, increasing skin smoothness, thickening the skin, (b) improve the appearance of cellulite, and/or (c) treat sebaceous glands, hair follicles, and/or sweat glands.

At least some embodiments of the technology include producing one or more controlled freeze events. The location and extent of freezing can be controlled to produce a therapeutic or cosmetic effect. Nucleation initiators, nucleation inhibitors, and/or treatment substances can be used before, during, and/or after the freeze event. The nucleation initiators can include, without limitation, ice nucleation agents, injectable substances (e.g., saline, ice slurries, etc.), energy that promotes ice nucleation, or other initiators that affect freezing. Nucleation inhibitors can include, without limitation, cryoprotectant solutions, freeze temperature depressants, and/or heaters.

According to one aspect of the technology, a subject's skin is lowered to below its melting/freezing point ("melting point"). The skin temperature is monitored to control an amount of non-freezing effects. An ice crystal contacts skin to cause a freeze event in the skin. The skin can be monitored to control an amount of freeze treatment. The skin can also be monitored to detect any further non-freeze effects, freeze effects, or thaw effects to precisely and predictably control an overall level of treatment. Skin preparation techniques can be utilized to enhance absorption of the substance into the skin by abrading and/or scrapping of the epidermis. Example substances include thermal coupling gels, cryoprotectant solutions, and/or ice nucleating agents that may be incorporated into or part of a hydrogel material, a liposome, an emulsion, a nano-emulsion, nanoparticle mixture or solution, and/or combinations thereof. Nano-emulsions and nanoparticles may be desirable since their small size makes them suitable to being absorbed into the epidermis and dermis by traveling along hair follicle apertures and skin pore apertures. A cryoprotectant can be used to enhance the amount of non-freezing treatment to be delivered prior to any freeze event because the cryoprotectant can allow significant supercooling of the skin prior to initiating a freeze event. In one embodiment, an ice nucleating agent is utilized to reliably and predictably form ice crystals.

An applicator can predictably freeze targeted tissue or structures by producing a freeze event that occurs in an expected way. For example, tissue can be cooled to start a freeze event at an anticipated time (e.g., at a particular time or within an expected period of time), propagate the freeze at a desired rate, achieve a desired extent of freezing, or the like. Treatment parameters can be selected based on the desired predictability of the freeze event. For example, the skin surface can be cooled to produce a freeze event at least 80%, 85%, 90%, or 95% of the time in a typical patient. This provides a predictable freeze. If a freeze event does not occur, the skin can be warmed and cooled again to produce a freeze event.

One advantage of freezing is that for a given amount of desired tissue damage, a procedure that produces freezing can take considerably less time than a procedure which does not involve freezing. This is because with freezing, cell walls are damaged.

Damage to tissue due to freezing and cooling is mainly dependent on, for example, cooling rate, end temperature, holding time (unfrozen and/or frozen), and thawing rate. These variables can be controlled to achieve the desired cryoinjury to target tissue.

Tissue damage at the cellular scale is known to occur due to intracellular (IIF) and extracellular ice (EIF) formation. Cryoinjury due to IIF can be accomplished by inducing irreversible damage to the tissues and by necrosis destroying cell organelles and membranes from the inside. Cryoinjury due to extracellular ice formation is mainly due to hyperosmolarity in extracellular space and dehydration of the cells because of the extracellular ice. These processes provoke direct cell death or programmed cell death (e.g., apoptosis of the cells).

In order to accomplish tissue injury, a sufficient end low temperature can be reached. Individual tissues and cells may have different susceptibility to cold. Consequently, lethal temperatures can vary among different components of the skin. Multiple cycles of a treatment temperature protocol should increase efficacy as well.

Holding time in a frozen state enhances cryogenic tissue injury mechanisms. As ice crystals grow in size during a holding time period, the more they will enhance injury due to IIF and/or EIF.

Thawing is a destructive factor facilitating recrystallization (ice crystal restructuring), namely, crystals growing bigger, and rehydration of cells causing membrane disruption and cell death.

For skin, cold can affect the blood microcirculation which can induce reversible or irreversible vascular changes. During cooling there is vasoconstriction of blood vessels which in some temperature treatment protocols may provoke the occurrence of stasis and tissue ischaemia. During freezing, there may be damage to the endothelium of blood vessels and other cellular injury due to EIF and IIF. Vasoconstriction facilitates hypoxia, a state in which cells release vasodilatation cytokines which after thawing enhance refractory vasodilatation and reperfusion injury. Reperfusion also facilitates inflammatory and perivascular oedema of tissues.

Additionally, partially or totally frozen tissue has a higher thermal conductivity and a lower specific heat than unfrozen tissue. The thermal conductivity continues to increase and the specific heat continues to decrease as additional tissue is frozen. This change in thermal properties can result in enhanced efficiency (e.g., a factor of four to eight improvement in cooling efficiency) as compared to a treatment which does not involve freezing, even when the treatment temperatures of the non-freezing treatment with supercooling are similar to the freezing treatment temperature. Accordingly, with freezing, the depth of penetration of cooling into the skin and surrounding tissue can be significantly faster than without freezing.

Some embodiments are directed to treating tissue below the skin or sublayers or sub-thicknesses of the skin, such as the epidermis, dermis, subdermis, subcutaneous, and sublayers thereof to treat wrinkles, fine lines, pores, moles, freckles, port wine stains, and other vascular issues, acne, or the like. Additionally or alternatively, treatments can be performed to rejuvenate skin, resurface skin, address skin coloration issues, block pain, etc., and to affect targets, such as appendages, cellular elements, or combinations thereof. Appendages that can be treated include, without limitation, hair follicles, sebaceous glands, sweat glands, arrector pili, nerves, blood vessels, etc. Cellular elements that can be treated include, without limitation, corneocytes, keratinocytes, melanocytes, sebocytes, fibroblasts, blood cells, collagen, elastin fibers, etc. The systems and methods disclosed herein are useful for treating the targets and conditions disclosed herein.

References throughout this specification to "one example," "an example," "one embodiment," or "an embodiment" mean that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. The headings provided herein are for convenience only and are not intended to limit or interpret the scope or meaning of the technology.

B. Treatment Sites

FIG. 1 is a schematic cross-sectional view of the skin, dermis, and subcutaneous tissue of a subject. A subject's skin 10 includes the dermis 12 located between the epidermis 14 and the subcutaneous layer 16. The dermis 12 includes sebaceous glands 17 that produce sebum, a waxy substance secreted for moisturizing the skin and hair. Acne is a skin condition typically characterized by excess sebum that may plug hair follicles and/or pores. The level of sebum production may vary between individuals and may vary by body location depending on the number and sizes of the sebaceous glands. Sebum can flow along the healthy hair follicle 20 to moisturize the hair 23 and/or epidermis 14. When the sebaceous glands 17 produce excess sebum, it can collect and/or become trapped in hair follicles. Overproduction and/or entrapment of sebum can lead to formation of comedones (e.g., blackheads, whiteheads, etc.), as well as other inflammatory conditions of the skin associated with acne (e.g., inflamed papules, pustules, nodules, etc.). In some individuals, inflamed follicles and pores can become infected and the condition can potentially lead to scarring of the skin. The illustrated hair follicle 22 is clogged with excess sebum to form a pimple or red spot. Other medical conditions associated with overactive sebaceous glands 17 include sebaceous cysts, hyperplasia and sebaceous adenoma. Non-medical, but cosmetically unappealing, conditions associated with overactive sebaceous glands include oily skin and/or oily hair (e.g., on the scalp).

Another skin condition is hyperhidrosis. Hyperhidrosis is characterized by abnormal sweating due to high secretion levels of sweat glands 26. Eccrine sweat glands are controlled by the sympathetic nervous system and regulate body temperature. When an individual's body temperature rises, eccrine sweat glands secrete sweat (i.e., water and other solutes) that flows through a gland tubule 28. The sweat can evaporate from the skin surface to cool the body. Apocrine sweat glands (not shown) secrete an oil-containing sweat into hair follicles 20. The axilla (e.g., armpit) and genital regions often have a high concentration of apocrine sweat glands. Hyperhidrosis occurs when sweat glands produce and secrete sweat at levels above that required for regulation of body temperature, and the condition can be generalized or localized (i.e., focal hyperhidrosis) to specific body parts (e.g., palms of hands, soles of feet, brow, scalp, face, underarms, etc.).

Figure 2:
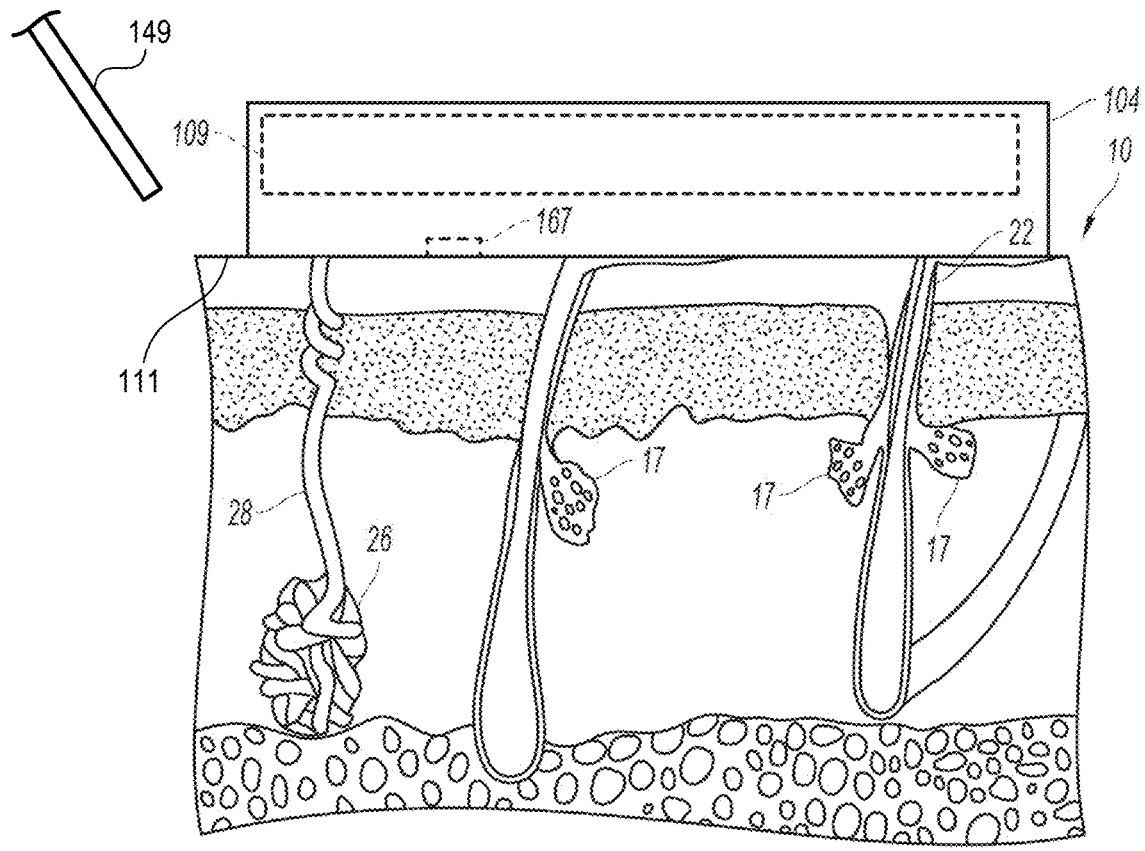
FIG. 2 is a schematic cross-sectional view of the skin, dermis, and subcutaneous tissue of the subject in FIG. 1 after treating sebaceous glands.

FIG. 2 is a schematic cross-sectional view of the skin and a side view of a treatment device in the form of a thermoelectric applicator 104 ("applicator 104") applied to the skin to treat acne, hyperhidrosis, and other skin conditions by freezing the skin. The applicator 104 can controllably produce predictable freeze events to avoid under treatment, overtreatment, and/or undesirable side effects, such as damage to non-targeted tissue or structures. Freezing skin to damage tissue can be difficult to control, thus often results in undertreatment or overtreatment. This is because freezing of skin and tissue below the skin tend to be somewhat random and unpredictable. Water in biological tissue, such as the skin 10, has the tendency to remain in a liquid state for a certain period of time, even if its temperature is lowered below its melting/freezing point, a phenomenon termed "supercooling." The terms "supercooling," "supercooled," and "supercool" refer to a condition in which a material is at a temperature below its freezing/melting point but is still in an unfrozen or mostly unfrozen state. It can be somewhat unpredictable whether a freeze event will ever occur, and if so when the freeze event will occur during the treatment and how long tissue will be in a frozen state. In addition, it is often very difficult to control freeze-thaw parameters, such as a freezing rate, target freeze temperatures, duration of freeze events, and a warming rate. These freeze-thaw parameters need to be controlled to achieve predictable therapeutic outcomes. It may be difficult to control freeze-thaw parameters, thus making it difficult to control an amount of treatment. When the amount of treatment is too large, undesirable side effects can occur, such as undesired skin pigmentation changes, and when it is too small, insufficient efficacy can result. This lack of control also can make it difficult to target certain tissue for treatment and to minimize treatment of other specific non-targeted tissue.

The applicator 104 can accurately target tissue while minimizing or limiting effects on non-targeted tissue. It has been discovered that when an ice crystal contacts skin 10 of the subject at a temperature which is below its phase transition temperature (e.g., melting/freezing temperature) and in a supercooled state, a freeze event can be immediately triggered in the skin. The ice crystal can thus be used to predictably control initiation of the freeze event. Once the freeze event is triggered, it can rapidly propagate through the volume of supercooled tissue. The heat of fusion released during freezing may take the bulk tissue out of its supercooled state, and thereafter the partially frozen skin may prevent non-frozen tissue from reentering a supercooled state. Additionally, the heat of fusion in some procedures, the period of time from the beginning of a freeze event in supercooled tissue to the point where the tissue is largely no longer in a supercooled state may be 1 second, 2 seconds, 3 seconds, 5 seconds, 10 seconds, or another suitable period of time. The time period for supercooling can depend on the target location, volume of targeted tissue, supercooled tissue volume, temperature profile, tissue characteristics (e.g., water content of tissue), and/or additives (e.g., compositions, energy, etc.) that may be used as part of the procedure. Because freeze propagation rates may be strongly dependent on the supercool temperature, the temperature of the supercooled tissue can be decreased or increased to increase or decrease, respectively, freeze propagation rates.

The applicator 104 can be used to precisely control a start time of the freeze event, an amount of damage caused by an initial freeze event (e.g., by controlling an amount of supercooling created prior to initiating the freeze event), a duration of the freeze event (e.g., by controlling a temperature of an applicator), and thawing rate (e.g., start of thaw cycle, etc.). The timing of freeze events can be precisely controlled by controlling the generation of the ice crystal and when the ice crystal comes in contact with supercooled skin so that freeze events can be produced "on command," and this control allows for specialized treatment methods to be implemented to controllably and effectively treat a range of tissue while controlling and/or limiting damage to tissue. In addition, additives can be used to manage freeze events at varying optimum temperatures to target tissue at varying skin depths while controlling tissue damage, extent of injury to non-targeted tissue, etc. By controlling when and how to freeze, treatment procedures can target certain tissue without targeting other tissue while also controlling a level of treatment of targeted tissue and effects to non-targeted tissue.

FIG. 2 shows the skin 10 after a freeze-induced injury has affected the sebaceous glands 17 to reduce or limit sebum production. Skin 10 has been frozen to controllably disrupt or injure the sebaceous glands 17 or associated structures which can be an effective treatment for acne. Although the effect to the sebaceous glands 17 is shown while the applicator 104 is applied to the skin 10, it may take a relatively long period of time (e.g., days, weeks, months, etc.) for the glands to be reduced after treatment. The sebum production level of the two sebaceous glands 17 in FIG. 2, along the hair follicle 22, has been substantially reduced to inhibit clogging to minimize, reduce, or eliminate acne. The sweat gland 26 can also be targeted. For example, the applicator 104 can produce a partial or total freeze event, non-freezing cooling event, or supercooling event to affect the sweat gland 26 and/or gland tubule 28 in a region of the skin located along the hands, armpits, or other locations with excessive sweat. Other structures in the dermis or other layers of tissue can be targeted. Accordingly, the cold, associated with a controlled freeze generated by the applicator 104, can generally reduce/relieve inflammation associated with acne and be an important treatment pathway. Any and all these pathways of treatment are encompassed by at least one of the embodiments of the technology disclosed herein.

In some embodiments, a temperature-controlled surface 111 of the applicator 104 can be cooled to affect target structures, such as glands, hair follicles, nerves (e.g., superficial nerves), or one or more layers of tissue (e.g., dermal layer, epidermal layer, subcutaneous layer, sub-layer(s) of the epidermis, dermis, and/or subcutaneous layer, etc.). To treat acne, the surface of the subject's skin can be cooled to produce a temperature at or below −15° C., −10° C., −5° C., 0° C., 5° C., 10° C., 15° C., or 20° C. and to produce either a cooling non-freeze event or a freeze event in a targeted portion of the skin. Localized freeze events can be generated to affect targeted structures while minimizing, limiting, or substantially preventing thermal injuries to non-targeted tissue, structures, etc. Substances used with the applicator 104 can include cryoprotectants, nucleating agents, liposomes, emulsions, hydrogels, combinations thereof, or the like. Mechanical energy (e.g., massaging), ultrasound energy, radiofrequency (RF) energy, and/or freeze initiators can control a freeze event by, for example, initiating, promoting, and/or inhibiting freezing. In some procedures, ultrasound energy is delivered to supercooled tissue to trigger freezing in the tissue. Radiofrequency energy can be used to warm tissue to isolate freezing to a target region. Freeze initiators can be used to initiate a freeze event in the tissue or freeze event in another substance that ultimately causes freezing in the tissue. Example freeze initiators include, but are not limited to, one or more water ice crystals, cryoprobes, or substances that rapidly freeze to produce freeze events. Freeze events can include partially or completely freezing liquids or lipids proximate to or within cells, and/or structures, to destroy, reduce, disrupt, modify, or affect targeted features. The characteristics of the cooling event or freeze event can be controlled to manage thermal injury. Such characteristics include, without limitation, the amount of cooling or freezing, density and distribution of ice crystals, freezing rate, or the like.

Cryotherapy can affect, without limitation, glandular function, structures of glands (e.g., gland portions, duct portions, etc.), number of glands, sizes of glands, and/or number and/or sizes of cells. The freeze event can be maintained for a period of time long enough to elicit a desired result. In some embodiments, for treating exocrine glands, a subject's skin can be cooled to produce a partial freeze event that destroys, reduces, disrupts, modifies, or affects cells or structures of exocrine glands or the supporting anatomical features (e.g., ducts, pores, hair follicles, etc.). The level of freezing can be controlled to limit unwanted tissue damage, such as damage to non-targeted tissue, excess damage to targeted tissue (e.g., to avoid excess damage to targeted tissue), and so forth. The skin surface can be continuously or periodically cooled or heated to increase or decrease, respectively, the number and/or sizes of ice crystals at the target region. In one procedure, the tissue can be kept in a supercooled state for longer than, for example, about 1 second, 5 seconds, 10 seconds, 20 seconds, 30 seconds, 1 minute, several minutes, or other time period selected to allow the tissue to reach a steady state temperature and desired width, length, and depth of a tissue volume which is in a supercooled state. Once tissue is frozen, it can be kept in a partially or totally frozen state for longer than about, for example, about 1 second, 5 seconds, 10 seconds, 20 seconds, 30 seconds, 1 minute, several minutes, or other time period selected to achieve desired effects, while reducing or limiting undesired effects, such as frostbite or necrosis.

The applicator 104 can include one or more elements 167 for detecting cooling events, freezing events, supercooling, and so forth. The thermal device 109 can be controlled based on the output from the element 167 to cool a temperature-controlled surface 111, which, in turn, cools the patient's skin. The element 167 can include one or more temperature sensors, pressure sensors, detectors, combinations thereof, or the like. Alternatively, separate sensors can be used to monitor the treatment site.

C. Treatment Systems

Figure 3:
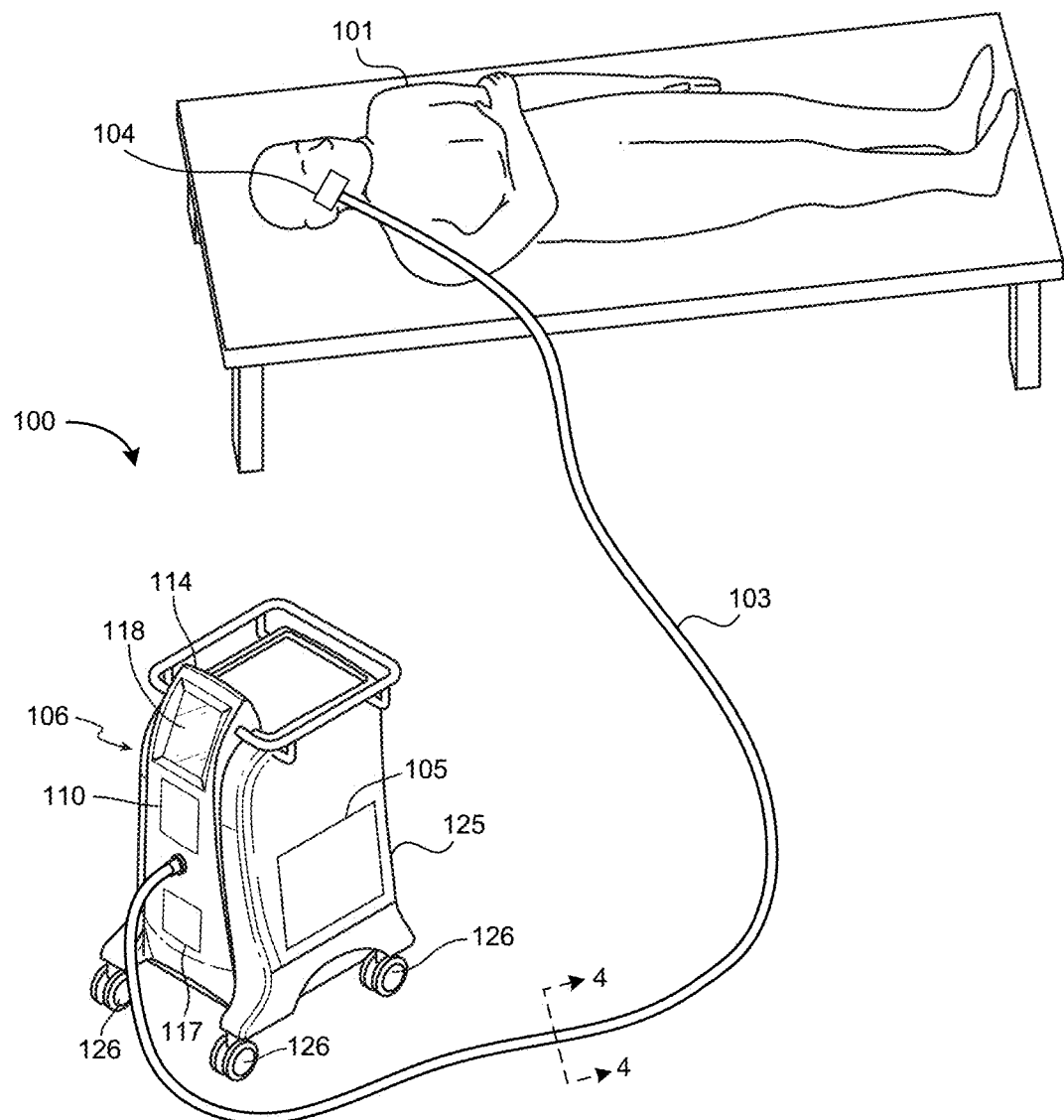
FIG. 3 is a partially schematic, isometric view of a treatment system for non-invasively treating targeted structures in a human subject's body in accordance with an embodiment of the technology.

FIG. 3 is a partially schematic, isometric view of a treatment system for non-invasively treating targeted structures in a body of a human subject 101 in accordance with an embodiment of the technology. The treatment system 100 can include the applicator 104, a connector 103, and a base unit 106. The applicator 104 can be applied to acne-prone regions to reduce the temperature of lipid-producing cells residing in or at least proximate to sebaceous glands (e.g., glandular epithelial cells) to lower the amount of secreted sebum and thereby eliminate, reduce, or limit acne. The applicator 104 can also cool sweat glands and associated structures to treat hyperhidrosis and can perform other treatment procedures. The size and configuration of the applicator 104 can be selected based on the treatment site.

The connector 103 can be a cord that provides energy, fluid, and/or suction from the base unit 106 to the applicator 104. The base unit 106 can include a fluid chamber or reservoir 105 (illustrated in phantom line) and a controller 114 carried by a housing 125 with wheels 126. The base unit 106 can include a refrigeration unit, a cooling tower, a thermoelectric chiller, heaters, or any other devices capable of controlling the temperature of coolant in the fluid chamber 105 and can be connectable to an external power source and/or include an internal power supply 110 (shown in phantom line). The power supply 110 can provide electrical energy (e.g., a direct current voltage) for powering electrical elements of the applicator 104. A municipal water supply (e.g., tap water) can be used in place of or in conjunction with the fluid chamber 105. In some embodiments, the system 100 can include a pressurization device 117 that can provide suction and can include one or more pumps, valves, and/or regulators. Air pressure can be controlled by a regulator located between the pressurization device 117 and the applicator 104. If the vacuum level is too low, tissue may not be adequately (or at all) held against the applicator 104, and the applicator 104 may tend to move along the patient's skin. If the vacuum level is too high, undesirable patient discomfort and/or tissue damage could occur. A vacuum level can be selected based on the characteristics of the tissue and desired level of comfort. In other embodiments, the applicator 104 does not use a vacuum.

An operator can control operation of the treatment system 100 using an input/output device 118 of the controller 114. The input/output device 118 can display the state of operation of the applicator 104 and treatment information. In some embodiments, the controller 114 can be communicatively coupled to and exchange data with the applicator 104 via a wired connection or a wireless or an optical communication link and can monitor and adjust treatment based on, without limitation, one or more treatment profiles and/or patient-specific treatment plans, such as those described, for example, in commonly assigned U.S. Pat. No. 8,275,442, which is incorporated by reference in its entirety. In some embodiments, the controller 114 can be incorporated into the applicator 104 or another component of the system 100.

Upon receiving input to start a treatment protocol, the controller 114 can cycle through each segment of a prescribed treatment plan. Segments may be designed to supercool tissue, to nucleate supercooled tissue, to freeze tissue, to thaw tissue, to warm tissue, and so on. In so doing, the power supply 110 and the fluid chamber 105 can provide power and coolant to one or more functional components of the applicator 104, such as thermoelectric coolers (e.g., TEC "zones"), to begin a cooling cycle and, in some embodiments, to activate features or modes, such as vibration, massage, vacuum, etc.

The controller 114 can receive temperature readings from temperature sensors, which can be part of the applicator 104 or proximate to the applicator 104, the patient's skin, a patient protection device, etc. It will be appreciated that while a target region of the body has been cooled or heated to the target temperature, in actuality that region of the body may be close, but not equal to, the target temperature, e.g., because of the body's natural heating and cooling variations. Thus, although the system 100 may attempt to heat or to cool tissue to the target temperature or to provide a target heat flux, a sensor may measure a sufficiently close temperature or heat flux. If the target temperature or the flux has not been reached, power can be increased or decreased to change heat flux to maintain the target temperature or "set-point" selectively to affect targeted tissue. The treatment site can be continuously or intermittently evaluated by monitoring various parameters. The skin can be continuously monitored to detect its temperature to determine whether it is in a frozen state, an unfrozen state, or other state.

In some procedures, the applicator 104 can achieve a level or amount of supercooling at a suitable temperature below, for example, −15° C., −10° C., −5° C., or 0° C. After achieving a predetermined level of supercooling, the applicator 104 can automatically start a freeze event. The freeze event can be detected and/or monitored using the applicator 104 or separate device. A level of treatment can be controlled following initiation and/or completion of the freeze event. One or more post freeze protocols can be performed to thaw or otherwise thermally affect tissue to allow treatment to be specifically tailored to effectively treat certain targets, and to not treat or minimize treatment of non-targeted tissue. For example, post-freeze protocols can be used to inhibit, limit, or substantially minimize permanent thermal injuries. In some embodiments, post-freeze protocols can include gradually or rapidly warming non-targeted and targeted tissue.

Figure 4:
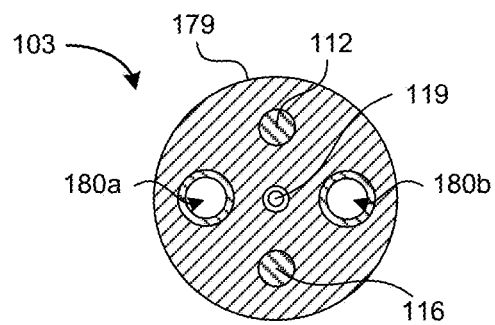
FIG. 4 is a cross-sectional view of a conduit of the treatment system of FIG. 3.

FIG. 4 is a cross-sectional view of the connector 103 taken along line 4-4 of FIG. 3 in accordance with at least some embodiments of the technology. The connector 103 can be a multi-line or multi-lumen conduit with a main body 179 (e.g., a solid or hollow main body), a supply fluid line or lumen 180a ("supply fluid line 180a"), and a return fluid line or lumen 180b ("return fluid line 180b"). The main body 179 may be configured (via one or more adjustable joints) to "set" in place for the treatment of the subject. The supply and return fluid lines 180a, 180b can be tubes made of polyethylene, polyvinyl chloride, polyurethane, and/or other materials that can accommodate circulating coolant, such as water, glycol, synthetic heat transfer fluid, oil, a refrigerant, and/or any other suitable heat conducting fluid. In one embodiment, each fluid line 180a, 180b can be a flexible hose surrounded by the main body 179. Referring now to FIGS. 3 and 4, coolant can be continuously or intermittently delivered to the applicator 104 via the supply fluid line 180a and can circulate through the applicator 104 to absorb heat. The coolant, which has absorbed heat, can flow from the applicator 104 back to the base unit 106 via the return fluid line 180b. For warming periods, the base unit 106 (FIG. 3) can heat the coolant such that warm coolant is circulated through the applicator 104. The connector 103 can also include one or more electrical lines 112 (FIG. 4) for providing power to the applicator 104 and one or more control lines 116 for providing communication between the base unit 106 and the applicator 104. To provide substances, the connector 103 can include one or more tubes or lines 119 for substances to be delivered by the applicator 104. The substances can include coupling media, INAs, solutions (e.g., cryoprotectant solutions), or the like.

Figure 5:
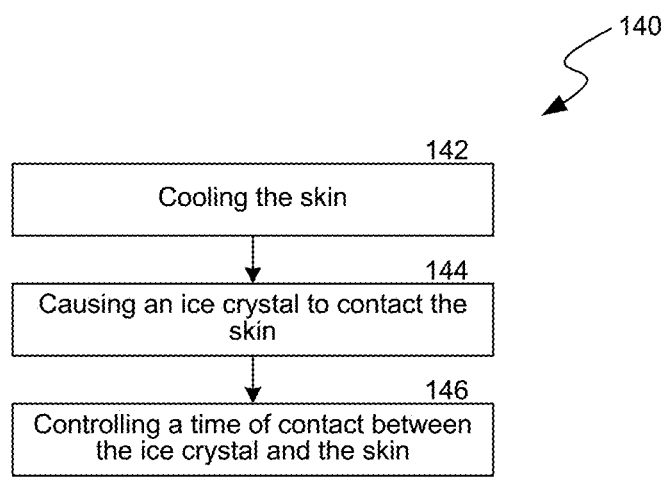
FIG. 5 is a flow diagram illustrating a method for treating a subject's skin in accordance with an embodiment of the technology.

FIG. 5 is a flow diagram illustrating a method 140 for treating a subject's skin in accordance with an embodiment of the technology. Generally, the subject's skin can be cooled below a freezing temperature of fluid in the skin. One or more ice crystals can be moved into contact with the skin to create a predictable freeze event therein. The time of contact between the ice crystals and skin can be controlled to achieve desired freezing. Details of the method 140 are discussed below.

At block 142, the skin can be cooled to lower the temperature of the skin below a freezing temperature of fluid in the skin. For example, the temperature of the skin can be lowered to a first temperature that is more than 3° C., 5° C., 7° C., 9° C., 10° C., or 11° C. below the melting/freezing temperature of fluid in the skin and can be maintained for a first period of time. After the first period of time expires, the skin temperature can be lowered to a second temperature that is lower than the first temperature so as to create an ice crystal. In other embodiments, the first temperature can be maintained at a constant temperature while creating an ice crystal by, for example, altering the composition of a coupling media. The coupling media can freeze and cause ice nucleation in the tissue.

At block 144 of FIG. 5, an ice crystal can contact the subject's skin to inoculate the skin upon contact and to create a predictable freeze event therein. The ice crystal can be formed externally by an applicator. Alternatively, a catheter or other device can introduce the ice crystal into the subject such that the ice crystal physically contacts tissue to be initially frozen. In some procedures, an agent can be cooled and then diluted to produce one or more ice crystals therein. For example, the agent can include a cryoprotectant for protecting tissue. The concentration of cryoprotectant in the agent can be diluted to raise a melting/freezing point of the diluted agent to a value above a temperature of the cryoprotectant so that formation of the ice crystal does not require that the skin temperature be lowered to a value below the melting/freezing temperature of the cryoprotectant.

At block 146, a time of contact between the ice crystal and the skin can be controlled. A user can hold the applicator against the skin surface while the ice crystal contacts the skin surface. Upon completion of a contact period, the system can notify the subject or operator to remove the applicator from the subject. The applicator can be pulled off the subject to stop the crystal contact. Alternatively, the applicator can be warmed to melt the ice crystal at the completion of the desired contact period. The temperature of the applicator can be controlled to set the length of ice crystal/tissue contact, as well as the length of the freeze event by detecting the freeze event and further controlling when the temperature of the skin is raised to a temperature above the ice crystal's melting point to stop the freeze event.

In some treatments, the method 140 can include lowering a temperature of a subject's skin below a melting/freezing point or temperature of target tissue of the skin. The applicator 104 can monitor cooling of the skin using the sensor so that freezing therein does not occur. The amount of non-freezing cooling treatment delivered to the skin can be controlled so that targeted tissue of the skin reaches a predetermined first level at block 142. After the targeted tissue reaches the predetermined first level, the skin is frozen (block 144). The sensor can be used to identify and monitor the freeze event. An ice crystal can come into intimate contact with the supercooled skin during the supercooling period and prior to the time when the beginning of a freeze event is desired to occur, without adverse effects. After the supercooling period has elapsed to create a predetermined first level of supercooling, the ice crystal(s) can be brought into contact with the skin to initiate the freeze event, and damage associated with the initial freeze event can be largely proportional to the level or extent of supercooling. The freeze event can be maintained for any desired period of time, and after the freeze event, additional freeze events can further affect the tissue. The amount of freezing/cooling treatment delivered to the skin can be controlled so that it reaches a predetermined second level. In some treatments, the ice crystal is used to cause freezing of skin in the first level of the supercooled state. The predetermined second level, when combined with the first level, can be selected to provide a therapeutically effective amount of thermal injury.

A shallow skin treatment can include contacting the subject's skin with ice crystals while the skin has a bulk temperature just slightly below its melting/freezing point, such as by 0.2° C., 0.5° C., 1° C., 2° C., or 3° C. There may be minimal to no significant skin supercooling, so that the initial freeze event is small (e.g., a fraction of the tissue initially frozen will be small) and relatively small tissue can be frozen when the initial freeze event occurs. Accordingly, initial tissue damage can be predominately located in the epidermis and upper layer of the dermis, with deeper layers, such as subdermal, fat and muscle tissue, being largely unaffected. As such, treatments can be performed on acne-prone regions where damage to subcutaneous tissue may be problematic and undesired. Once the freeze event occurs, additional tissue in the skin will not enter a supercooled state because ice crystals in the skin can inhibit or prevent further supercooling. Further additional incremental cooling can result in predictable incremental freezing, and if minimal depth of treatment is desired, a tissue thaw protocol can be started immediately or very soon following the freeze event.

The system 100 can also perform deeper treatments, including aggressive and deeper skin treatments, by supercooling targeted tissue and then contacting the targeted tissue with an ice crystal to trigger a freeze event. The supercooled tissue can include epidermal tissue, dermal tissue, subcutaneous tissue and can be cooled as much as by 4° C., 5° C., 6° C., 7° C., 8° C., 9° C., 10° C., 12° C., 15° C., 17° C., 20° C., 25° C., 30° C., or 35° C. and for a significant period of time, such as 30 seconds or 1, 2, 3, 4, 5, 7, 10, 12, 15, 20, 25 or more minutes. The temperature and treatment period can allow for variable and controlled levels of skin supercooling prior to initiating a freeze event. An overall level of treatment can also include multiple treatments, each of which individually delivers a dose which is less than a total dose of treatment to ultimately be delivered. For example, after an initial skin supercooling and freeze event has been performed at a given treatment site, device software can be programmed to repeat the supercooling and freeze event cycle a second time, optionally after a tissue rewarming/thaw step between cycles. Temperatures and the treatment period for the second cycle can be the same as those of the first cycle or different. Additional treatment cycles could also be delivered. In this example, it would not be necessary to move the applicator between cycles, and the cycles could optionally be separated by a tissue rewarming/thaw step. As another alternative, an additional treatment at any given site could be performed later in the patient procedure after an applicator has treated other tissue sites. Still another alternative is that an additional treatment could be delivered during a separate patient procedure performed either later the same day as the first treatment, or the next day or several days or a week later, and the procedure could be repeated on a regular basis if desired (e.g., every day, every other day, every week, every month, etc.). Any number of desired follow-on treatments can be performed to achieve sufficient and desired overall levels of tissue treatment to create a desired tissue response.

The method 140 can be used to perform the treatments disclosed herein, such as the treatments discussed in connection with FIGS. 1 and 2. A freeze event can cause disruption of sebaceous glands to affect sebum production (e.g., decrease or limit sebum production). The period of time of contact (e.g., time of contact between the subject's skin and ice crystals and/or between the subject's skin and the cooling surface of the applicator) can be selected to achieve the desired thermal injury to the sebaceous glands. The systems, components, and acts disclosed herein can be mixed and matched, as discussed in connection with examples 1-4 below.

Example 1

Ice crystals can be formed along an applicator, using temperature programming. Water (e.g., droplets of water, a layer containing water, etc.) can be disposed on the applicator surface (e.g., surface 111 in FIG. 2), and the temperature of the applicator surface can be lowered to about −20° C., −15° C., −12° C., or another suitable temperature for generating one or more ice crystals based on water freezing at or below its melting/freezing temperature of 0° C. In some procedures, the applicator can be prepped to have ice crystals on its exterior surface to cause a skin freeze event to occur once the applicator contacts the skin surface. For example, one or more ice crystals carried by the applicator can physically contact the skin to initiate a freeze event in the skin. In other procedures, the ice crystals can physically contact and trigger a freeze event in a coupling media on the skin surface. When the coupling media freezes, it can cause freezing of the skin surface and subsequent freeze propagation through deeper tissue. In other procedures, the coupling media can be absorbed into the skin, and the absorbed coupling media can freeze to cause freezing of the skin.

Tissue can be slowly or rapidly rewarmed as soon as practicable after a freeze event has occurred to limit, reduce, or prevent damage and adverse side effects associated with the freeze event. After freezing begins, the skin can be slowly or rapidly warmed as soon as possible to minimize or limit damage to the epidermis. In other procedures, the skin is partially or completely frozen for a predetermined period of time and then warmed. According to one embodiment, the applicator 104 of FIG. 2 can warm shallow tissue using, for example, thermoelectric elements in the device 109. Thermoelectric elements can include Peltier devices capable of operating to establish a desired temperature (or temperature profile) along the surface 111. In other embodiments, the applicator 104 has electrodes that output radiofrequency energy for warming tissue.

Absorption enhancers, cryoprotectant agents, INAs, and coupling media can be delivered via liposomes, hydrogels, emulsions, or the like. Absorption enhancers can increase permeation to affect uptake of, for example, water, INAs, cryoprotectants, etc. Skin can be warmed before or during exposure to applied substances to increase uptake into the epidermis, with minimal or limited increased uptake into the dermis due to the dermal-epidermal junction barrier. The characteristics of the tissue can be affected by mechanically altering the subject's skin. These characteristics can include absorption characteristics, thermal characteristics, or the like. For a treatment which does not include freezing and only cooling or supercooling, it is desirable to increase an uptake of a cryoprotectant into the skin to provide maximum protection against the possibility of a non-intended freeze occurring. For a treatment which is to include freezing, it is desirable to increase an uptake of an INA and/or water to increase the possibility of a freeze event being initiated and being initiated at a desired time, and to increase a level of cryoinjury.

Figure 6:
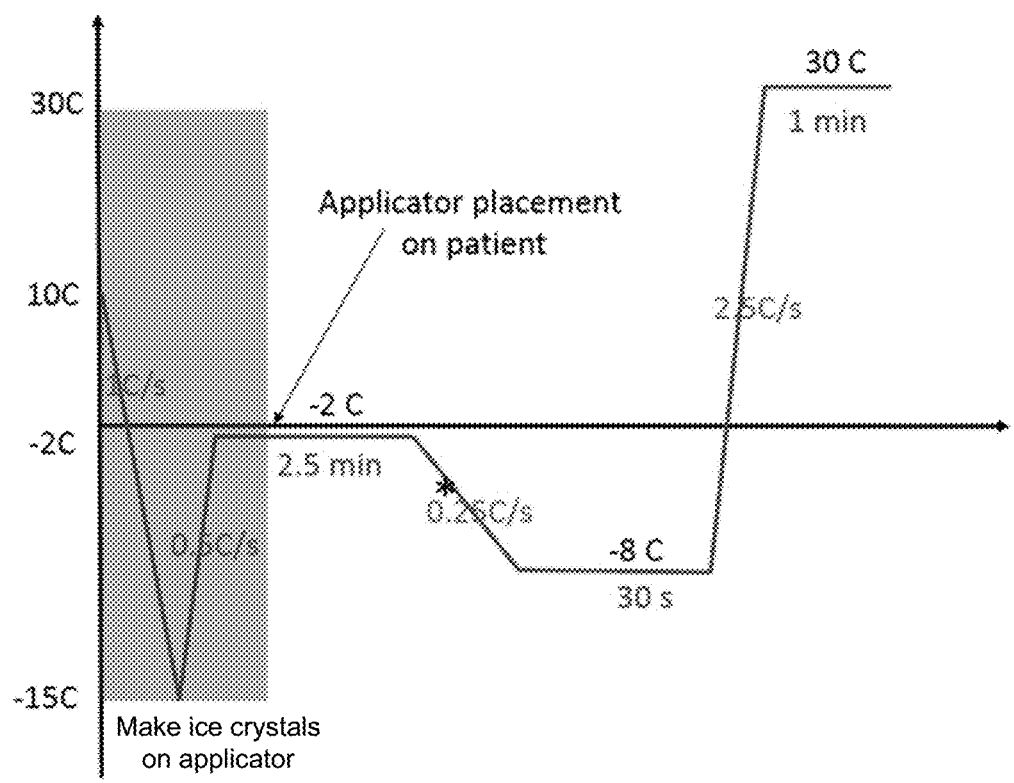
FIG. 6 is a plot of temperature versus time for a treatment involving minimal or no skin supercooling when an applicator is initially placed on a patient's skin to initiate a freeze event.

FIG. 6 is a plot of applicator temperature versus time for a treatment involving minimal or no skin supercooling when an applicator is initially placed on a subject to initiate a freeze event in accordance with an embodiment of the disclosed technology. A freeze event can be initiated upon placement of a frozen applicator surface on the skin. For example, the applicator surface (e.g., surface 111 shown in FIG. 2) can be cooled to a temperature of −15° C. to form ice crystals thereon. After the temperature of the applicator surface is raised at a desired rate to a suitable temperature for placement on the subject, the applicator surface can be applied to the treatment site. For example, the applicator surface can be warmed at a rate of 0.4° C./s, 0.5° C./s, or 0.6° C./s to a temperature of about −4° C., −3° C., −2° C., −1° C., 0° C., etc. The skin surface, targeted tissue, etc. can be maintained at a temperature of about −3° C., −2° C., −1° C., 0° C., or 1° C.

The applicator can be kept in thermal contact with the skin surface for a first treatment period (e.g., 2 minutes, 2.5 minutes, 3 minutes, etc., with 2.5 minutes being shown in FIG. 6) to cool the skin from an initial temperature (e.g., 33° C.) to a lower temperature (e.g., −4° C., −3° C., −2° C., −1° C., 0° C.). The applicator surface can then be lowered at a desired rate to a temperature for inducing a freeze event. The freeze event (indicated by an "*" in FIG. 6) can occur while the applicator surface is cooled at a rate of about 0.2° C./s, 0.25° C./s, 0.3° C./s, or other desired rate. The applicator surface can be held at a temperature of about −8° C. for a second treatment period (e.g., 20 seconds, 30 seconds, 40 seconds, etc.). The skin surface temperature can be slightly higher than the temperature of the applicator surface, so the temperature of the applicator surface can be selected to keep the target tissue frozen for a desired freeze period.

After completion of the freeze period, the applicator and skin temperature can be rapidly raised to a normal temperature, such as room temperature or above. In some procedures, the applicator can be warmed at a rate of about 1° C./s, 2° C./s, 2.5° C./s, 3° C./s, or other rate selected to thaw frozen tissue. FIG. 6 shows the temperature of the applicator raised at a rate of about 2.5° C./s. The thawed tissue can include epidermal tissue, dermal tissue, subcutaneous tissue, and/or other tissue. After the tissue is warmed for a warm period, another cryotherapy procedure can be performed at the same or difference site using the same or different treatment parameters.

Example 2

A substance can be applied to either the skin, the applicator, or both, and can be used to generate ice crystals. The substance can be a coupling media with one or more cryoprotectant agents and can be applied when it is initially at a temperature above its melting point, which can be several degrees below 0° C. and lower than a melting/freezing point of fluid in the skin tissue. The melting/freezing point of the applied substance can be in a therapeutic skin supercool treatment temperature range or other suitable temperature range. After a predetermined amount of skin supercooling has occurred, the temperature of the applied substance can be lowered to a value below its melting point or temperature to create ice crystals therein to initiate the freeze event in the skin.

Cryoprotectant agents can comprise propylene glycol, glycerol, polyethylene glycol, combinations thereof, or other biocompatible agents. In some embodiments, the substance is a cryoprotectant solution with a cryoprotectant agent mixed with water to provide a desired melting/freezing point. The concentration of the cryoprotectant agent can be increased to lower the melting/freezing point of the substance. By controlling a concentration of the cryoprotectant, characteristics of the substance (e.g., melting point, spontaneous freezing point, etc.) can be controlled, thus enabling ice crystal generation at/below any desired temperatures while inhibiting or preventing ice crystal generation at/above certain temperatures. INAs can be incorporated into the substance to, for example, provide predictable initiation of freeze events once the temperature of the substance is lowered below the melting/freezing point of the INA.

Figure 7:
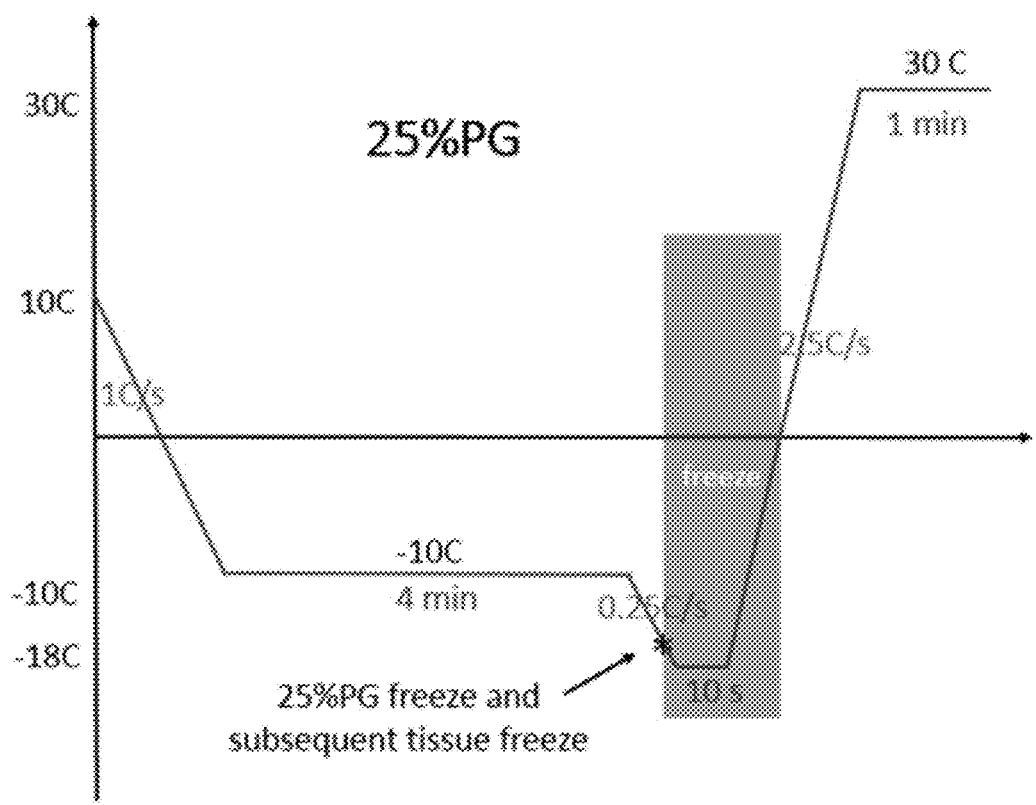
FIG. 7 is a plot of temperature versus time for a treatment involving substantial skin cooling.

FIG. 7 is a plot of applicator temperature versus time for a treatment involving substantial skin cooling in accordance with an embodiment of the disclosed technology. The applicator and skin can be cooled at a desired rate (e.g., 0.5° C./s, 1° C./s, 2° C./s, etc.) to a supercooled temperature (e.g., −8° C., −10° C., −12° C.). A freeze event in the skin can be initiated after a supercooling period of about 3 minutes, 4 minutes, or 5 minutes at the supercooled temperature, illustrated as −10° C. During this period, the skin surface and cooled applicator surface can be at substantially the same temperature. A cryoprotectant coupling media can help limit thermal injuries to non-targeted tissue and can be disposed at the applicator-skin interface. In some embodiments, the cryoprotectant coupling media is about 25% by weight or volume propylene glycol (PG) and about 75% by weight or volume water and has a melting or freezing temperature of about −11° C. The composition of the coupling media can be adjusted to increase or decrease its melting/freezing point. After the supercooling period, a temperature of the applicator is further lowered to initiate a freeze event. FIG. 7 shows initiation of the freeze event in the skin while the applicator and skin surface are cooled from about −10° C. to about −18° C. The level of freeze in the tissue can be maintained while the applicator surface and skin surface are held at a temperature of about −18° C. for 10 seconds prior to rapid rewarming.

Ice crystals can be generated by diluting a precooled coupling media to raise its melting/freezing point. The applied substance can be a 25% by volume PG cryoprotectant solution with a melting temperature of −11° C. Tissue can be supercooled to a desired temperature (e.g., −8° C., −10° C., −12° C., etc.). After the desired amount of supercooling has occurred, the freeze event can be initiated by further lowering the temperature of the applied substance (e.g., "diving" the temperature) to a temperature of about −18° C. so as to freeze the substance. Instead of further lowering the temperature, or "diving," a freeze event can be initiated at a target freeze temperature (e.g., −10° C.) or at a higher temperature by injecting cold water or another substance into the applied substance at a predetermined location to locally dilute the cryoprotectant concentration to a level whereat the melting point of the coupling media is higher than the target freeze temperature. The melting/freezing point of the coupling media can be, for example, close to −1° C., −0.5° C., or 0° C. so that ice crystals form in the diluted substance and initiate a freeze event in the skin. Dilution can be with 100% water, water doped with an INA, or another substance, thereby providing consistent and predictable freezes at temperatures as warm as, for example, −1° C., −2° C., or −3° C. Alternatively, a water and ice mixture or a water, ice, and INA mixture can be injected to provide freezes at about a desired temperature (e.g., −1° C., −0.5° C., etc.). This method can be used in conjunction with substantial skin supercooling to initiate a freeze event at relatively warm temperatures, for example −1° C., −2° C., −3° C., −4° C., or −5° C., by pre-warming the skin after the supercooling period at a lower temperature (e.g., −8° C., −10° C., or −12° C.) has elapsed, which can significantly reduce or prevent harm to non-targeted tissue, such as the epidermis, as compared to a treatment where the freeze event is started at a lower temperature, such as −10° C. or even lower (e.g., −18° C. when "diving" is utilized to initiate the freeze event).

Example 3

Energy can be used to manage ice crystal formation. When aqueous coupling medias are lowered below their melting/freezing points and are in a supercooled state, ultrasound can induce ice crystal formation in the skin and/or a freeze event in the coupling media whether or not the coupling media is only slightly or significantly supercooled. Although delivering ultrasound can obviate INAs, ultrasound and INAs can be used together. Ultrasound has been used to form ice crystal in aqueous coupling agents. For example, a dental cleaning ultrasound probe operated at about 20 kHz and about 25 W forms ice crystals in coupling agents. In another example, a non-dental ultrasound probe operated at about 20 kHz and 1 W forms ice crystals. Ultrasound with other parameters can be selected based on desired ice crystal formation and/or growth.

Example 4

After tissue is in a supercooled state, a freeze event triggering or promoting substance can be injected into or near the target region. The substance can be partially frozen ice or a water slurry solution that generates an immediate freeze event. In some embodiments, the epidermis can be rewarmed to a temperature close to 0° C. prior to the freeze event, and an injection of saline ice water slurry into the dermis can initiate the controlled freeze under the epidermis. Needles, catheters, or injection devices can be introduced into the subject to inject the substance. FIG. 2 shows an optional catheter 149 that can be introduced into the subject. Once an end portion of the catheter 149 is positioned in the skin 10, the catheter 149 can deliver an ice crystal, ice slurry, or suitable substance in the tissue. The catheter 149 can be used to initiate freeze events at any number of treatment sites.

Various combinations of steps in examples 1-4 can be combined. To enhance or maximize freeze injury in the dermis while limiting or minimizing side effects associated with freezing in the epidermis, contact between an ice crystal and the tissue can be delayed until a desired level of skin supercooling is achieved. A volume of target skin can be substantially supercooled and then contacted by ice crystals to maximize freeze injury to the skin while minimizing side effects. A large amount of prior supercooling can maximize an amount of tissue damage that occurs during the initial freeze event, and can allow non-targeted tissue to be rewarmed to inhibit, limit, or substantially prevent thermal injury to that non-targeted tissue. The epidermis can be non-targeted tissue that can be immediately or quickly re-warmed after the freeze event in the targeted tissue, such as the dermis. Warming can limit or minimize an amount of time the epidermis is in a frozen state. This is in contrast to a treatment method whereby little or no supercooling is employed. In this latter case, to obtain a therapeutic level of treatment equivalent to the former case (which utilizes substantial supercooling and substantial fractional freezing during the initial freeze event, since cooling is delivered "top down," via the surface of the skin), the epidermal tissue needs to be maintained in a frozen state longer after the freeze event is initiated, which can exacerbate damage to non-targeted epidermal tissue.

To restrict freezing injury to mostly upper skin layers while significantly sparing deeper tissue from significant injury, ice crystals can contact the skin immediately or very soon after the skin temperature is lowered below the skin's melting/freezing point. Limited superficial epidermal freezes can be achieved with minimal injury to dermal, fat and muscle layers, especially when the duration of the freeze event is kept relatively short. In some facial procedures, the freeze injury can be limited to the skin to avoid any appreciable reduction of subcutaneous tissue or underlying muscle which form a support structure for the skin.

Figure 8:
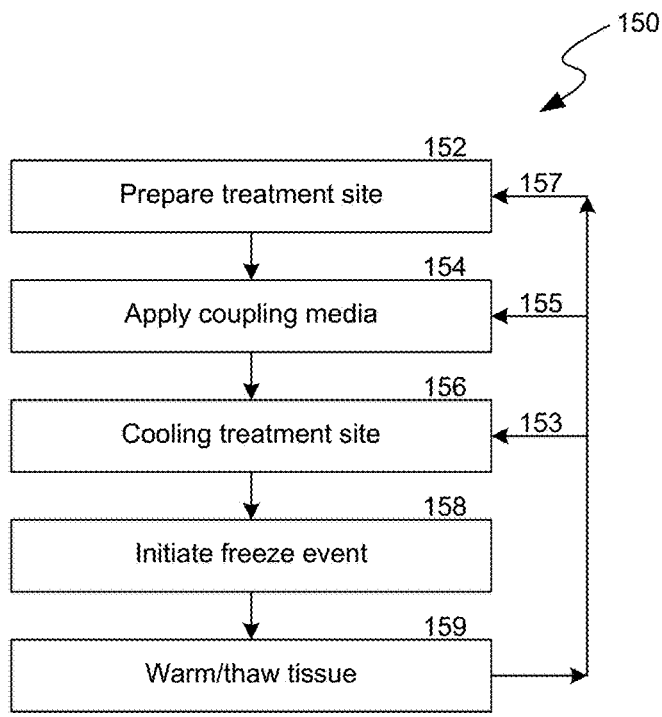
FIG. 8 is a flow diagram illustrating a method for treating a subject's skin in accordance with an embodiment of the technology.

FIG. 8 is a flow diagram illustrating a method 150 for treating a subject's skin in accordance with an embodiment of the technology. Generally, coupling media can be applied to the treatment site. The treatment site can be cooled, and a freeze event can be initiated to at least partially freeze tissue. An early stage of the method 150 can include coupling a heat-exchanging surface of an applicator to the subject's skin. The heat-exchanging surface can be a temperature-controlled surface (see, e.g., surface 111 of FIG. 2) of a heat-exchanging plate with internal thermal elements (e.g., thermoelectric elements, fluid elements, etc.) or external thermal elements (e.g., thermal elements mounted to the backside of the heat-exchanging plate). In some embodiments, the temperature-controlled surface can be an interface layer, a dielectric layer, or the like. Additionally or alternatively, a vacuum or suction force can be used to positively couple the patient's skin to the temperature-controlled surface. Coupling the temperature-controlled surface to the subject's skin can also include providing a substance to the patient's skin as is described herein and in commonly assigned U.S. Patent Publication No. 2007/0255362. Details of the method 150 are discussed below.

At block 152, the treatment site can be prepared by, for example, mechanically, chemically, or otherwise altering the skin. Mechanical alteration can be achieved by brushing or scraping the skin surface intermittently or continuously for a period of time, such as about 30 seconds, 1 minute, 2 minutes, 3 minutes, or a suitable length of time selected based on the desired amount of surface cleaning, permeation, and/or exfoliation (e.g., exfoliation of the stratum corneum). In other embodiments, permeability of the skin can be adjusted by clearing pores in the stratum corneum, producing and/growing vacuoles (e.g., vacuoles in the epidermis below the stratum corneum), combinations thereof, or the like. In some treatments, an adhesive strip can be applied to and removed from the skin to remove uppermost layers of the epidermis, clean the treatment site, increase permeability of the skin, or otherwise prepare the treatment site. The uppermost layers of the epidermis are dryer than lower layers, so when the uppermost layers are removed, the exposed lower layers have greater water content so they are more susceptive to being frozen during a procedure designed to freeze tissue, especially when an INA is used to facilitate the freeze. Permeability of the skin can also be increased by using microneedling whereby a plurality of microscopic holes are formed in the skin to create pathways for absorption of a coupling media. Alternatively, sonophoresis can be used whereby ultrasound waves are used to stimulate microvibrations within the skin to increase the overall kinetic energy of molecules making up the coupling media or topical agent to be delivered into the skin to increase absorption. Some preferred frequencies are 20-40 kHz, or more than 1 MHz. Other frequencies could be used. Alternatively, increased absorption can be achieved using iontophoresis techniques for increasing absorption using, for example, electric fields to push topical agents into the skin. A permeability coefficient of coupling media for passing through tissue (e.g., epidermal tissue) can be increased at least about 10%, 20%, 30%, 40%, 50%, 60%, 70%, 80%, 90%, or 95% to achieve desired absorption rates using any one or more of the above described techniques. Other techniques can be used to facilitate delivery of coupling media or substances. Different testing techniques (e.g., static cell techniques, flow-through diffusion techniques, etc.), algorithms, and modeling can be used to determine the permeability coefficient and can be used to determine flux, including a steady state flux.

At block 154, coupling media can be applied to the skin. The coupling media can include, without limitation, water, hydrogels, cryoprotectants, emulsions, combinations thereof, or the like before preparing the treatment. Applying the coupling media may include placing, spraying, coating, or rubbing a liquid, gel, or sheet coupling media onto the skin using an instrument including, for example, a brush, a spatula, a spray bottle or a syringe, or by hand (e.g., an operator's gloved hand).

The coupling media can include one or more temperature depressants, INAs, etc. The temperature depressants can include, without limitation, polypropylene glycol (PPG), polyethylene glycol (PEG), propylene glycol, ethylene glycol, glycerol, dimethyl sulfoxide (DMSO), or other glycols. The temperature depressants may also include ethanol, propanol, isopropanol, butanol, and/or other suitable alcohol compounds that may lower the freezing point of a solution (e.g., body fluid) to about 0° C. to −40° C., and more preferably to about −10° C. to −16° C. Certain temperature depressants (e.g., PPG, PEG, etc.) may also be used to improve smoothness and to provide lubrication. Additionally or alternatively, the coupling media can include one or more thickening agents, pH buffers, humectants, surfactants, and/or additives.

At block 156, the subject's skin can be cooled. An applicator can be applied to the treatment site to place the applicator in thermal contact with target tissue. Tissue can be supercooled and then frozen, to limit or prevent unwanted side effects. The surface of a human subject's skin can be cooled to a temperature no lower than −40° C. to avoid unwanted skin damage. The surface of the skin can be heated to bring shallow non-targeted tissue out of the supercooled state while the deeper targeted region remains in the supercooled state.

At block 158, the supercooled targeted region can be nucleated to produce freezing that can destroy or damage targeted cells, for example, due to crystallization of intracellular and/or extracellular fluids. A catalyst for nucleation (e.g., mechanical perturbations, RF energy, alternating electric fields, etc.) can be provided following a protective increase of a temperature of non-targeted epidermal layers. The mechanical perturbations can be vibrations, ultrasound pulses, and/or changes in pressure. Non-targeted layers of tissue can be warmed enough to avoid freezing upon nucleation of targeted tissue. The treatment systems disclosed herein can utilize applicators disclosed herein to perform such supercooling methods.

Some treatments include freezing dermal tissue more times than adjacent epidermal tissue. At block 156, dermal and epidermal tissue can be cooled and frozen (block 158). The skin can be warmed by an applicator (which is at a temperature slightly below 0° C.) an amount sufficient to allow the dermal tissue to thaw due to internal body heat but not the epidermal tissue which is further removed from blood flow than is dermal tissue. After thawing the dermal tissue, block 158 can be repeated by chilling, for example, the skin to refreeze the dermal tissue while the epidermal tissue remains frozen. A desired level of damage to the dermal tissue can be achieved by repeatedly freezing and thawing the dermal layer, because the primary mechanism of damage during freezing is caused by ice crystal nucleation and growth.

Some treatments include a warm/thaw step 159 following the freeze event(s) whereby the frozen and cooled tissue is rewarmed either passively or actively by the applicator. After the warm/thaw step 159, the cooling 156 and freezing 158 steps can immediately be repeated, as shown by arrow 153, any number of times, such as 1, 2, 3, 4 or more times, preferably during the same patient treatment and optionally without moving the applicator. Alternatively, the cooling 156 and freezing 158 steps can be repeated during the same patient treatment but after the applicator has been moved to another treatment site and then brought back to the original treatment site, or during a separate patient treatment session either later in the day of the first treatment or the next day or several days later. Any number of repeat sessions can be employed to achieve an overall desired level of treatment. Arrows 157 and 155 show possibilities for the retreatment which can include a repeat of the skin preparation step 152 and/or a repeat of the applying coupling media step 154, as desired.

FIGS. 9A-9C show stages of a method for preparing a treatment site in accordance with an embodiment of the disclosed technology. Generally, the subject's skin can be mechanically altered to facilitate absorption of coupling media. For example, stripping elements can be applied to and removed from the skin surface any number of times to remove an upper portion of the epidermis so as to expose lower layers of tissue. The lower layers can have a relatively high water content and thus may be better able to absorb and uptake various agents, including water or oil based coupling media, into the epidermis.

FIG. 9A is a cross-sectional view of a stripping element 200 applied to the skin surface and overlaying a pore. The stripping element 200 can be an adhesive strip (e.g., adhesive tape) or another adhesive element that can be pulled off the skin to remove, for example, sebum, hair follicles, or features from the pilosebaceous unit to expose the skin pore for uptake of applied substances. The stripping element 200 may be a single adhesive strip (e.g., piece of adhesive tape) that is cut to overlay the entire treatment area. In other embodiments, multiple stripping elements 200 are applied to the treatment site. The adhesive characteristics of the stripping elements can be selected based on the desired amount of mechanical alteration to the skin and desired patient comfort.

FIG. 9B is a cross-sectional view of the stripping element 200 being removed from the skin to remove material 201 from a pore 203 to open or unclog a pore entrance 202. Additionally stripping elements can be reapplied any number of times to further unclog the pore 203 or otherwise prepare the treatment site.

FIG. 9C is a cross-sectional view of a treatment site after the pore 203 has been cleared and a substance 205 has been applied. The substance 205 can infuse the pore 203 and can be absorbed by the skin. Water can be part of the substance, and a subsequent freeze event can cause the water in the skin pore to freeze and cause additional tissue damage.

Skin can be mechanically stimulated before, during, and/or after any steps in the method 140 (FIG. 5) or 150 (FIG. 8). Mechanical stimulation can include, for example, stimulation or agitation by brushing, rubbing, applying ultrasound, dermabrasion, or other means which can clean the treatment site and/or cause the barrier of the stratum corneum (i.e., the outermost layer of the epidermis consisting of dead cells) to be temporarily reduced and/or increase movement (e.g., turbulence) of the coupling media with respect to the skin. Without being bound by theory, it is believed that mechanical stimulation of the skin (e.g., agitation of, reduction of, or penetration of the stratum corneum) can enhance the permeation of the coupling media into the underlying epidermal layer, dermal layer, or another layer of tissue. In one embodiment, the skin can be mechanically stimulated for about 20 seconds to about 10 minutes. In another embodiment, mechanical stimulation can be applied to the treatment site for about 20 seconds, about 40 seconds, about 1 minute, about 2 minutes, about 5 minutes or greater than about 5 minutes. In some embodiments, mechanical stimulation could be performed with, for example, a dermal agitation brush, a brush having rotating bristles, or the like. Brushing or rubbing the skin can include, in some embodiments, moving across the skin at the treatment site in a circular or back-and-forth motion or, in other embodiments, in linear strokes, for increasing the skin permeability for the substance. The permeation rate can be increased or decreased to achieve a desired amount of absorption.

Different techniques can be used to evaluate the permeability of the skin before and/or after performing the stripping process. In one procedure, the coupling agent can be applied to the treatment site and then cells at the treatment site can be progressively removed by repeatedly applying the stripping element or by applying a series of stripping elements. The stripping elements and treatment site can be evaluated to determine the volume of the coupling media absorbed by the skin.

D. Substances for Treatments

Because ice crystals can be reliably generated to trigger on-command freeze events, a substance can be used to improve thermal coupling between a skin surface and a cooling applicator. In some embodiments, the substance is an aqueous solution coupling agent, which contains a cryoprotectant agent. Further substances can contain water and a medium for promoting an on-demand reliable creation of an ice crystal when initiation of freezing in the treatment is desired. Liquid water has clusters of molecules that are undergoing constant collisions with other molecules and clusters, sometimes breaking apart and sometimes forming new clusters. When water is being cooled, as the temperature drops and the thermal movement of water molecules decreases, the tendency of water molecules to aggregate becomes stronger and the likelihood that a critically large cluster of molecules will form increases rapidly. Ice nucleation is catalyzed upon formation of a critically large cluster of molecules. Consequently, initiation of freeze or ice nucleation in a sample of water (or a coupling agent) takes place from a nucleus with an ice-like structure. The nucleus can promote the organization of water molecules into an ice crystal lattice.

Water and aqueous coupling agents have a natural tendency to cool to a temperature significantly below their equilibrium freezing point before ice nucleation; that is, they have a tendency to supercool. There are two modes of ice nucleation of water: homogenous and heterogeneous. When a critically large nucleus is formed by spontaneous aggregation of the water molecules themselves, the nucleation is referred to as "homogeneous." For a macroscopic quantity of water, the size of a cluster needed for ice nucleation is often about 25 molecules. The radius of the cluster can be about 3 molecules. The critical radius that coincides with this size gives a temperature of −41° C., which is called the homogeneous nucleation temperature for water. Accordingly, the homogeneous nucleation temperature for water is the minimum temperature that pure water can be cooled to before freezing occurs spontaneously.

When aggregation of water molecules is catalyzed by an external source, the nucleation is referred to as "heterogeneous." The cause of external nucleation can be the introduction of ice crystals or another external substance into the supercooled sample. For example, crystallization can be triggered by the physical introduction of a nucleation initiator (e.g., a seed crystal or nucleus) around which a crystal structure can form to create a solid.

The substances can be hydrogels, liposomes, or emulsions, such as oil-in-water (O/W) emulsions, water-in-oil (W/O) emulsions, oil-in-oil (O/O) emulsions, or nano-emulsions, and can provide homogeneous or heterogeneous nucleation.

1. Nucleation Initiators

An INA can be a substance that promotes the formation of a seed crystal (or initial cluster), thus catalyzing a heterogeneous ice nucleation. When INAs are used, water freezing takes place at a temperature higher than would be required in the case of a homogeneous nucleation, and the largest biological ice nucleators may trigger freezing at −1° C. to −5° C. or other lower temperatures, long before a spontaneous water freeze would normally otherwise occur. Spontaneous water freezes can variably occur at −10° C., −15° C., −20° C., or −25° C. or lower, and the timing of the spontaneous freezes is very unpredictable. Example INAs include biogenic-derived proteins, materials derived from a Gram-negative epiphytic bacteria, and/or materials belonging to the genus *Pseudomonas, Erwinia*, or *Xanthomonas*. For example, INAs may be inorganic- or organic-derived substances that promote heterogeneous ice nucleation. Embodiments of the present technology can include methods of producing controlled and predictable freezes of the skin and subcutaneous tissue using INAs.

In general, INAs can promote the formation of ice crystals in water-like substances at a specific temperature, such as generally a few degrees below 0° C. INAs can be used synergistically with a selected temperature treatment protocol to control the onset and extent of a freeze event during cryotherapy and can be used to promote in-vivo freezing at higher temperatures than a natural homogeneous nucleation freezing point of skin tissue. An aspect of some embodiments of the present technology relates to methods of producing a controlled freeze of the skin and subcutaneous tissue using INAs. Cooling methods using INAs permit the triggering of ice nucleation at specific temperatures, such as temperatures close to 0° C. Thus, INAs may provide an advantage in therapies that require freezing and variable treatment temperatures with desired therapeutic treatment/safe temperature ranges and that create a precise and controllable extent of skin and tissue damage from a freeze event.

Various Gram-negative epiphytic bacteria have been known to produce INAs. These belong to the genera *Pseudomonas, Erwinia* and *Xanthomonas*, among others. One of the highest level of ice nucleation activators is an ice nucleation protein (INP) from some ice-nucleating bacteria. Protein molecules and materials located on the outer membrane of these bacteria are responsible for the ice nucleation. Cells can also be lysed or otherwise produce pieces of cellular material (e.g., membranes) in which such INAs are found or trapped, for example, *Pseudomonas syringae*.

One commercially accessible INA is SNOMAX® available from Snomax LLC, Englewood, Colo., which is derived from the bacterium *Pseudomonas syringae* (freeze-dried protein powder). This protein initiates a freezing process by serving as an ice nucleator and raises the predictable freezing temperature of water to about −3° C. SNOMAX® is used widely for snowmaking and is safe for human use and non-pathogenic. SNOMAX® can be a powder that exhibits $10^{12}$ to $10^{13}$ ice nuclei per gram at temperatures less than about −4° C. Coupling agents prepared with SNOMAX® or other substances derived from the bacterium *Pseudomonas syringae* can have enough INAs to produce reliable ice nucleation at desired temperatures. Bacteria/cell concentration has a direct effect on the nucleation temperature of water. INAs can be used in standard powder form, and can be used as ice nucleators with or without added water. In some embodiments, INAs can be fractionally delivered to skin, such as by microneedles (e.g., an array of microneedles). Biocompatible INAs can be invasively delivered using needles, such as intradermal needles. Additionally or alternatively, INAs can also be used with non-contact cooling devices, such as cooling/freezing sprays.

INAs can be used in cooling protocols to cause ice nucleation at temperatures about −2° C., −3° C., or −4° C. At these temperatures, damage to epidermal tissue can be significantly less than damage typically produced at lower freezing temperatures. The temperature for ice nucleation can be selected to be high enough to avoid significant skin pigmentation changes associated with freeze events.

A non-invasive applicator (e.g., applicator 104 of FIGS. 2 and 3) can be used to control skin cooling and can include one or more temperature sensors. Temperature sensors (e.g., element 167 in FIG. 2) can be embedded along the treatment surface of the applicator and can be used as part of a temperature control system. The temperature control system can include one or more feedback control algorithms to control the applicator based on a predetermined set of temperature values over one or more predetermined periods of time, and have predetermined rates of change when transitioning from one temperature to another temperature, and so on. Different feedback control algorithms can be used to treat tissue using different treatment temperature protocols (and create different temperature treatment cycles) by varying cooling/thawing rates, predetermining therapeutic treatment temperatures, and/or selecting treatment durations. The methods described herein can involve using both INAs to control freezing and varying treatment temperature protocols and profiles.

2. Hydrogel Materials

An aspect of the present technology relates to methods of using hydrogel substances with freezing point depressants (cryoprotectants) and/or INAs for creating a controlled "on command" predictable freeze. Hydrogel substances are a class of crosslinked polymers that, due to their hydrophilic nature, can absorb large quantities of water. Hydrogel substances can have a suitable water content for controlling freezing, including controlling ice nucleation, ice crystallization, freeze propagation, or the like. Integral parts of the hydrogel synthesis include a monomer, an initiator, and a crosslinker. Hydrogel properties can be modulated by varying their synthetic factors, such as reaction temperature, monomer type, monomer crosslinker, crosslinker-to-monomer ratio, monomer concentration, and type and amount of initiator. The composition of hydrogels can be selected for a specific application by selecting proper starting materials and processing techniques.

Hydrogels can be mixed with one or more freezing point depressants and can be engineered to have desired melting/freezing temperatures (e.g., optimum melting temperatures). The freezing point depressants can inoculate tissue. Additionally or alternatively, hydrogels can be combined with INAs that have a set activation temperature to make the hydrogels able to freeze consistently at predetermined temperature ranges (or a specific temperature) different from those associated with hydrogels without ice nucleating agents. The combination of hydrogels, freezing point depressants, and/or INAs can result in a controllable freeze at desired temperatures, such as −3° C., −2° C., −1° C., or other temperatures. Temperatures close to 0° C. can be less damaging to epidermal tissue and are well suited for less aggressive temperature freezing protocols, so temperatures can be selected to protect one or more upper layers of the skin to eliminate or minimize any substantial discoloration side effects associated with freezing skin treatments and to eliminate any permanent adverse events.

The water accommodated by the hydrogel structure can be classified in four types: free, interstitial, bound, and semi-bound water. Free water is located in the outermost layer and can be easily removed from hydrogels under mild conditions. Interstitial water is not attached to the hydrogel network but is physically trapped between the hydrated polymer chains. Bound water is directly attached to the polymer chain through hydration of the functional groups or ions. The bound water remains as an integral part of the hydrogel structure and can be separated only at very high temperatures. Semi-bound water has intermediate properties of bound water and free water. The free and interstitial water can be removed from the hydrogels by centrifugation and mechanical compression.

Controlled freeze techniques can take advantage of the water composition of hydrogels. Hydrogels can be designed to have a specific freezing point or specific freezing temperature range by having a specific ratio of water-monomer-crosslinker content. Cryoprotectant additives, such as glycols (e.g., PG) or other substances, can be used as well to lower their freezing point.

A hydrogel can act as an initiator of a predictable freeze event. As the hydrogel freezes, the hydrogel provides "initial seeds" or crystal sites to inoculate tissue and thus catalyze a controlled predictable freeze at a specific temperature in the skin. In some embodiments, a predictable freeze event can be freezing of tissue that occurs at least 90%, 95%, or 98% of the time when freezing is desired. A predictable controlled freeze event in a hydrogel can also be achieved by precooling the hydrogel to a temperature below its melting point.

The freeze event can be initiated by injecting a nucleation initiator (e.g., ice/water slurry) into the hydrogel to create freezing that reaches the surface of the hydrogel adjacent the patient, which causes freezing of the subject's skin. In other procedures, ultrasound or other nucleation energy can be used to produce a freeze event in the hydrogel. According to one embodiment, additives (e.g., cryoprotectants and/or INAs) can be embedded in isolated layers within an interior of the hydrogel so that these substances are not on an exterior surface of the hydrogel sheet or hydrogel pad and hence do not come in direct contact with skin or other tissue being treated. Encapsulating these substances within the hydrogel obviates the need to choose INA substances that have been tested and validated to be safe when in contact with skin or tissue. Predictable hydrogel freezes can be enhanced by additives, such as INAs.

Figure 10A:
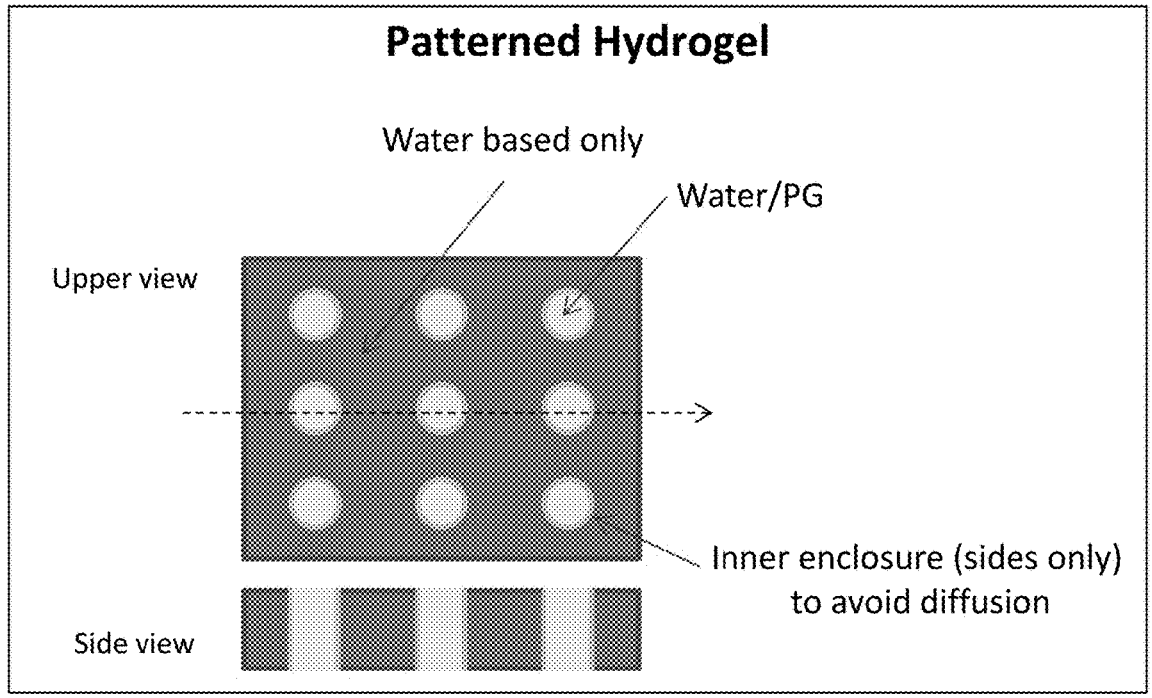
FIG. 10A shows patterned hydrogel suitable for cryotherapy in accordance with an embodiment of the disclosed technology.
Figure 10B:
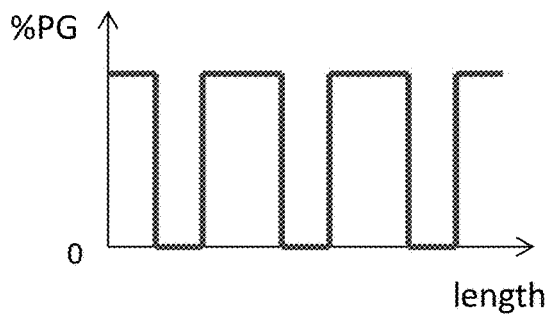
FIGS. 10B and 10C are plots of propylene glycol concentration versus length for patterned hydrogels.
Figure 10C:
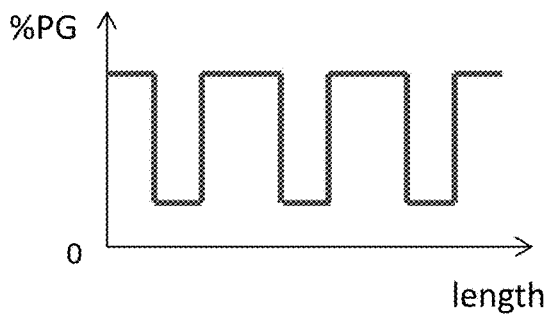

FIG. 10A shows a patterned hydrogel in accordance with an embodiment of the disclosed technology. FIGS. 10B and 10C are plots of PG concentration (% PG) versus length for patterned hydrogels. Hydrogels can include a dispersion medium of water and volumes of nucleation inhibitors (e.g., particles or columns of water/PG emulsion). FIG. 10A shows isolated volumes of nucleation inhibitors spaced apart within a volume of water. In some embodiments, a hydrogel layer or sheet can contain columns of a nucleation inhibiting emulsion separated by a volume of water with substantially no PG. The water surrounding the columns can serve as ice nucleation sites. The inner enclosures (e.g., encapsulants) can inhibit or prevent diffusion of the water/PG emulsion. The composition of the inner enclosure can be selected based on the composition of the enclosed substance, and the pattern, number, and sizes of the localized nucleation inhibiting volumes can be selected based on the hydrogel characteristics.

FIGS. 10B and 10C show embodiments with propylene glycol (PG) located throughout the hydrogel, with the concentration of the PG varying along the length and width of a layer or a sheet of hydrogel. Regions of the hydrogel having the lowest concentration of PG have the highest melting/freezing point and can thus function as ice nucleating regions. Isolated freezing zones can be formed in the skin adjacent to those ice nucleating regions. Other types of cryoprotectant agents or components can replace PG. For example, PG can be replaced or combined with PPG, PEG, DMSO, or the like.

A further embodiment is a hydrogel that contains an INA placed uniformly throughout areas where it is desired to seed freeze propagation. Further, the INA can be dispersed exclusively within interior portions of a volume of hydrogel. For example, the INA can be within a hydrogel sheet so that the INA does not extend to a surface of the sheet, thereby preventing contact between the INA and the skin. The INA can seed a freeze event in an interior region of the hydrogel, and the freeze event can rapidly propagate to an outer surface of the hydrogel, which in turn contacts the skin and causes a freeze event in the skin.

Figure 11A:
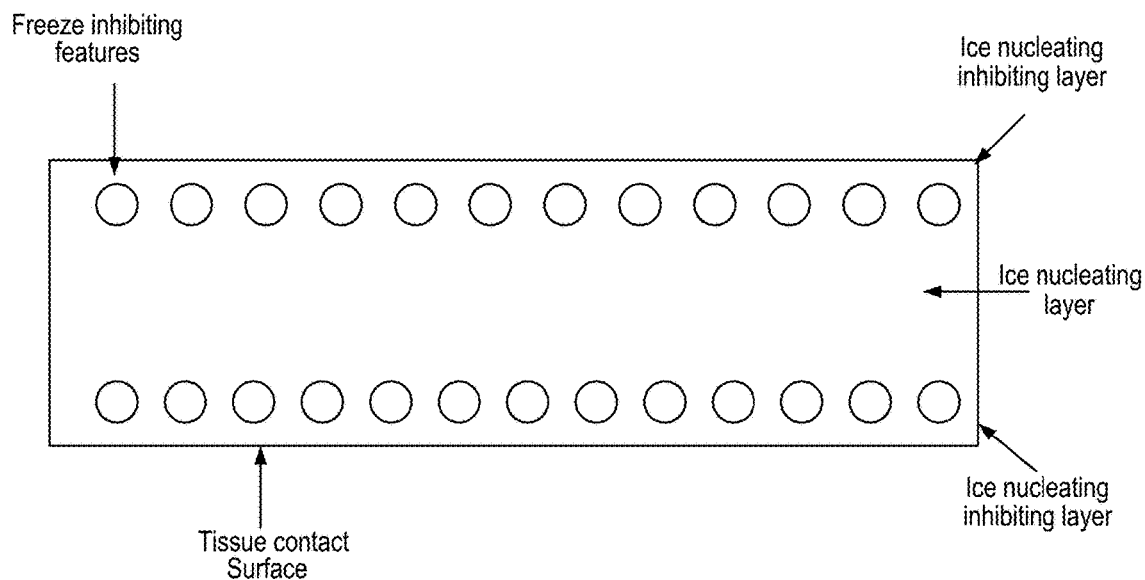
FIGS. 11A and 11B are side views of hydrogel substances with ice nucleating regions in accordance with embodiments of the technology.
Figure 11B:
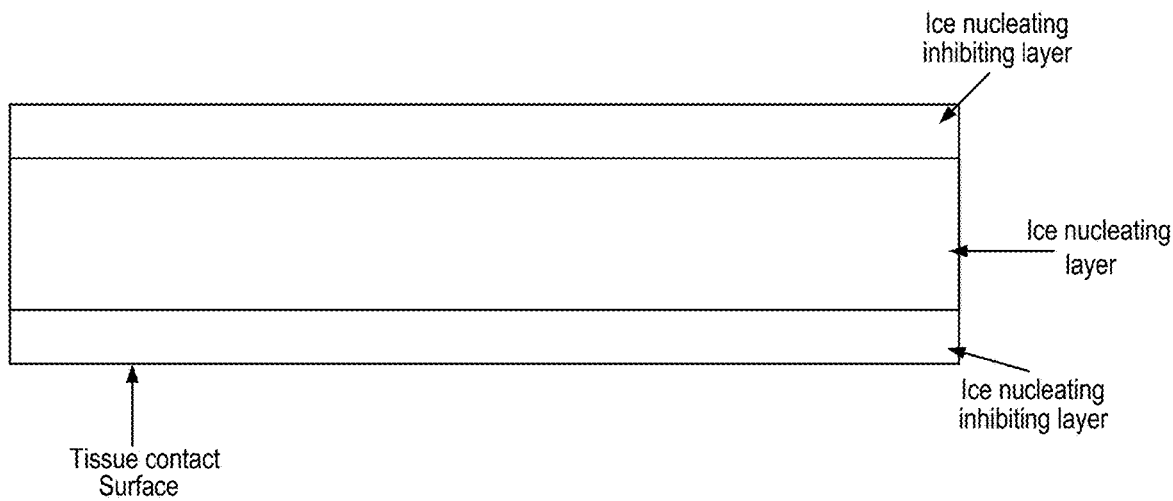

FIGS. 11A and 11B are side views of hydrogels with ice nucleating regions. FIG. 11A shows a hydrogel material with an interior ice nucleating region between upper and lower ice nucleating inhibiting regions. The ice nucleating region can comprise an INA and can have a relatively low concentration of temperature depressant, if any. In one embodiment, the ice nucleating region can be substantially free of temperature depressants and can comprise water and ice nucleating features (e.g., INAs, ice nucleating particles, or the like). The ice nucleating region can be a layer, either a continuous layer or as spots on an interior layer so as to be totally embedded within the hydrogel.

The ice nucleating inhibiting regions can have a melting/freezing point lower than the ice nucleating region and can include volumes of temperature depressants, such as evenly or unevenly spaced apart volumes of PG. The pattern, number, and composition of freeze inhibiting features can be selected based on the desired nucleation inhibiting characteristics.

FIG. 11B shows a multilayer hydrogel material with outer ice nucleating inhibiting layers and an inner ice nucleating layer. The outer ice nucleating inhibiting layers can include temperature depressants, and the inner layer can comprise a high centration of INA (e.g., mostly INA by volume). For example, the outer ice nucleating inhibiting layers can be a layer of a PG solution or a layer with a dense array of PG volumes, and the inner layer can comprise mostly or entirely water. A freeze event can be initiated in the ice nucleating layer and then spread through the outer ice nucleating inhibiting layers.

The hydrogel can be sticky on both a patient side and an applicator side. Sticky upper and lower surfaces can help maintain contact with the subject's skin and applicator and, in some embodiments, help to minimize or limit movement of the hydrogel during treatment. A liner can be used to prevent contamination of the hydrogel. A side of the hydrogel that contacts a liner can be sticky. In some embodiments, the hydrogel can be a sheet with a uniform or variable thickness with adhesive applied to one or more of its outer surfaces.

Hydrogels can be used in the methods discussed in connection with FIGS. 5, 8, and 9A-9C. For example, at block 142 in FIG. 5, a hydrogel can be applied to the subject's skin and can include an INA capable of forming ice crystals in the presence of water. The INA can be encapsulated within a polymer structure of the hydrogel such that the INA does not come in direct contact with the skin as discussed in connection with FIGS. 11A and 11B. The hydrogel and skin can be cooled to arrive at a suitable cooling temperature for freezing the skin. The hydrogel can include a freezing point depressant such that a first melting/freezing temperature of the hydrogel is lower than a second melting/freezing temperature of fluid in the skin.

At block 144 in FIG. 5, skin can be cooled to a temperature above the first freezing temperature and below the second freezing temperature so as to supercool the skin, and after a predetermined amount of supercooling has occurred, the skin is frozen at block 146. The temperature of the epidermis can be raised above the first temperature prior to freezing the dermis.

Referring to the method 150 in FIG. 8, a hydrogel substance comprising a crosslinked polymer and an INA can be applied at block 154. The INA can be embedded within a polymer structure to prevent direct contact between the INA and the skin. In some embodiments, a sheet of hydrogel can be applied to the subject's skin. Alternatively, hydrogel can be injected into the skin. Other techniques can be used to apply hydrogels, which can be creams, gels, etc. At block 156, the skin is cooled. At block 158, the freeze event can be initiated using one or more ice crystals. In other embodiments, energy is used to break the structures containing INAs to release a sufficient amount of the INA to produce a freeze event.

3. Liposomes

Liposomal transport of substances into tissue can be used to deliver substances to specific tissue in a more effective manner than by just applying the substances to a surface of the skin. Because a liposome is lipophilic, it can be absorbed at least into the stratum corneum and can then release a substance within the liposome at a specific location or depth in the subject's tissue. Liposomes can trap water in significant "buckets" that enhance the water content of skin when the liposome breaks down, and make freeze protection more predictable when used with significant amounts of cryoprotectant in the water in the liposome. Liposome skin hydration can be more effective than directly applying water to a skin surface since the stratum corneum is normally hydrophobic.

A topically applied liposome can enhance thermal contact between the applicator/skin and can provide controlled delivery of agents (e.g., cryoprotectant, INAs, etc.), and the liposomes can penetrate the stratum corneum better than either water or water mixed with a cryoprotectant. Additionally, liposomes can deliver different agents to different locations, thus allowing direct transfer of agents to specific targeted cells. In one embodiment, the liposome contains a cryoprotectant (e.g., propylene glycol) and can break down to release the cryoprotectant. In another embodiment, the liposome selectively releases an INA to provide controlled freezing capability through specific tissue.

According to embodiments where freezing is desired, substances (e.g., INAs, cryoprotectant, etc.) can be incorporated into liposomes such that the liposomes can controllably release the substances into the skin. Specifically, liposomes can be formulated to maintain their structure when penetrating the skin to minimize, limit, or substantially prevent release of substances. When enough liposomes accumulate in a certain desired tissue or layer of the skin, an "on-command" breakdown of the liposomes can be initiated to trigger a burst release of the embedded agents. In some embodiments, the liposome can contain an INA for initiating freeze events. Triggering methods for breaking down liposomes include using temperature (e.g., temperature cycling), ultrasound, or a cleansing agent to disrupt or break lipid encapsulation of the liposomes. An applicator can include heaters for heating the treatment site to cause release of the agents, can include transducers for delivering mechanical energy in the form of ultrasound waves, or can include other elements for disrupting liposomes to perform the methods discussed in connection with FIGS. 5 and 8.

Liposomes can have compositions selected based on, for example, a rate of agent release, stability, and/or other desired characteristics. In some embodiments, the rate of agent release can be increased by applying energy, such as ultrasound, heat, or other energy suitable for breaking down lipids that entrap agents. For example, a media can include first liposomes for delivering cryoprotectants to the epidermis and second liposomes for delivering INAs to the dermis. Once the first liposomes are absorbed by the epidermis, they can release the cryoprotectant to protect the epidermis. After the second liposomes have passed through the epidermis and been absorbed by the dermis, they release the INA into the dermal tissue. Upon cooling the treatment site to a temperature below a melting/freezing point of the skin, the INA can cause a predictable freeze in the dermal tissue. Accordingly, each agent can be delivered to specific locations using liposomes. Liposomal medias can be used before, during, and/or after a treatment session. In some procedures, a topical media is applied to the skin surface to deliver cryoprotectant to shallow tissue before cooling. Another media (e.g., media with an INA) can be injected into deeper tissue once the tissue is cooled and is ready for freezing.

4. Emulsions

Emulsions are a class of disperse systems comprising two immiscible liquids and can contain liquid droplets, which comprise the disperse phase, dispersed in a liquid medium, which is the continuous phase. Emulsions can be oil-in-water (O/W) emulsions, water-in-oil (W/O) emulsions, oil-in-oil (O/O) emulsions, or nano-emulsions. Nano-emulsions are desirable since they can penetrate the epidermis and dermis along hair follicle apertures and skin pore apertures. FIG. 12A shows an emulsifier or surfactant with a hydrophilic head and a hydrophobic tail. FIG. 12B shows an agent (e.g., oil-based agent) entrapped by the emulsifiers to separate the agent and water. FIGS. 13A and 13B show oil-in-water and water-in-oil emulsions. Referring to FIG. 13A, the emulsion includes oil droplets that can comprise the same or different agents. In a single-agent emulsion, each droplet can comprise the same agent. In a multi-agent emulsion, different agents (e.g., dispersed mediums) can be evenly or unevenly dispersed in the dispersion medium. The dispersed medium can include droplets containing one or more cryoprotectants, INAs, analgesics, agents, or the like.

FIG. 14 is a table with melting/freezing point temperatures for fats. The fats can be natural oils suitable for O/W emulsions and can have relatively high melting points. For example, fats can have melting/freeze points above 0° C. and can be used in emulsions.

E. Tests and Methods of Treatment

Ex-vivo bench tests with skin using treatment cycles show the unpredictability of supercooling skin and precise control freezing with INAs. In one test, a thermocouple was placed between a coupling layer (coupling media) and skin to detect freezing. A coupling layer of only water was tested to confirm there is no freezing of tissue without an INA. Thermocouple temperature data of five tests, including two water-only tests (where no freezes occurred) and three tests using an INA (where three separate freezes occurred), were conducted to show the effects of INAs and the feasibility of the controlled freeze concept.

Figure 15A:
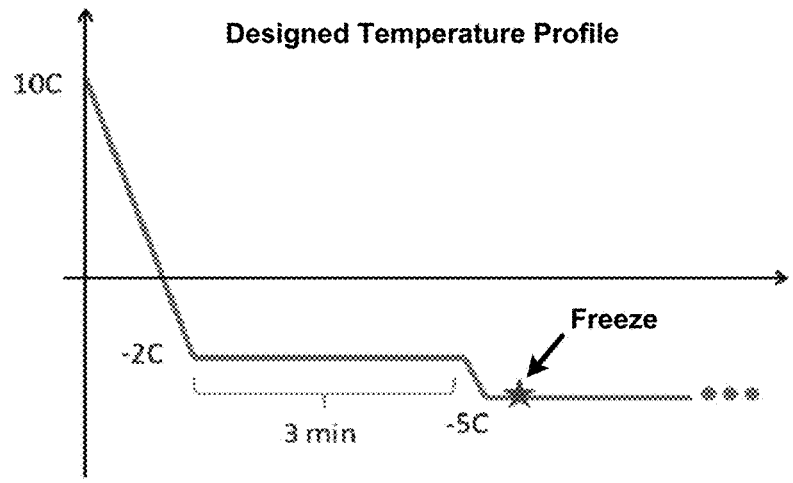
FIGS. 15A and 15B show test results performed on skin in accordance with some embodiments of the disclosed technology.
Figure 15B:
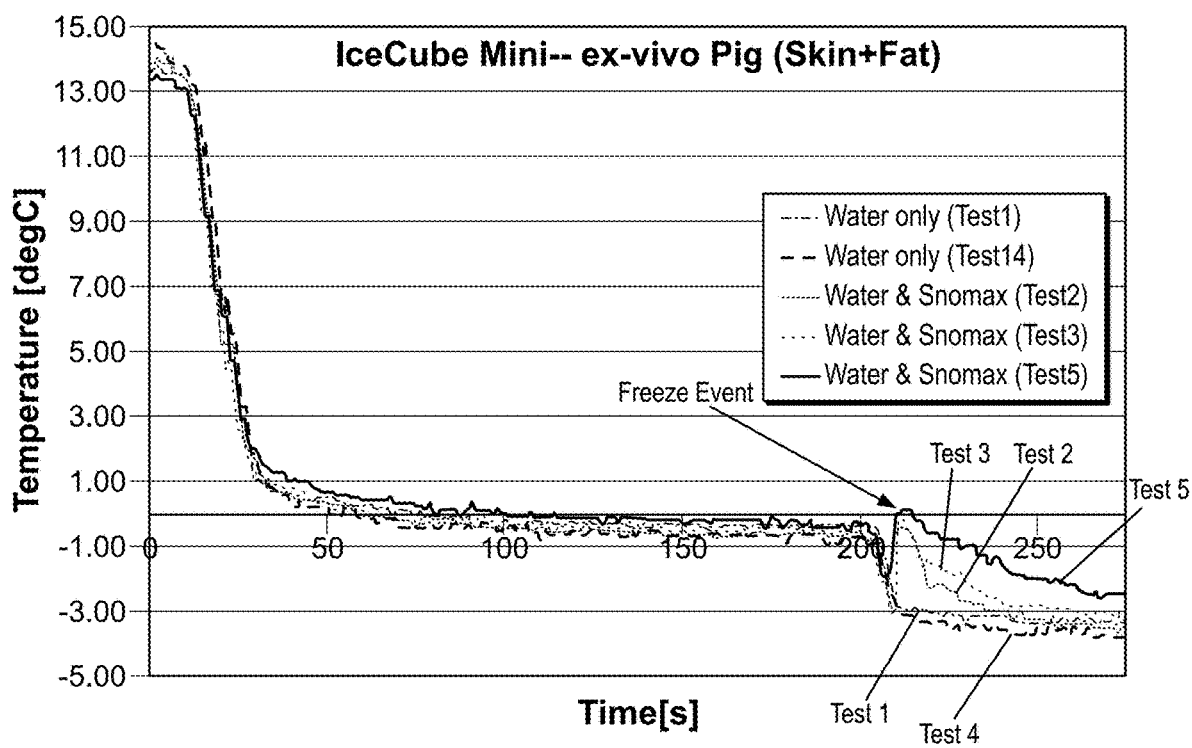

FIGS. 15A and 15B show the results of the tests: with INAs the skin was consistently predictably inoculated and frozen three separate times, whereas without INAs the skin tended to merely supercool and not freeze the two separate times an INA was not used. FIG. 15A shows an example treatment profile designed to supercool at −2° C. for 3 minutes and to trigger freezing at −5° C. FIG. 15B shows three tests with INAs and freeze events occurring shortly after 200 seconds and the associated temperature increase caused by the heat of fusion, which causes the measured temperature to increase from about −1° C. to about 0° C. A non-invasive surface cooling apparatus was used to perform the tests discussed in connection with FIGS. 15A and 15B, and the INA was a SNOMAX®/water solution.

Figure 16:
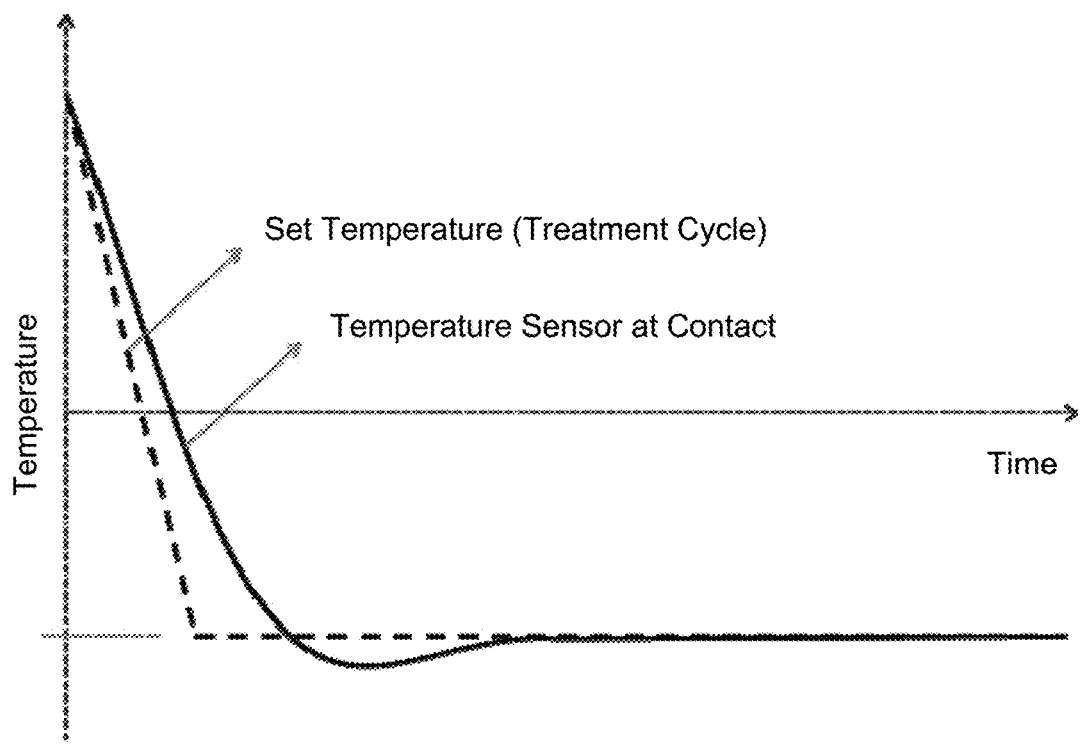
FIG. 16 shows a treatment cycle temperature profile and a temperature response measured by a temperature sensor at an applicator surface-tissue interface.

FIG. 16 shows an example treatment cycle temperature profile and a temperature response of the thermal sensor at the applicator surface-tissue interface. A target temperature of a temperature-controlled surface of the applicator (shown in dashed line) can be lowered at a predetermined rate and then held constant at a preset value. One or more sensors can monitor the temperature at the contact interface. Output from the sensors can be used to precisely control freeze execution in order to maximize cellular changes with a therapeutic purpose while inhibiting, limiting, or minimizing adverse treatment side effects. It may also be desirable to control the extent of skin freezing down to the epidermal-dermal layer, dermal-subcutaneous layer, or other specific depths. A desired freezing extent can be achieved based on knowledge of the freezing point temperature of the bulk tissue. In freeze events, tissue goes through ice nucleation and growth (exothermic phase change). An exothermic phase change is when the system releases heat to the surroundings (e.g., changing from a liquid to a solid) during the phase change. Freezing is an exothermic event, releasing heat for a very short time period, and this release of heat can be a reliable indicator of skin freezing. Thermal sensors can be used to detect the heat released by the phase change associated with a freeze event. When tissue is at a supercooled steady state, a thermal sensor (e.g., element 167 in FIG. 2) at the applicator surface-tissue contact location can detect that the temperature is stable, without any substantial sudden temperature changes or peaks. When the supercooled tissue freezes, the released heat is captured by the sensor as a sudden increase of temperature. FIG. 15B shows temperature increases in tests 2, 3, and 5 corresponding to the released heat.

Figure 17:
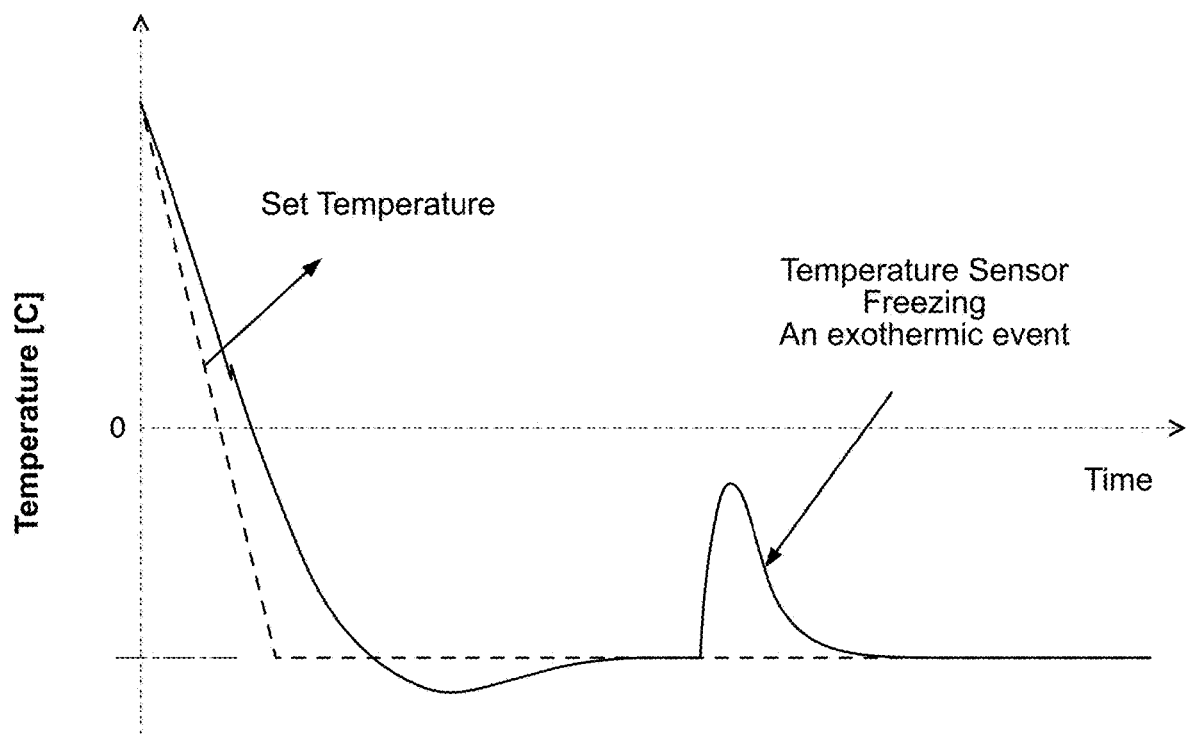
FIG. 17 shows the temperature of the applicator surface lowered at a constant rate and then held at a generally constant value in accordance with an embodiment of the technology.

FIG. 17 shows the set temperature of the applicator surface (shown in dashed line) lowered at a constant rate and then held at a generally constant value. The temperature at the applicator-tissue interface is detected by the thermal sensor and shown in solid line). After targeted tissue has been supercooled, a freeze event can be initiated. The temperature sensor can detect the temperature increase associated with the heat of fusion, and the detected increase in temperature can be identified as a change in phase. Various changes in temperature can be used to monitor tissue and detect phase changes. Some methods can include supercooling and using freezing set points to intentionally treat tissues at subzero temperatures. The tissue temperature can be lowered at a desired time during treatment to control onset of freezing. Thaw cycles can be included in any treatment cycle to warm tissue at a desired rate for protecting or enhancing tissue injury.

A treatment cycle can be determined by selecting supercooling parameters, freeze parameters, and thaw parameters. The supercooling parameters can include cooling profiles, target temperatures, and/or time periods. A cooling profile can include a cooling rate for ramp-down to reach the supercool temperature. The target tissue can be kept at a subzero target supercool temperature for the supercool time period without phase change.

Freeze parameters can include cooling profiles for keeping the tissue in the frozen state and/or time periods for keeping the tissue frozen. The freeze parameters can be selected to increase or decrease thermal injury. After completion of the freeze time period, cooled tissue can be warmed using a thawing cycle.

Supercooling parameters, freeze parameters, and/or thaw parameters can be obtained experimentally ex-vivo and/or in-vivo. For example, in-vivo human tests have shown that skin can be supercooled to subzero temperatures, for example, as low as −20° C., without phase change. When the temperature is lowered far enough, the tissue will freeze. It has been experimentally established that human skin tissue will often spontaneously freeze at around −25° C. The temperature of spontaneous freezing depends on the characteristics of the tissue, such as water content of tissue, cellular structure, etc.

Figure 18:
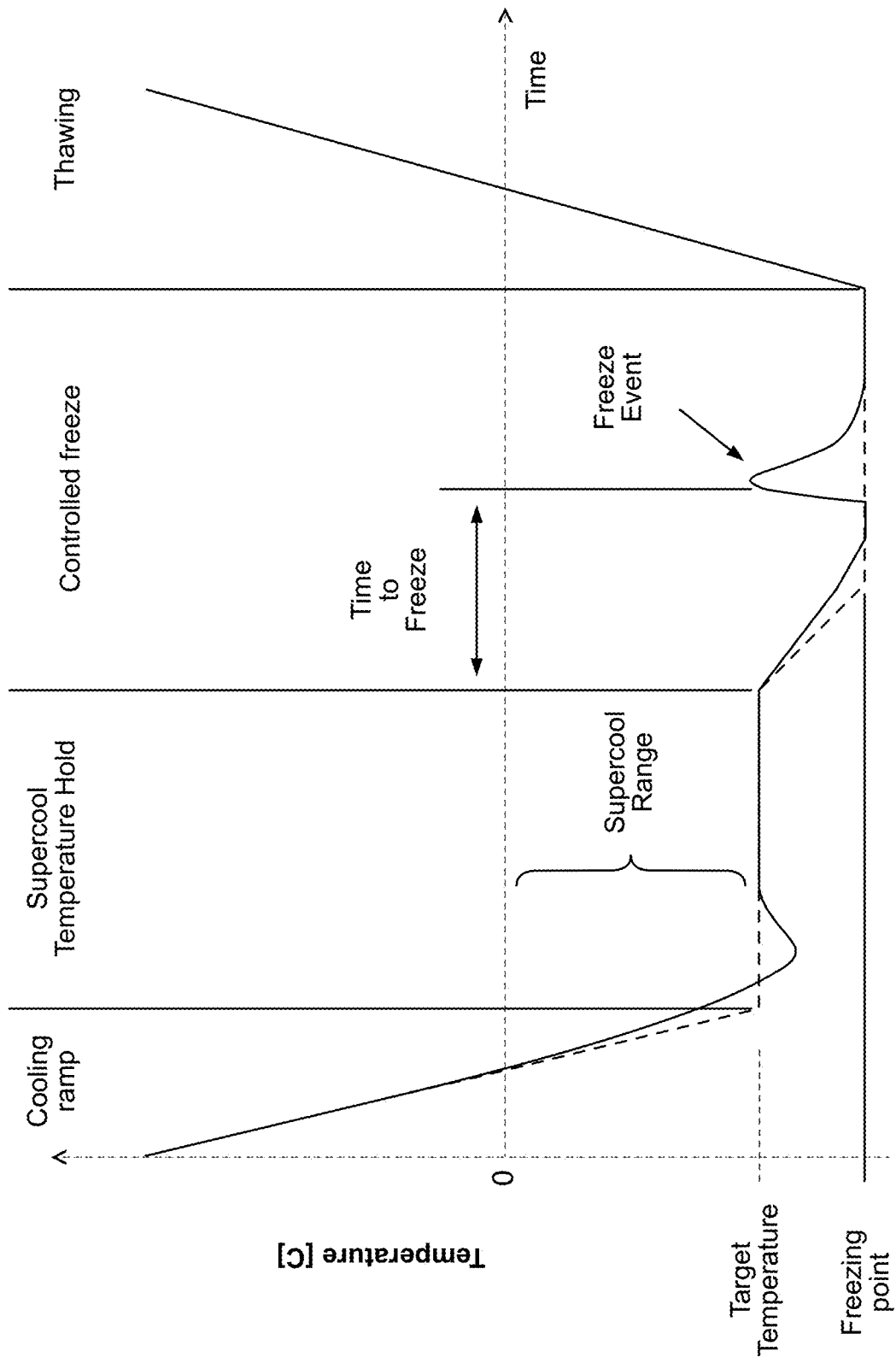
FIG. 18 is a plot of temperature versus time showing an exemplary treatment cycle for controlled supercooling and for controlled freezing of tissue by lowering the skin temperature in accordance with an embodiment of the technology.

FIG. 18 shows an exemplary treatment cycle for controlled supercooling and for controlled freezing. Temperature gradients within tissue during cooling protocols can be estimated by biothermal heat transfer modeling, experimental tests, or a combination of both. Heat transfer modeling can be used to predict the temperature gradients within tissue versus time during a treatment cycle. The volume of tissue, tissue depth, and other information about tissue at subzero temperatures can be calculated. For example, a flat applicator can cool skin to supercool targeted tissue between 0° C. to −20° C., 0° C. to −12° C., 0° C. to −10° C., 0° C. to −8° C. or other suitable temperature ranges to cool targeted tissue to a temperature equal to or lower than about −20° C., −15° C., −13° C., −12° C., −11° C., −10° C., −8° C., −6° C., −5° C., −4° C., −3° C., −2° C., −1° C., or 0° C. The target tissue can reach a general steady state at which the subject's body heat offsets continued heat withdrawal from the skin surface. The temperature-controlled surface of the applicator can be kept at a suitable temperature lower than the desired bulk temperature of the targeted tissue for the supercooling period. To freeze the supercooled tissue, a temperature of the applicator can be further lowered to ramp down to, for example, a melting/freezing point of a medium on the skin, a freezing point of an agent in the skin, or a freezing point of the skin itself.

Figure 19A:
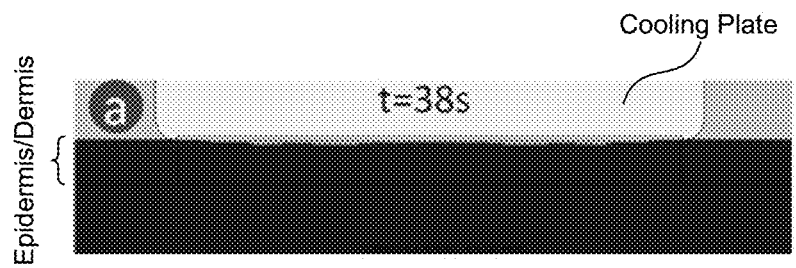
FIGS. 19A-19E are cross-sectional views of an applicator applied to a treatment site and thermal modeling.
Figure 19B:
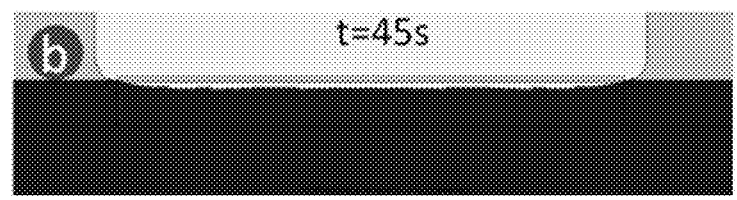
Figure 19C:
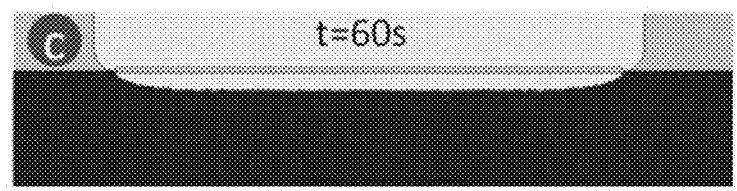
Figure 19D:
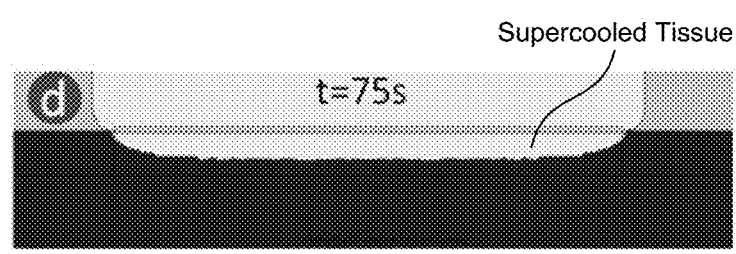
Figure 19E:
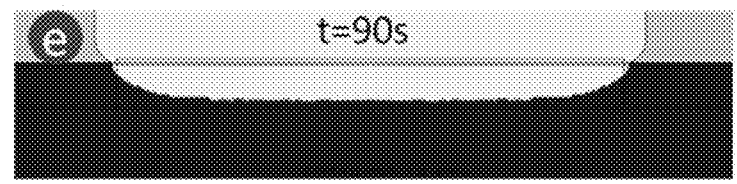

FIGS. 19A-19E are cross-sectional views of a cooling applicator applied to a treatment site and thermal modeling. FIG. 19A shows the treatment site at the start of a supercooling cooling cycle when shallow tissue begins to be supercooled. FIGS. 19B-19E show the amount of supercooled tissue increasing over time until the entire epidermis/dermis underlying a cooling plate is supercooled, while the subcutaneous layer is not supercooled. (Skin tissue that is supercooled is gray, and the non-supercooled tissue is black.) The supercooled tissue can be at a temperature within a range of about 0° C. to −20° C. The model for cooling skin is based on a flat plate applicator (with a treatment profile that ramps down at 1° C./s and a holding step at a target temperature of −20° C.) to predict that skin with an epidermal layer of 0.1 mm and a dermal layer of 2 mm, which are above a subcutaneous layer of 1.0 cm (10 mm), can be supercooled completely within 90 seconds. To freeze the whole underlying region of the epidermal/dermal layers, skin freeze can be triggered to occur at or after 90 seconds of supercooling. To freeze only a portion of underlying epidermis/dermis, skin freeze can be triggered to occur before 90 seconds (for example, after 45, 60, or 75 seconds of supercooling). The onset of the freeze event may be delayed for a short period of time (e.g., a few seconds) after the freezing temperature is reached due to the time it takes to cool the tissue to a lower set temperature and the time it takes for an ice nucleation event to occur, so some additional time may need to be added from a time a temperature dive is initiated until a thaw event is begun, to result in a desired amount of time the tissue is in a partially frozen state. For skin, approximately 15 seconds, 20 seconds, or 30 seconds can be average delay times from the beginning of a temperature dive until the freeze event has occurred.

When a freeze event is initiated, the entire dermis and epidermis underlying the applicator may not be completely frozen. This is because even at steady state (e.g., when heat extraction by the applicator balances warming from subdermal tissue and blood flow) the bulk temperature of the tissue is not cold enough to absorb all the heat of fusion from the freeze event so as to achieve a 100% tissue freeze. As the heat of fusion is released during the freeze event, the bulk temperature of the tissue rises to a level close to, for example, 0° C. such that additional freezing ceases (absent additional significant heat extraction by the applicator) and the skin is only partially frozen when equilibrium is established. The temperature of the cooling plate can be adjusted to compensate for heat of fusion or other natural heating associated with the subject's body. Without being bound by theory, it is believed that the skin would need to be supercooled to a temperature around −70° C. for the skin to totally freeze and remain complete frozen during a freeze event, but such a low supercool temperature is highly undesirable because severe adverse events, particularly to the epidermis, would result.

FIGS. 20A-20F illustrate stages of one method of freezing tissue without supercooling. Generally, an applicator can be applied to a treatment site after applying a coupling agent to the applicator and/or treatment site. The applicator can freeze a region of the skin while limiting or avoiding supercooling, as discussed below.

FIG. 20A shows a coupling media 209 (e.g., water, coupling gel, etc.) located along a temperature-controlled surface 211 of the applicator. The layer of coupling media can be formed by applying water to the temperature-controlled surface 211, which can be cooled to a temperature less than about −20° C., −15° C., −10° C., or another suitable temperature for freezing most of or all the coupling media 209. The temperature-controlled surface 211 can then be warmed to a higher temperature (e.g., −3° C., −2° C., or −1° C.) suitable for applying the applicator to the treatment site.

FIG. 20B shows a frozen upper layer 215 and a liquid lower layer 217 of the coupling media after the applicator has been applied to the treatment site 213. The warm skin can contact the liquid layer 217 gel while the layer of the frozen coupling media contacts the temperature-controlled surface 211 and remains frozen. The temperature-controlled surface 211 can be held at a temperature suitable for maintaining the frozen upper layer 215 and the liquid lower layer 217.

FIG. 20C shows the temperature-controlled surface 211 held at low temperature (e.g., −1° C., −2° C., −3° C., etc.) for a predetermined period of time to cool the skin to a temperature near its melting/freezing point. During this holding period, a portion of the coupling media which is frozen may slightly increase in volume, thereby increasing the thickness of the layer 215. The temperature of the temperature-controlled surface can be lowered or raised to increase or decrease the thickness of the frozen layer 215 while maintaining a liquid layer 217. In some procedures, the temperature-controlled surface 211 can be kept at a temperature within a temperature range of about −2° C. to about −12° C., about −4° C. to about −10° C., or other suitable temperature ranges. For example, the temperature-controlled surface 211 can be kept at a temperature of about −6° C., −8° C., or −10° C. As the temperature is reduced and/or held a lowered temperature, the freezing front of the coupling media moves towards the skin until substantially all or the entire layer of coupling media/gel freezes.

FIG. 20D shows the entire layer of coupling media 209 in a frozen state. The surface of the skin contacting the coupling media 209 can be lowered to its freezing point. Due to the skin's intimate contact with ice crystals in the frozen coupling gel 209, the skin will progressively freeze rather than supercool.

FIG. 20E shows a freezing front 221 and a frozen volume of tissue. The freezing front 221 can move deeper into the subject until a desired volume of tissue is frozen.

FIG. 20F shows temperature-controlled surface 211 held at a temperature of about −8° C. for 2 minutes to produce the enlarged volume of frozen tissue. The frozen volume of tissue can stop increasing and become constant when the steady state is established. In facial treatments, skin can be frozen without affecting underlying muscles and subcutaneous tissue. In some treatments, the applicator can freeze skin without affecting subcutaneous tissue to limit or avoid changing skin contours at the treatment site. In other treatments, subcutaneous tissue can be frozen to, for example, inhibit, disrupt, or reduce subcutaneous lipid-rich cells to contour the treatment site. For example, the applicator can treat acne and can also contour or not contour tissue in a single session.

The temperature of the temperature-controlled surface 211 can be increased to 18° C., 20° C., or 22° C. at a rate of 1° C./s, 2° C./s, or 3° C./s. This will quickly thaw the tissue to minimize or limit further damage to cells. For example, the skin can be cooled at a rate of 0.25° C./s, held at a target temperature of −8° C. for 2 minutes, and then thawed at a rate of 2° C./s. Other cooling rates, target temperatures, and thaw rates can be selected based on the desired level of freezing, thermal injury, etc.

Targeted tissue can be frozen more times than non-targeted tissue. Repetitive freeze-thaw cycles effectively damage or kill tissue because, aside from suffering multiple cycles of deleterious solution effect and mechanical ice crystal damage, cell membrane integrity will be compromised after the first freeze-thaw cycle, making it a less effective barrier for freeze propagation in subsequent freeze-thaw cycles, and cells are much more susceptible to lethal intracellular ice formation in the subsequent freeze-thaw cycles. In some embodiments, targeted tissue can be frozen multiple times in a single treatment session while freezing non-targeted tissue, such as the epidermis, only one time. Additionally, targeted tissue can be frozen multiple times without supercooling any tissue. In some procedures, the dermis is repeatedly frozen to injure or destroy target glands without repeatedly freezing the epidermis.

Figure 21:
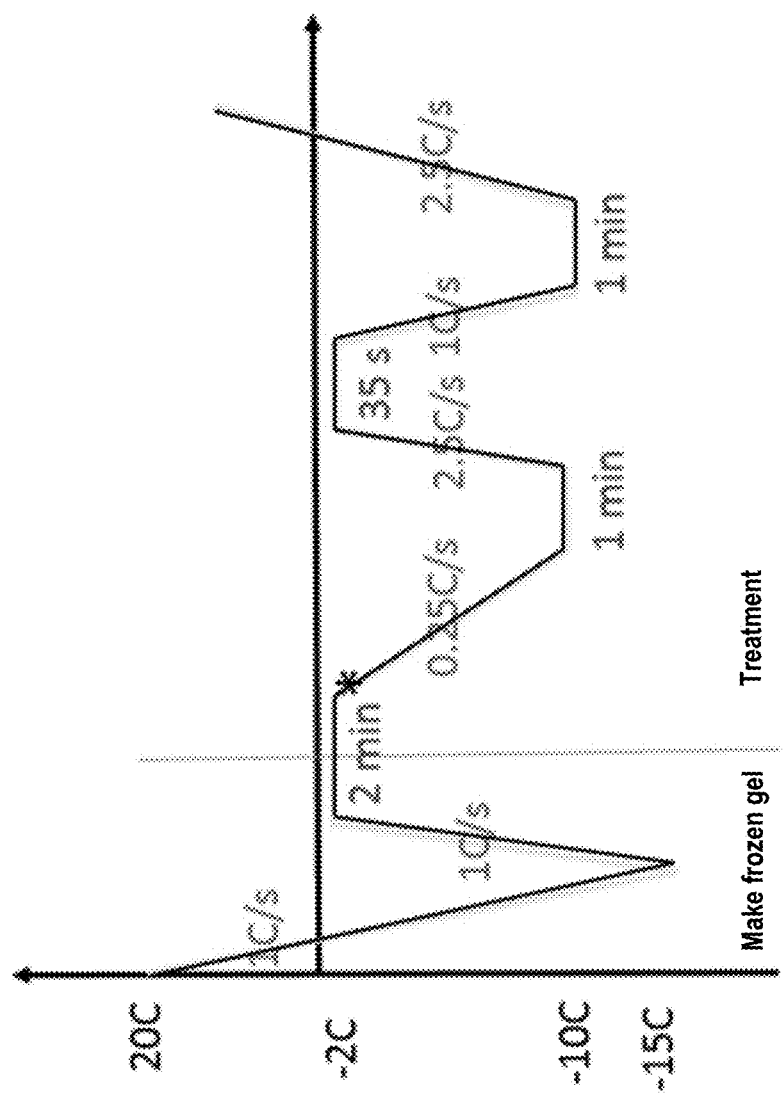
FIG. 21 is a plot of temperature versus time for freezing skin multiple times in accordance with an embodiment of the disclosed technology.

FIG. 21 is a plot of temperature versus time for freezing the skin multiple times in accordance with an embodiment of the disclosed technology. After a layer of frozen coupling media is created at −15° C., the temperature-controlled surface of the applicator is warmed to −2° C. to cool the skin using techniques discussed in connection with FIGS. 20A-20F. Thereafter, the freeze event happens while the skin-applicator interface is maintained at a temperature of about −2° C. (indicated by the "*"). The temperature-controlled surface is then cooled to −10° C., and the freeze event is held at −10° C. for a period of time (e.g., 1 minute, 2 minutes, etc.). FIG. 21 shows a 1 minute holding period. Thereafter, the temperature of the applicator is raised to −1.5° C. for about 35 seconds. At this temperature, the epidermis, which is in contact with the coupling media, can remain frozen. The dermis thaws due to internal body heat and, in particular, heat from blood flow which perfuses the dermis. Thereafter, the applicator is re-cooled to −10° C. or another suitable temperature for refreezing the dermis. The second freeze event can be held for a period of time, such as 1 minute, 2 minutes, etc. If desired, the dermis can be thawed again by warming the applicator to −1.5° C. and again refrozen at −10° C. while keeping the epidermis in a frozen non-thawed state. The thaw temperatures, warming rates, cooling rates, duration of freeze events, and refreeze temperatures can be selected based on the desired number of refreezes and severity of thermal injuries.

Because the epidermis is never thawed using this treatment protocol, a larger freezing rate will have a much less damaging effect on the epidermis. In second or subsequent freeze-thaw cycles, a much larger freezing rate can be used to transition from a thaw temperature (e.g., −1.5° C., −1° C., 0.5° C., etc.) to a refreeze temperature (e.g., −8° C., −10° C., −12° C.), and this may further increase the probability of intracellular ice formation in the dermis, as further explained below.

The repeated freezing approach allows for complete control over most or all or some of the variables that govern post-thaw tissue viability. These variables include, without limitation, skin freezing rate, target temperature, duration of freeze, and warming rate. The skin freezing rate is not as controllable using other approaches when skin is substantially supercooled because a macroscopic freeze event happens almost instantaneously (over a period of a few seconds) when skin is nucleated or inoculated with ice when the skin is in a supercooled state. Without being bound by theory, it is believed that the freezing rate is important because in a procedure in which extracellular space ice formation is triggered at −2° C., if the tissue is then slowly cooled to −10° C., there would be sufficient time for intracellular water to diffuse out and enter the extracellular space along a concentration gradient. This causes the intracellular solute concentration to rise and depress the intracellular melting/freezing temperature, thereby helping to reduce the probability of lethal intracellular ice formation at colder temperatures. However, if the skin is triggered to freeze at −10° C. (with a large supercooling window), there will not be enough time for cell dehydration, and thus no intracellular freezing point depression. Therefore, at a colder supercooling temperature (−10° C.), intracellular ice formation and associated increased cell damage is more likely. A large amount of supercooling has been demonstrated to correlate with greater risk of intracellular ice formation, which sometimes is desirable, but in other instances may be undesirable, depending on what tissue is and is not being targeted.

As discussed in connection with FIGS. 20A-20F and 21, treatment methods disclosed herein can provide complete control over all freeze-thaw parameters without allowing substantial skin supercooling that freezes larger amounts of tissue in faster time periods than procedures that do not use supercooling. When the associated effects of increased tissue disruption or damage in shorter time periods with supercooling is of particular therapeutic interest, a predetermined skin supercooling level with a predetermined duration can be achieved. A skin freeze can be triggered when a temperature of the applicator, coupling media, and skin is further cooled by, for example, a predetermined amount (e.g., less than 1° C., 2° C., 3° C., or 4° C.). For example, the applicator can be held at a temperature slightly colder than the freezing point of the selected coupling media, which contains an ice-nucleating substance and freezing point depressant, to ensure a layer of the coupling media contacting the applicator is frozen. By controlling the thickness of the layer of coupling media, the temperature gradient across the coupling media layer can result in a temperature slightly warmer than its freezing point and thus unfrozen coupling media can remain in contact with the skin. In some embodiments, the coupling media could be a hydrogel because hydrogels can be formulated to have precise thicknesses.

Figure 22B:
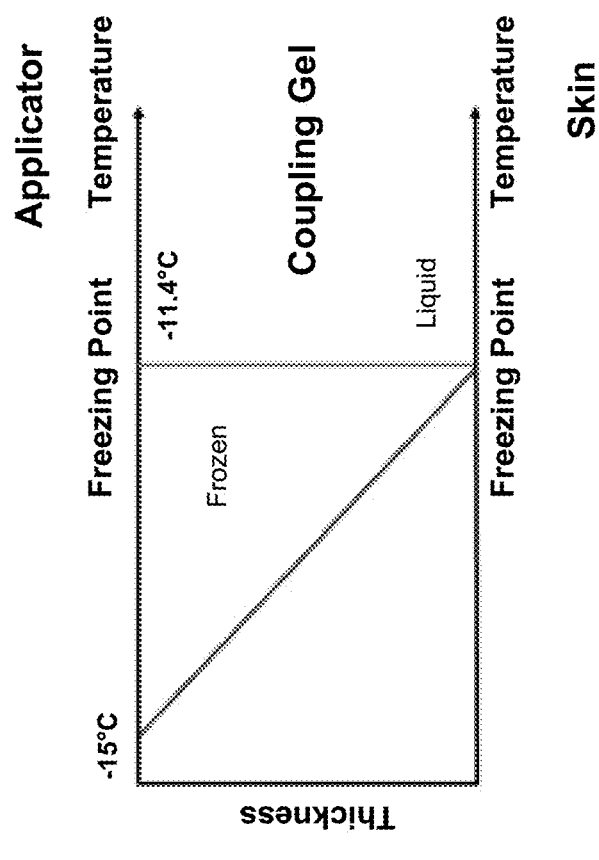
FIG. 22B shows the coupling media of FIG. 22A with a shifted temperature profile.
Figure 22A:
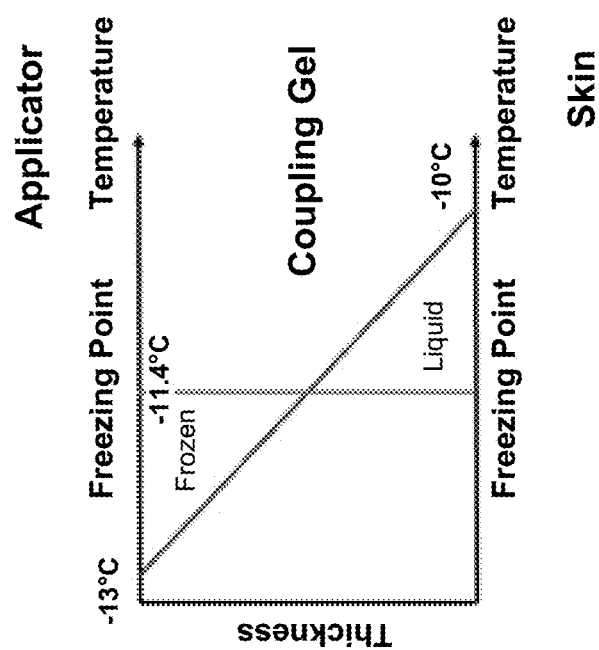
FIG. 22A shows an unfrozen liquid coupling media that can serve as an insulator for ice inoculation of skin.

FIG. 22A shows a liquid coupling media that can serve as an insulator for ice inoculation of the skin, thereby allowing the skin to supercool. To trigger a skin freeze, the applicator can be cooled a few degrees further to freeze the entire volume of coupling media. As shown in FIG. 22B, this process shifts the temperature profile to the left of the freezing point of the coupling media. When ice crystals in the coupling media do reach the skin, the supercooled skin can freeze immediately or in a short period of time.

Figure 23:
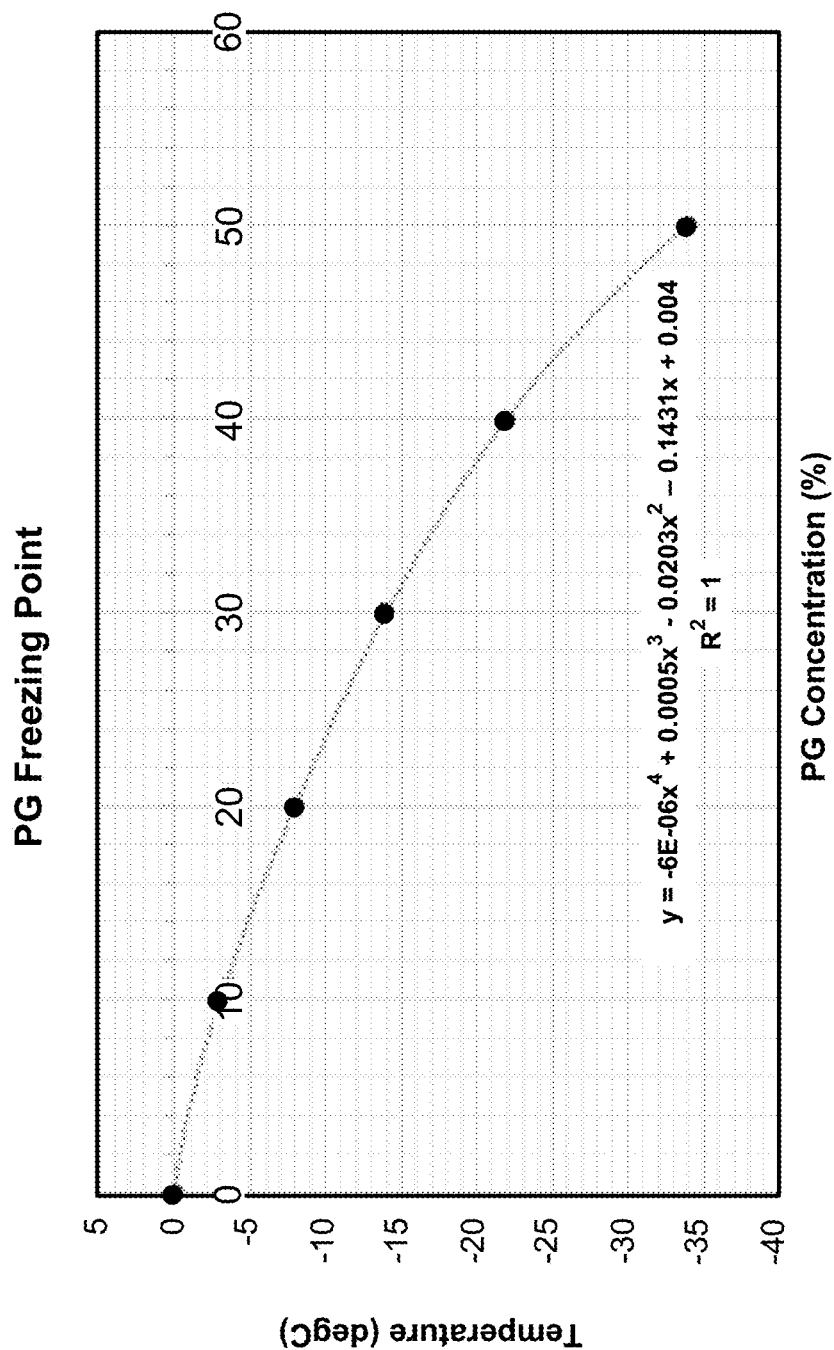
FIG. 23 is a plot of temperature versus propylene glycol (PG) concentration in water in accordance with an embodiment of the disclosed technology.

FIG. 23 shows freezing temperatures for varying concentrations of PG in water. FIGS. 24A-24F show stages of a method for supercooling the skin to −13° C., holding the temperature for 3 minutes, and then initiating a freeze event at −15° C. using a coupling media comprising 26% by volume PG with a freezing temperature of about −11.5° C. The concentration of the PG solution can be selected based on the desired temperature for initiating a freeze event.

Referring to FIGS. 24A-24F, coupling media can be applied to the applicator and the skin. The applicator is cooled by ramping down a temperature of a temperature-controlled surface to freeze coupling media, and it is then heated by ramping up to −13° C. Holding the temperature at −13° C. will ensure that at least a layer of frozen media remains in contact with the applicator. Coupling media in a liquid state is applied to the skin surface. The applicator is applied to the liquid coupling media on the skin and then cools the coupling media and the skin to freeze the target tissue. By selecting the composition of the coupling media (e.g., concentrations of PG, glycerol, etc.), melting/freezing points can be selected which results in desired temperatures for supercooling the skin while providing both a thin layer of frozen coupling media (e.g., a frozen layer on the applicator surface) and a thin layer of liquid coupling media (e.g., a liquid layer on the skin surface).

Figure 24A:
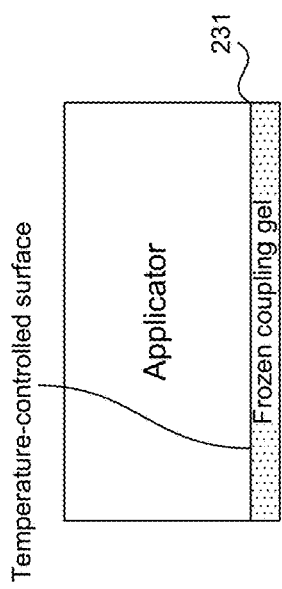
FIGS. 24A-24F show stages of a method for supercooling the skin and then initiating a freeze event in accordance with an embodiment of the disclosed technology.

FIG. 24A shows a layer of frozen coupling media 231 carried by the applicator. A carrier in the form of a paper towel soaked with 26% by volume PG/water can be placed on the temperature-controlled surface 211. The temperature-controlled surface 211 can be precooled to rapidly freeze the coupling media 231 once the paper towel is applied. In other procedures, coupling media is spread, sprayed, or otherwise applied directly to the temperature-controlled surface 211.

Figure 24B:
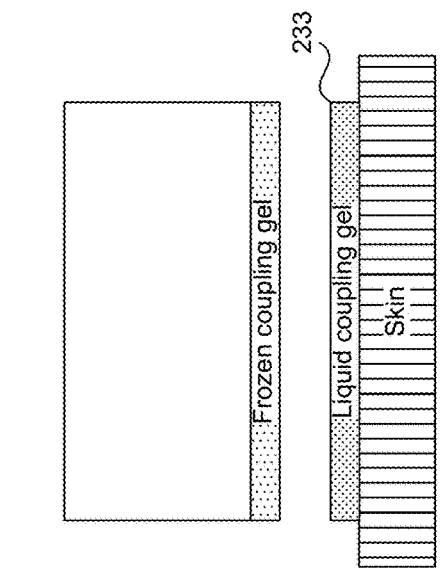

FIG. 24B shows another carrier in the form of a paper towel soaked with 26% by volume PG/water (at room temperature) applied to the subject's skin. The layer of liquid coupling media 233 (e.g., 26% PG/water) on the skin can be thick enough to prevent direct contact between the frozen coupling media 231 and the subject's skin upon placement of the applicator. Additionally, the liquid coupling media 233 helps improve a patient's comfort when placing the frozen coupling media 231 upon the coupling media 233.

Figure 24C:
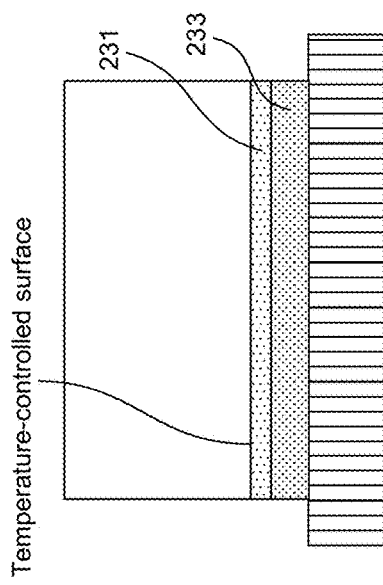

FIG. 24C shows the applicator after the frozen coupling media 231 has been placed in contact with the room temperature coupling media 233. The thickness and temperature of the liquid coupling media 233 can be selected such that it will melt only part of the frozen coupling media 231 so as to maintain a thin layer of frozen coupling media 231 along the temperature-controlled surface 211. A control system can control the applicator to maintain an applicator surface temperature at a target temperature, such as −13° C., which is below the freezing point (−11.5° C.) of 26% PG.

Figure 24D:
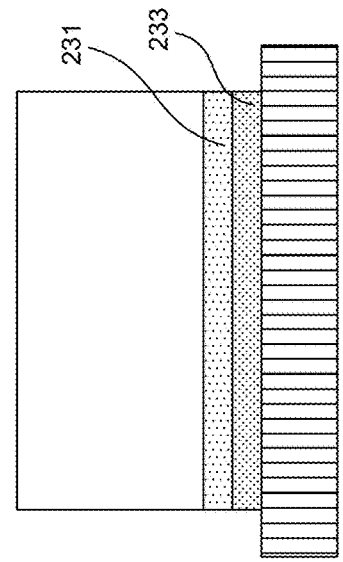

The applicator can continuously or intermittently extract heat to gradually increase the volume of frozen coupling media for a holding period. FIG. 24D shows the thickened layer of frozen coupling media 231. The coupling media 233 contacting the skin can remain in a liquid state and remain near but below its freezing temperature of −11.5° C.

Figure 24E:
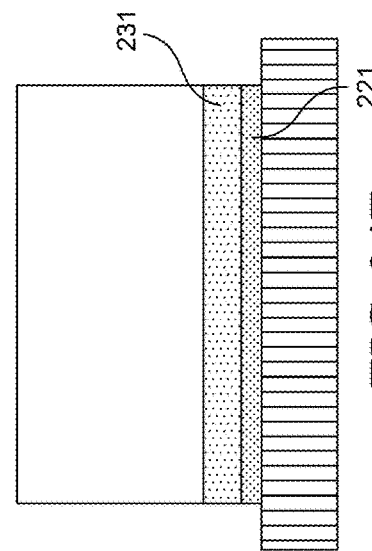

FIG. 24E shows the freezing front 221 moving toward the skin surface as the coupling media is cooled. When the coupling media in contact with the skin freezes, the supercooled skin will be inoculated and freeze rapidly over a period of a few seconds. For example, the applicator temperature can be ramped down to a temperature of about −15° C., −14° C., or −13° C. in order to freeze the entire coupling media volume (i.e., coupling media 231, 233), and thus trigger a freeze event in the skin.

The freeze event can be triggered by a temperature a few degrees colder than the supercooling temperature. In one procedure, skin can be cooled to a supercooling temperature of −13° C. while still being able to trigger a freeze at a temperature only slightly lower, such as −15° C. This "dive"

temperature of 2 degrees is much smaller than those required by conventional techniques that do not use a coupling media containing ice crystals that contact the skin (which are of the order of about 10 degrees) and serves as a skin-ice inoculating agent for triggering a predictable freeze event. For any given maximum end temperature for the applicator, a smaller dive temperature can result in a larger supercooled volume, and at the time of the tissue freeze, the frozen volume will also be larger compared to a treatment with a larger dive temperature. After the tissue has been frozen for a desired length of time, the applicator can warm the tissue to inhibit or limit further disruption, injury, etc. Warming and cooling cycles can be repeated any number of times in any order to thermally affect the targeted tissue.

Figure 24F:
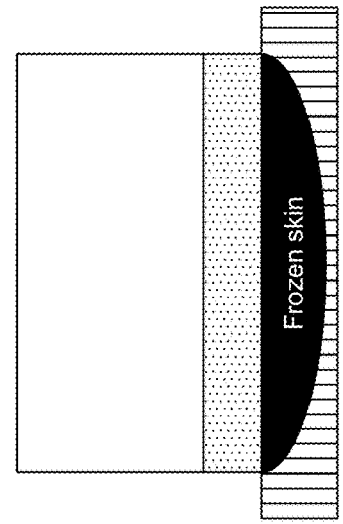

FIG. 24F shows the entire volume of coupling media at the applicator-skin interface and underlying tissue in a frozen state. The applicator can be cooled or heated to increase or decrease the volume of frozen tissue.

Figure 25:
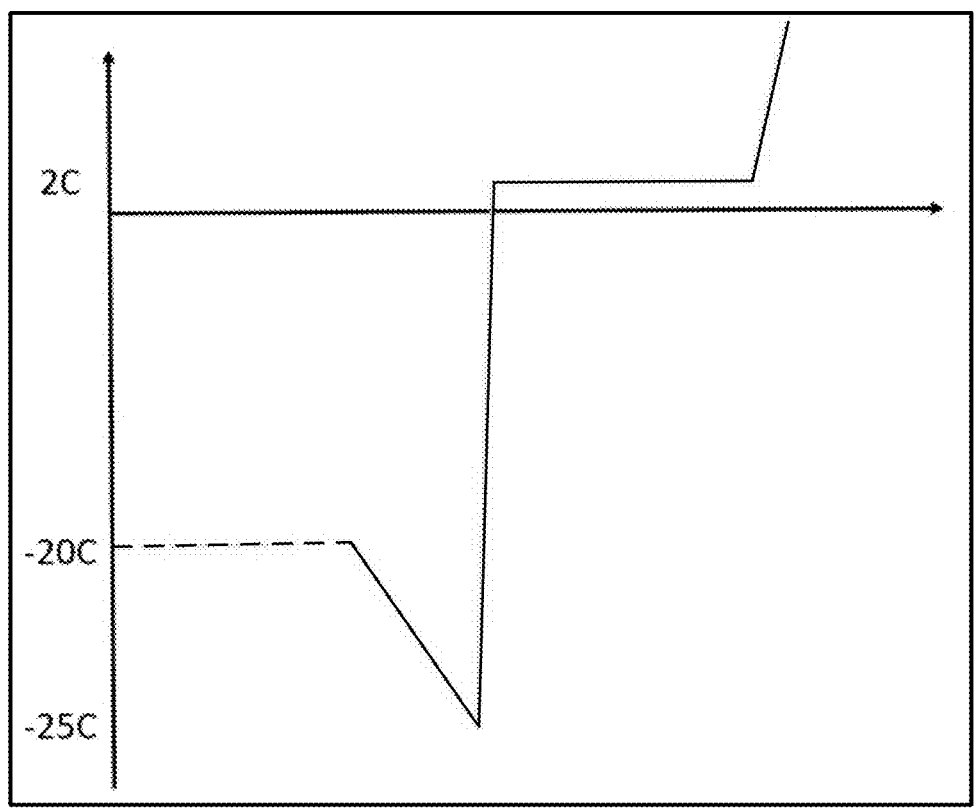
FIG. 25 is a plot of temperature versus time for supercooling and freezing tissue.

FIG. 25 is a plot of temperature versus time for supercooling and freezing tissue. The skin can be cooled to −20° C., and then a freeze is initiated at −25° C. by selecting a 37% by volume PG gel that has a freezing point of −19° C. Upon freezing of the skin, the applicator can rapidly warm the epidermis and hold it at a temperature sufficiently high enough to keep the epidermis unfrozen. For example, the epidermis can be held at a temperature of 1.5° C. or 2° C. This maximizes the underlying dermal freeze exposure to increase dermal damage and limits or minimizes the epidermal freeze exposure to reduce epidermal damage. Accordingly, warming can be used to minimize, limit, or substantially prevent thermal injuries that lead to hypopigmentation (skin lightening), hyperpigmentation (skin darkening), and/or other undesirable effects.

The skin can be cooled to a temperature above the freezing point of the coupling media in order to trigger a freeze event. When tissue is supercooled at −13° C. with a coupling media that has a slightly warmer freezing temperature (e.g., a freezing temperature of −11.5° C.), the skin will not be inoculated at temperatures significantly warmer than −13° C. In some procedures, it may be desirable to initiate a skin freeze at higher temperatures to minimize or limit injury to the epidermal tissue during the freeze event. To address this need, a higher temperature melting/freezing point can be achieved by dilution of the coupling media to a lower concentration of a freezing point depressant. The melting/freezing temperature of the coupling media can be raised a sufficient amount to trigger a freeze at a temperature well above the supercooling temperature. Briefly, supercooling at time t1 can be accomplished by choosing a coupling media that has a freezing temperature lower than that at time t1. After supercooling, the applicator temperature ramps up to a higher temperature at time t2. A volume of water can be delivered into the coupling media to dilute it, ensuring that the diluted coupling media has a freezing point warmer than the temperature at t2. This will trigger a freeze in the diluted coupling media to quickly trigger a skin freeze. A relatively warm on-command freeze in the supercooled diluted coupling media can be triggered using, for example, energy (e.g., ultrasound), low temperature probes (e.g., an extremely small cold finger probe), and/or an INA.

Figure 26:
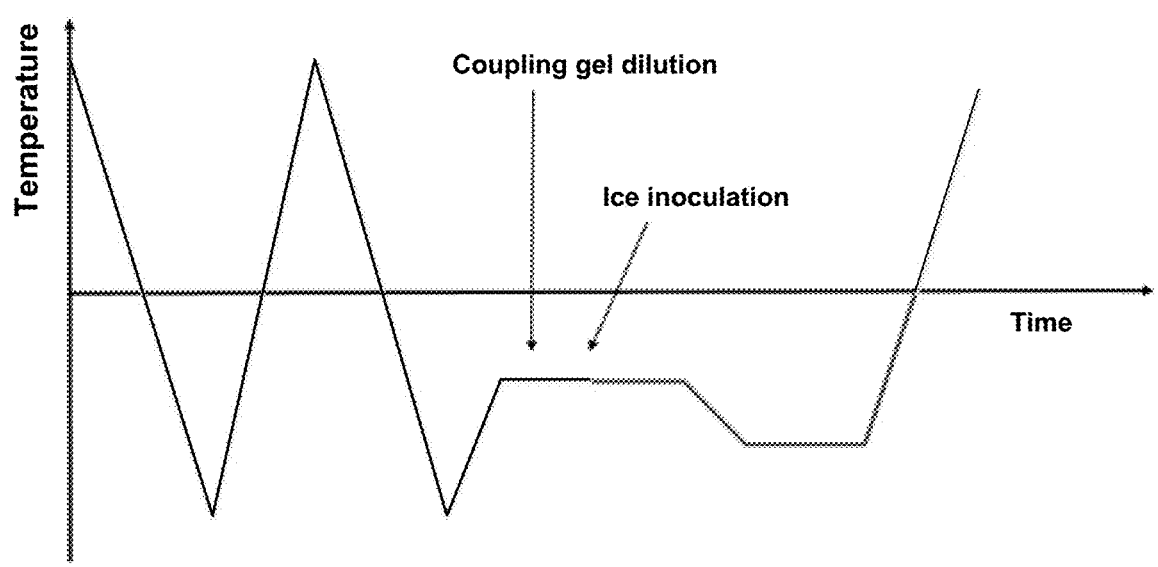
FIG. 26 is a plot of temperature versus time for a procedure that cycles two times to supercool tissue and then triggers a freeze.

FIG. 26 is a plot of temperature versus time for a procedure that cycles twice to supercool tissue and then triggers a freeze. Generally, tissue can be cycled between two temperatures (e.g., −10° C. and −20° C.) to supercool targeted tissue. A freeze event is triggered while at the higher temperature (e.g., −10° C.) or another suitable temperature. The freezing point of the coupling media can be selected to ensure that the coupling media does not freeze during a supercooling cycle. In some embodiments, the coupling media can comprise at least 39% by volume PG that has a freezing point of −20.5° C. so that the coupling media does not freeze during a supercool cycle at −20° C. to avoid initiating a premature skin freeze.

At the end of the supercool cycle, the temperature of the applicator can be raised to a higher temperature (e.g., −10° C.) suitable for ice inoculation. A substance, such as cold water at 1° C., can be infused through the applicator to dilute the coupling media. The temperature and flow rate of the water can be selected such that the diluted coupling media has a freezing point warmer than a predetermined value. For example, the diluted coupling media can have freezing point higher than about −10° C. for freeze inoculation at about −10° C.

Figure 27C:
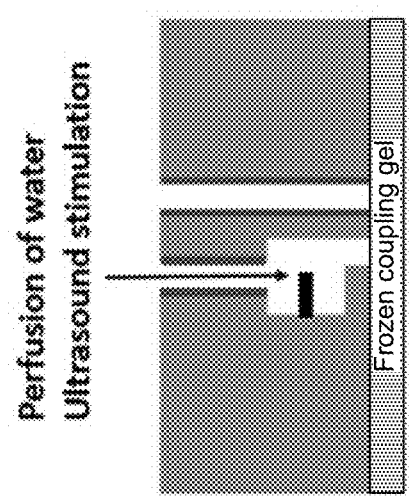
FIGS. 27A-27C show an applicator and a coupling media at various stages during a procedure.
Figure 27B:
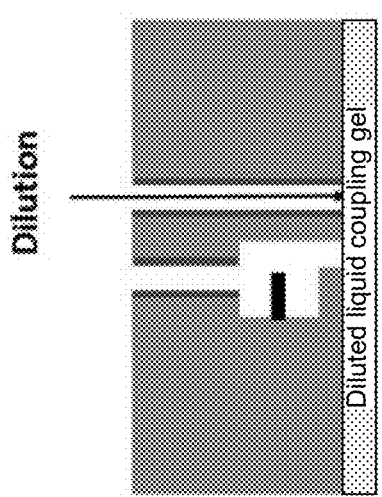
Figure 27A:
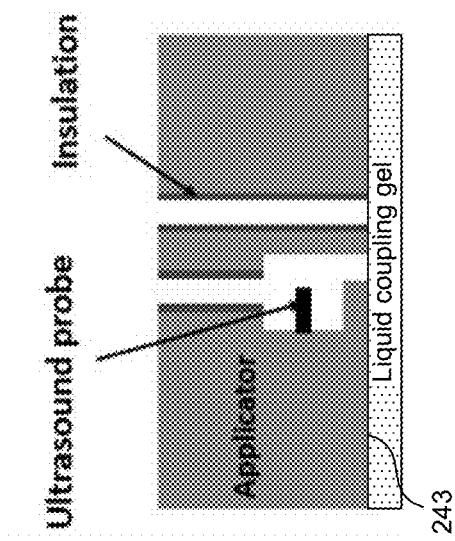

FIGS. 27A-27C show an applicator and a coupling media. Referring now to FIG. 27A, liquid coupling media is located along a temperature-controlled surface 243 of the applicator. Conduits, plates, and/or fluidic components of the applicator can have one or more thermally insulating coatings, layers, etc., to avoid unwanted freeze during infusion because the cold applicator plate can be at relatively low temperatures, for example, less than −5° C., −10° C., or −12° C. Additionally or alternatively, the applicator can include thermal elements (e.g., heating elements) for warming the diluting liquid, coolant (e.g., coolant delivered through the applicator), and other working fluids.

FIG. 27B shows the applicator and diluted coupling media. A diluting liquid has passed through the conduit to dilute the coupling media. The amount of diluting liquid can be selected to achieve the desired coupling media concentration. The coupling media can freeze as the applicator is cooled and the temperature of the coupling media stabilizes at a predetermined or target temperature, such as −8° C., −10° C., or −12° C. An INA can be incorporated into the coupling media or into the infused liquid to promote freezing.

Ultrasound can be used to initiate, promote, and/or control a freeze event. Referring now to FIG. 27A, cold water can be delivered into an ultrasound chamber and, in some embodiments, can contact an upper surface of the liquid coupling media. Cooling elements, cold plates, or other components of the applicator can cool the water surrounding an ultrasound probe, which can be activated to deliver ultrasound energy to the cooled water to cause freezing. Ultrasonic agitation (e.g., ultrasonic agitation with an appropriate frequency, power, etc.) can generate an instantaneous freeze event such that the freeze propagates throughout the chamber and reaches the coupling media, thereby triggering a freeze in the diluted coupling media shown in FIG. 27B.

One or more INAs can be incorporated into the coupling media before, during, and/or after applying the coupling media to the patient. Dilution of the coupling media to a point where its diluted melting temperature is above its actual temperature will cause the diluted coupling media to freeze, which in turn will cause freezing of the skin.

FIGS. 28-31 show treatments that can involve supercooling. Supercool cycling can cover a broad temperature range, with the coldest desired supercool temperature oftentimes being too cold to use as a freezing temperature because it would cause excess damage to the epidermis. Coupling media that remains in a liquid state during the supercool cycle will often not allow ice inoculation because the supercooling temperature range is above the freezing point of the coupling media. However, dilution of the coupling media raises the freezing point of the coupling media and enables freeze inoculation of the skin at warmer applicator and epidermal temperatures. Advantageously, epidermal temperatures can be sufficiently warm to inhibit, limit, or substantially prevent hypopigmentation, hyperpigmentation, or other undesirable effects.

Dilution also enables supercool cycling at relatively low temperatures (e.g., −10° C., −15° C., −20° C.) and tissue freezes at relatively high temperatures (e.g., −10° C., −5° C., −4° C., −3° C., or −2° C.) to enhance or maximize damage to targeted tissue and limit or minimize damage to non-targeted tissue. The targeted tissue can be tissue in the dermis and/or lower skin layers, and the non-targeted issue can be the epidermis or shallow tissue. Although enhancing or maximizing damage can be achieved by multiple consecutive treatments with different concentrations of coupling media, a single treatment can provide desired damage to reduce treatment time and costs.

Figure 28:
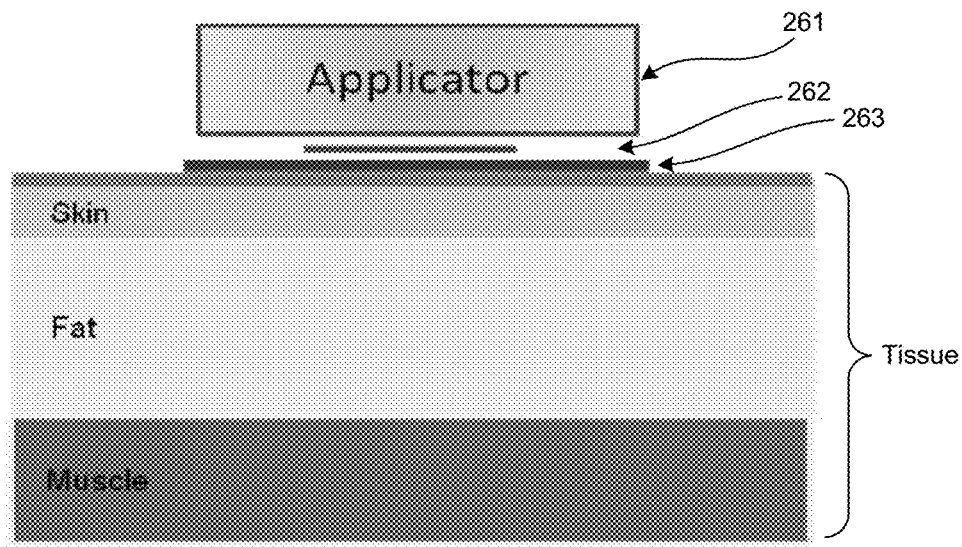
FIG. 28 shows an applicator applied to a treatment site in accordance with an embodiment of the disclosed technology.

FIG. 28 shows an applicator 261, media 262 with an INA, and a coupling layer 263. An INA can be placed in direct contact with the skin surface to facilitate a predictable freeze of the skin. In some procedures, the INA is placed in direct contact with a cooling surface of the applicator. For example, the media 262 can include one or more INAs (e.g., SNOMAX®/water mix). The coupling layer 263 can include cellulose-derived layer and solution, such as water, and can be in direct contact with a treatment site. In some embodiments, the INA can be applied using a thin layer (e.g., paper) soaked with an INA coupling agent, mixed with a gel like substance, delivered via an delivery instrument (e.g., syringe), or sprayed over the surface. One skilled in the art could substitute appropriate coupling layers materials, chemicals, conditions, and delivery systems with other materials, chemicals, conditions, delivery systems, etc.

Figure 29:
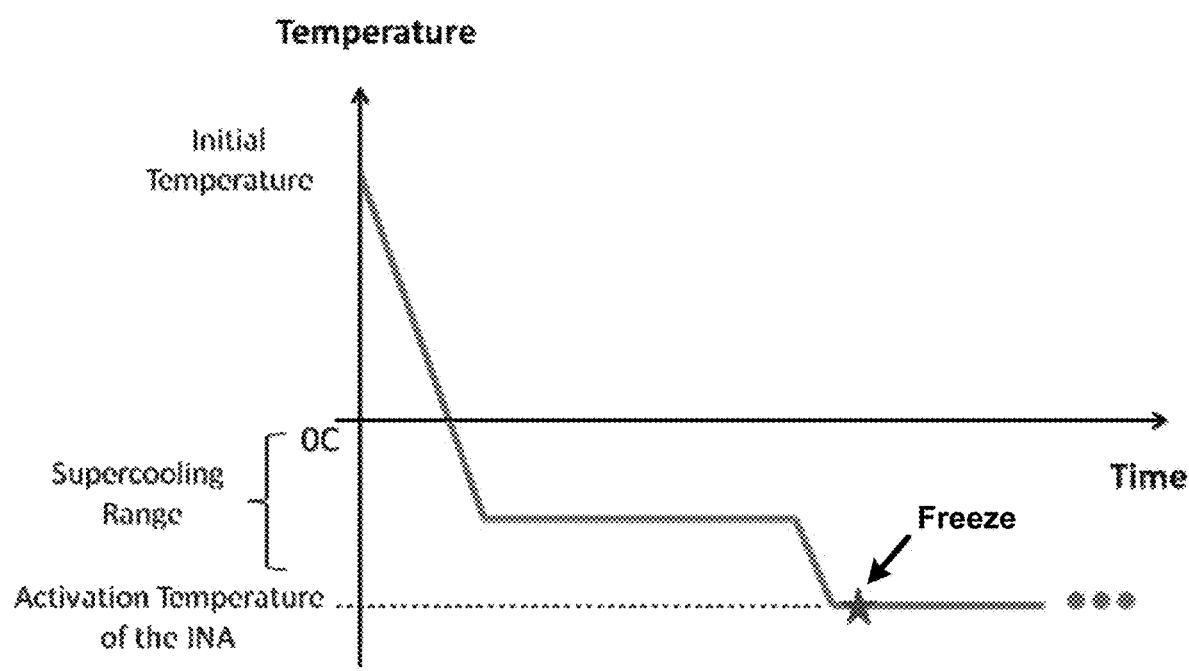
FIG. 29 is a plot of temperature versus time for a temperature profile for triggering ice nucleation by activating an ice nucleator.

FIG. 29 shows a plot of temperature versus time of a temperature profile for triggering ice nucleation via INAs. Tissue can be supercooled to a temperature above the INA activation temperature. The temperature of the INA is then lowered to its activation temperature to initiate ice nucleation to produce a partial or total freeze event (indicated by the "*") propagating into and through the skin. The cycle can be completed by holding a temperature of the applicator to permit the growth of ice crystals at the treatment site. After completing the cycle, the temperature of the applicator can be gradually raised at a desired thaw rate to warm the skin.

Figure 30:
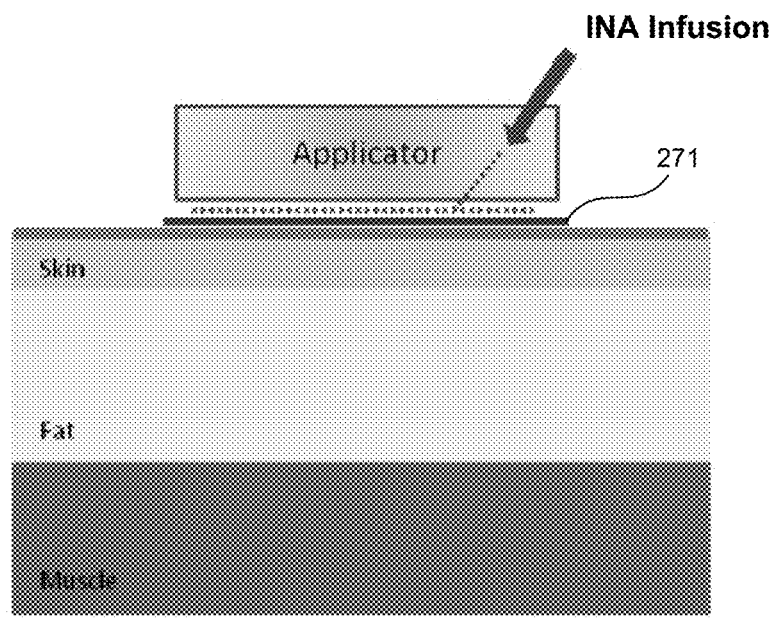
FIG. 30 shows an applicator and an ice nucleating agent (INA) applied to a treatment site in accordance with an embodiment of the disclosed technology.

FIG. 30 shows an applicator and an INA applied to a treatment site. The INA can be delivered into coupling media 271, onto a subject's skin surface, and/or into the skin to predictably trigger ice nucleation. The applicator can include embedded fluidics for controllably delivering the INA to the interface between the applicator and the subject's skin. The infused INA can be at a specific treatment temperature or within a predetermined temperature range to inhibit ice nucleation within, for example, coupling media at the interface or the tissue itself. In other embodiments, the INA is sprayed or otherwise delivered to the coupling media or the subject's skin. In some procedures, the applicator cools the coupling media and the subject's skin. The applicator can be lifted off the coupling media, and the INA can be sprayed onto the cooled coupling media. After spraying the INA, the applicator can be reapplied to the treatment site to continue cooling the INA, coupling media, and tissue. Needles, rollers, and other delivery instruments can be used to apply one or more INAs. Other techniques can be used to provide INA infusion through the coupling media, as well as on or into the coupling media and/or subject's tissue, etc.

Figure 31:
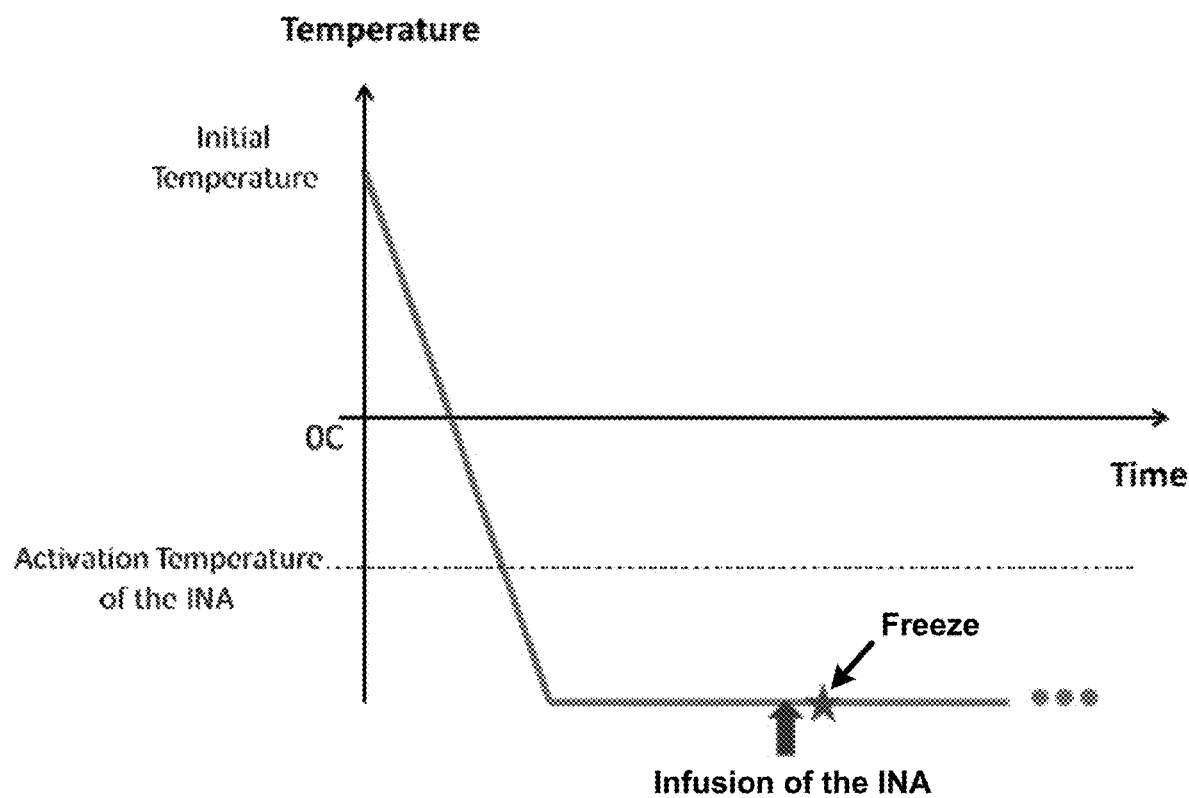
FIG. 31 shows a plot of temperature versus time for delivering an INA for nucleation.

FIG. 31 shows a plot of temperature versus time for delivering an INA for nucleation. The INA can be delivered to a treatment site, which can be at or below the INA's activation temperature (indicated by a dashed line), at a specific time to initiate nucleation. As indicated by the arrow, the INA can be infused to initiate the freeze event. Accordingly, the INA's activation temperature can be selected to trigger a controlled freeze event.

Various techniques can be used to protect non-targeted tissue while affecting targeted tissue volumes and/or specific structures within, for example, the epidermis, dermis, subcutaneous tissue, etc. The targeted structures can include, without limitation, hair (e.g., hair follicles), skin appendages (e.g., sweat glands, sebaceous glands, etc.), nerves, and/or dermal components, such as collagen, elastin, or blood microvascularity. Targeted structures can be affected while inhibiting, preventing, or substantially eliminating unwanted side effects. Because appendages and other cells/structures may have different lethal temperatures, a multi-step temperature profile can be used to target specific tissue and/or structures. Moreover, preserving the non-targeted tissue, such as the epidermis, from undue injury or damage could be beneficial in to prevent, for example, pigment changes and/or scarring, as well as to promote healing. Freezing the epidermis at a different temperature than the underlying dermis can be achieved by using the characteristic activation temperature of the INA and by intentionally supercooling the dermis at lower temperatures before applying the INA. In some procedures, the epidermis can be at a higher temperature to inhibit, limit, or substantially prevent permanent thermal injuries to the epidermis.

Some embodiments of the technology include methods of using linked polymers containing water, a crosslinked polymer that contains water, optionally an INA, and/or optionally a freezing point depressant for controlled freeze of skin tissue. According to one preferred embodiment, the polymer can be a hydrogel for use for controlled freezing of skin tissue. The hydrogel can be an effective initiator of a freeze event. As hydrogel freezes, it can provide initial seeds or crystal sites to inoculate and freeze tissue, thus catalyzing a controlled predictable freeze at specific temperature(s) in skin.

Figure 32A:
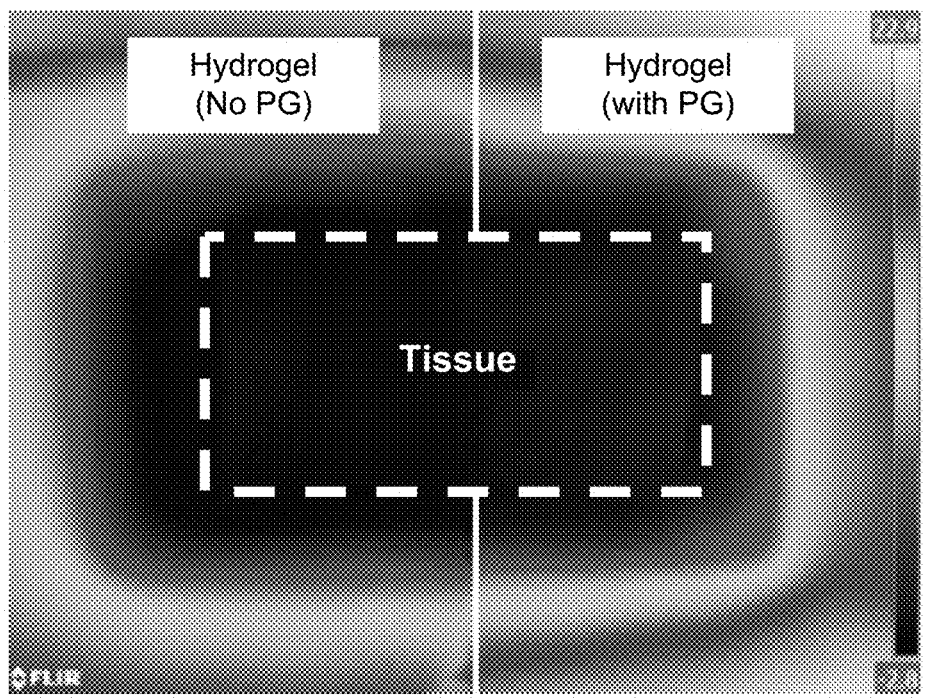
FIGS. 32A-32D are IR images showing stages of a process using hydrogel to freeze supercooled tissue.
Figure 32B:
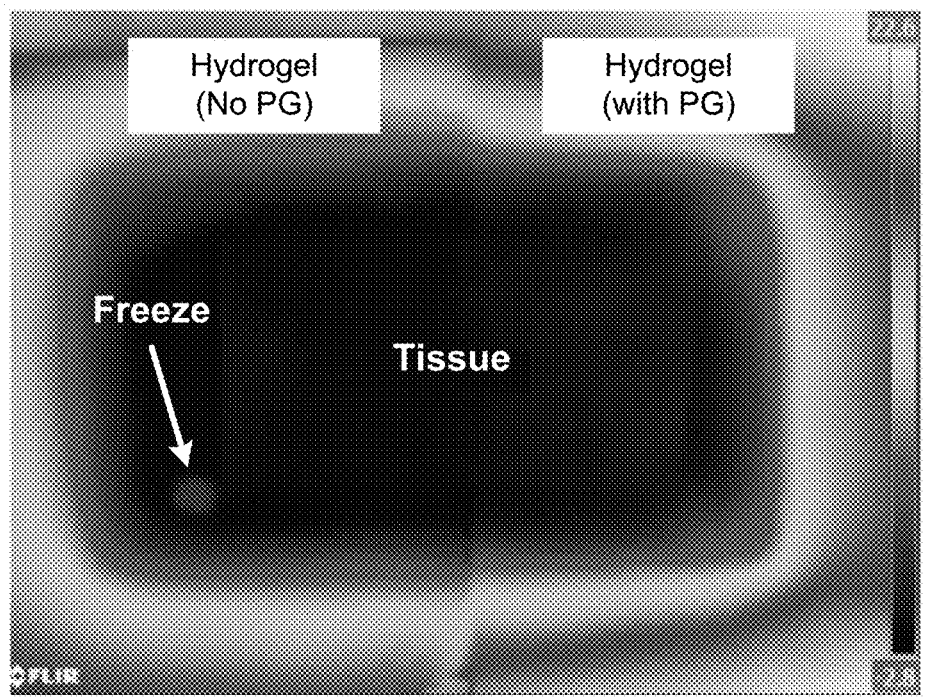
Figure 32C:
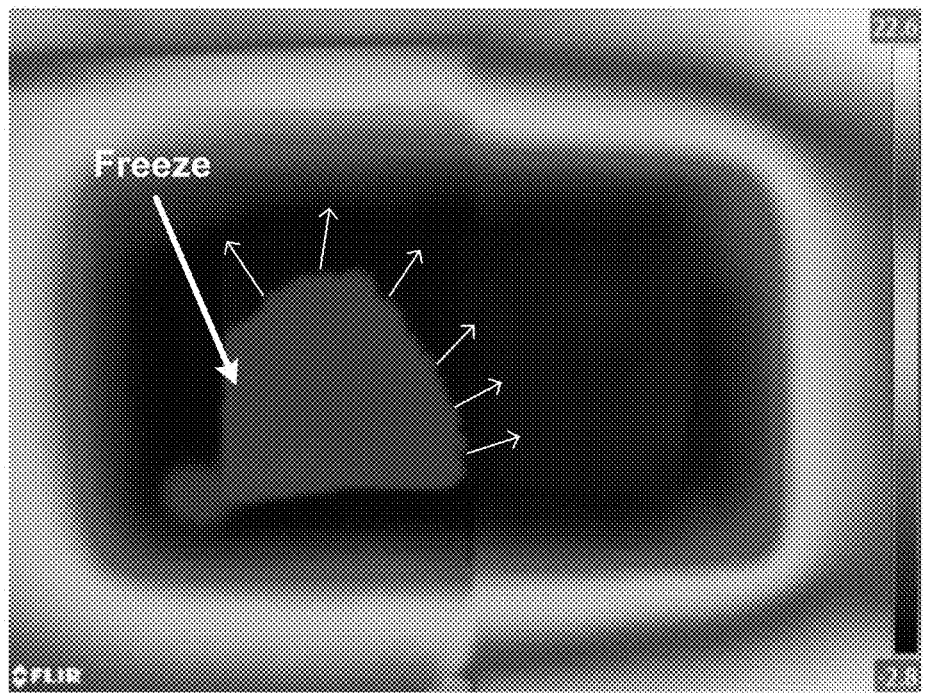
Figure 32D:
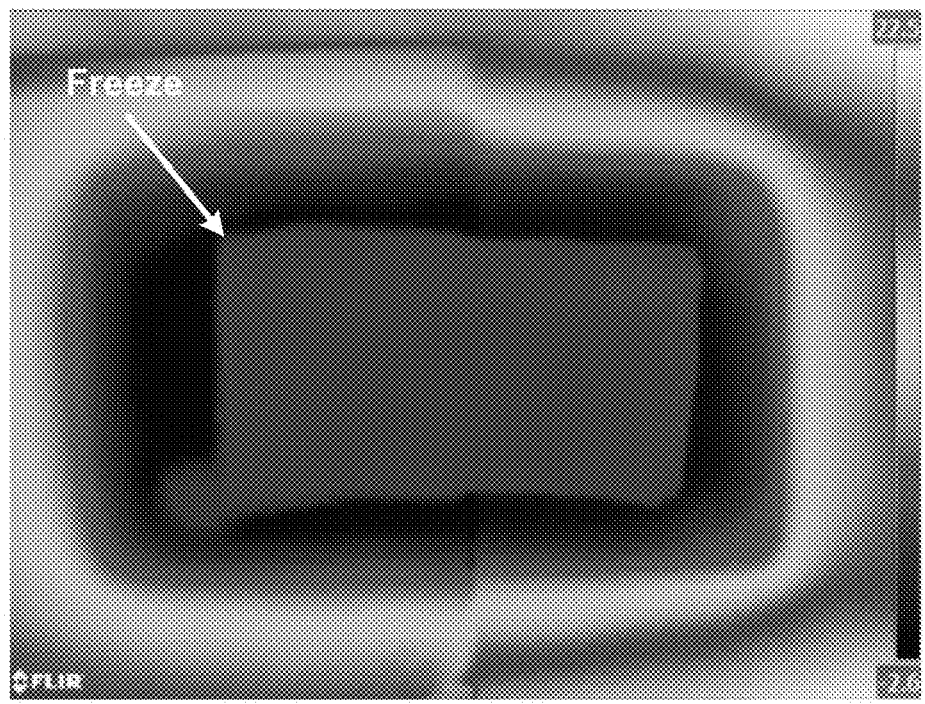

FIGS. 32A-32D show IR imaging of tissue freeze inoculation using a hydrogel with supercooled tissue. FIG. 32A shows skin tissue (dashed area) over two hydrogels (left and right halves) and a cooling plate overlying the hydrogels. FIG. 32B shows freezing at a lower left portion. FIG. 32C shows freeze propagation along most of the left hydrogel demonstrating ice inoculation. FIG. 32D shows freeze propagation through both hydrogels.

Referring now to FIG. 32A, the skin tissue at the area indicated by dashed lines contacts two half-sheets of hydrogel. A hydrogel sheet with no PG or other freezing point depressant is located to the left of the vertical line, and a hydrogel sheet with about 50% by volume PG is located to the right of the vertical line. A rectangular cooling plate is located on the hydrogel sheets. The skin surface is in direct contact with both hydrogels, which in turn are in direct contact with the cooling plate. In this manner, the hydrogels can be held firmly between the patient and the applicator.

The images were generated after a few minutes of supercooling the tissue. The temperature of the supercooled tissue was lowered to a trigger temperature to trigger a freeze (illustrated in lighter color) in the non-PG hydrogel, illustrated on the left side of FIG. 32B. FIGS. 32B and 32C show freeze propagation caused using only a hydrogel. The right half of FIG. 32B shows a section of the 50% by volume PG hydrogel and adjacent skin that has not been frozen. FIG. 32C shows the freeze propagating across the hydrogel, through the tissue, and toward the hydrogel with the temperature depressant. This shows that varying concentrations of PG or other freezing point depressants can be included in the hydrogel to lower the hydrogel's melting/freezing temperature to a desired value lower than 0° C. For water-based hydrogels with no PG or other freezing point depressant, freezing at temperatures close to 0° C. is inconsistent and unpredictable for a controlled heterogeneous nucleation. However, hydrogels used in combination with an INA provide the capability for a controlled freeze at subzero temperatures, including temperatures close to 0° C. (or lower when used in conjunction with a freezing point depressant) in a more predictable manner.

Figure 33A:
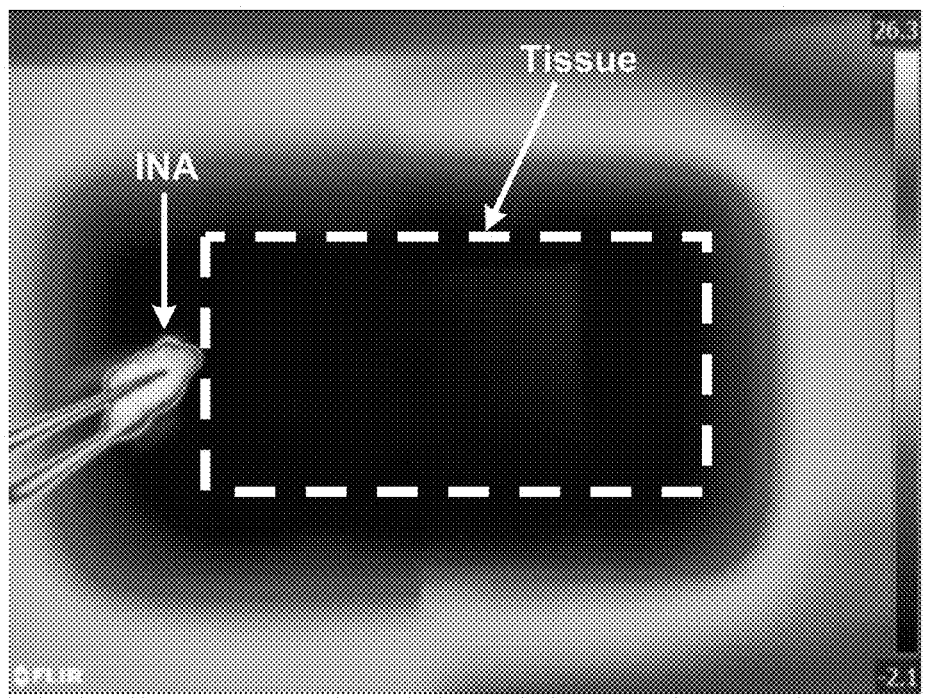
FIGS. 33A-33D are IR images showing tissue freeze inoculation using combined materials.
Figure 33B:
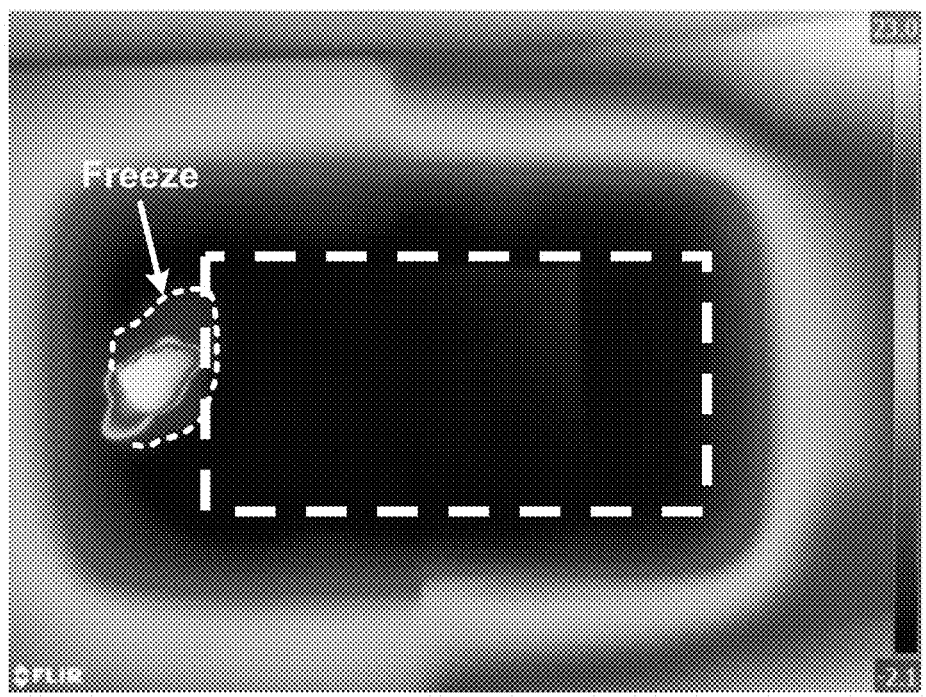
Figure 33C:
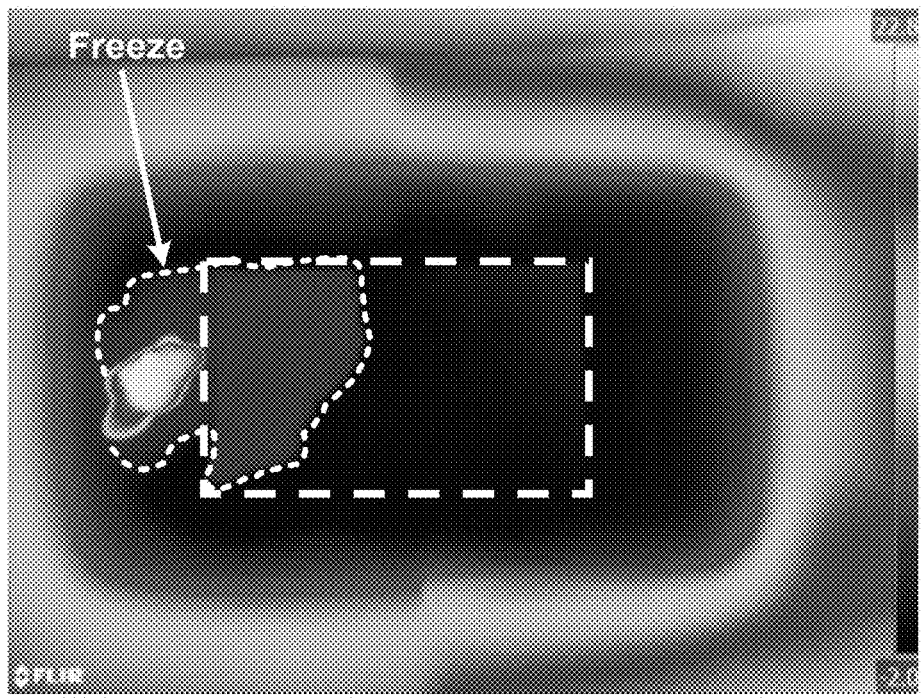
Figure 33D:
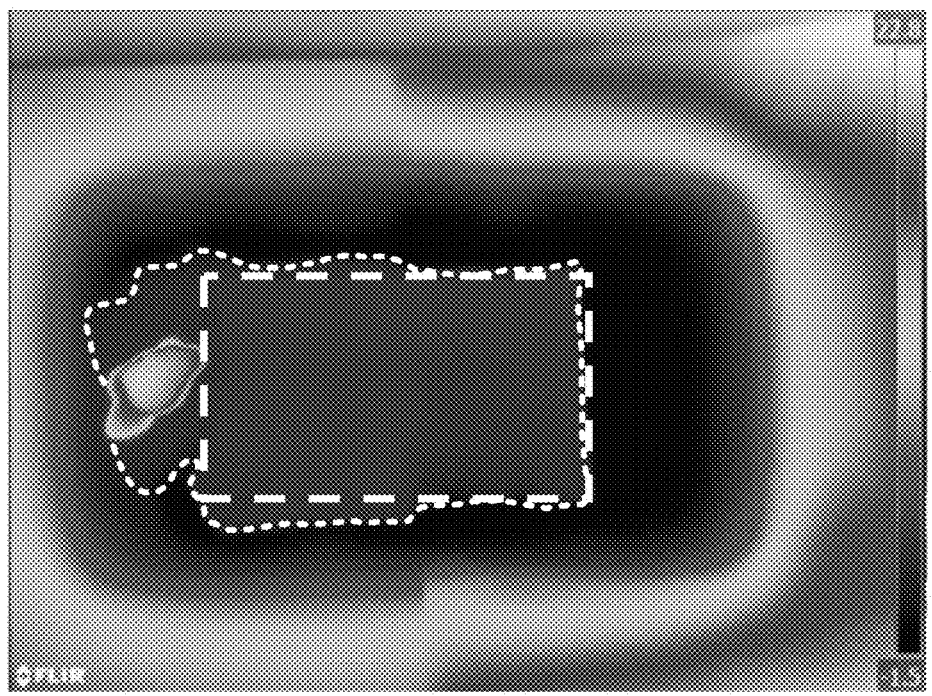

FIGS. 33A-33D are IR images showing tissue freeze inoculation using combined materials and the effect over time of placing an INA (e.g., SNOMAX® or other suitable INA derived from bacterium *Pseudomonas syringae*) on a supercooled hydrogel to trigger a freeze. FIG. 33A shows placement of a grain of an INA on a supercooled hydrogel. FIG. 33B shows an INA inoculating the hydrogel and a freeze starting to propagate around the INA. FIG. 33C shows freeze propagating across the hydrogel to the tissue demonstrating ice inoculation of skin. FIG. 33D shows the completed freeze propagation. Combined, the FIGS. 33A-33D show the feasibility of using an INA as a seed for inoculating a controlled freeze in skin tissue. Details of FIGS. 33A-33D are discussed below.

FIG. 33A shows unfrozen hydrogel and the INA being placed near an edge of a cooling plate (indicated by dashed lines) while the cooling plate cools the tissue. Upon initial placement of the INA, there is no substantial freezing through tissue facing the cooling plate. The INA can initiate the freezing process by serving as an ice nucleator and can raise the predictable freezing temperature of water to about −3° C. Although the melting/freezing temperature of water is 0° C., water has the tendency to supercool, so its freezing temperature is often far lower than 0° C. or −3° C. when an INA has not been used. The INA can initiate the freezing process by serving as an ice nucleator and can raise the predictable freezing temperature of water to about −3° C. The INA can be selected to raise the predictable freezing temperature of water to other desired temperatures. When selecting an INA, one skilled in the art can choose appropriate agents (e.g., organic or inorganic derived agents) to use for specific desired temperature(s) and to be delivered at specific times for a specific treatment purpose. Different techniques can be used to incorporate INA into hydrogels. For example, an INA can be sandwiched between layers of a hydrogel so as to be totally contained and encapsulated therein and so as to never come in contact with skin or tissue. An encapsulant can be disrupted, destroyed, or otherwise altered to release the INA. In some embodiments, a cooling plate of an applicator can deliver the INA to the hydrogel via one or more needles, exit ports, or other delivery means. The INA can be applied at a single location or multiple locations, or it can be mixed into the hydrogel compound. Additionally, the INA can be inside a micrometric wall made of hard or soft soluble film so as to avoid direct skin contact and have controlled degradation by passive or active means. Additionally, the INA can be injected or delivered into or onto the skin.

FIG. 33B shows the tissue after the freeze has propagated away from the INA. The frozen material is illustrated by a lighter color against a darker background color, which illustrates non-frozen tissue. FIG. 33C shows freeze propagating across the hydrogel facing the cooling plate. FIG. 33D shows the completed freeze propagation to freeze all of the skin directly contacting the hydrogel.

Figure 34A:
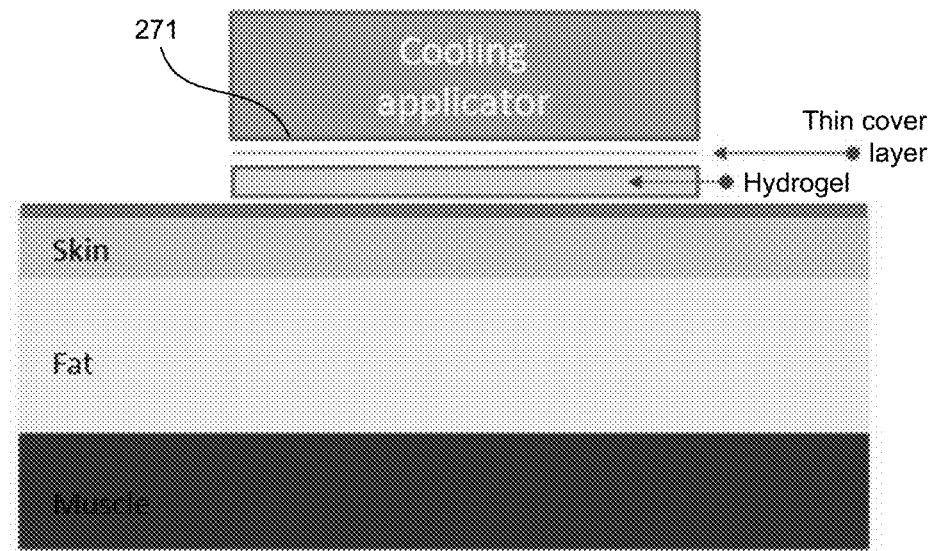
FIGS. 34A and 34B are cross-sectional views of an applicator applied to a treatment site in accordance with some embodiments of the disclosed technology.
Figure 34B:
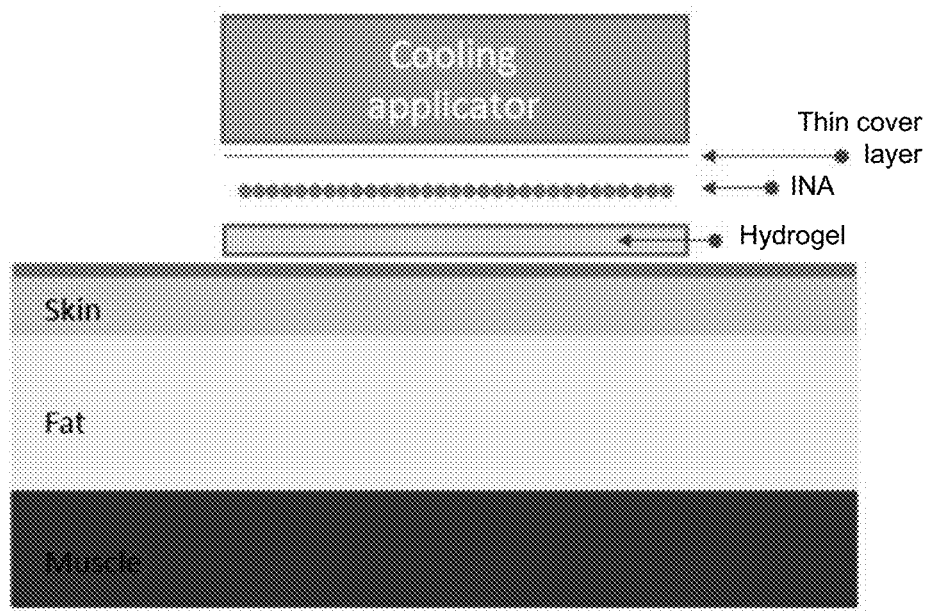

FIGS. 34A and 34B are cross-sectional views of the cooling applicator applied to a treatment site. Referring now to FIG. 34A, only a hydrogel is located between the applicator and the subject's skin. The cooling applicator can be disposed over a protective layer in the form of a thin cover layer. The protective layer can be a liner or other component for preventing cross-contamination or soiling by the hydrogel. As a temperature-controlled surface of the cooling applicator is cooled, it in turn cools the skin by withdrawing heat from the skin through the hydrogel and thin cover layer.

FIG. 34B shows a hydrogel and an INA located between the applicator and the subject's skin. The INA can be a liquid, gel, cream, preformed sheet or layer located along a surface of the hydrogel. When the applicator is applied to the hydrogel, the INA can be located at the hydrogel-applicator interface. The hydrogel and/or hydrogel/INA/freezing point depressant can be selected to melt/freeze at a specific temperature designed into its formulation.

The hydrogel of FIGS. 34A and 34B can be formulated to have a constituent ratio of water-monomer-crosslinker and/or other chemicals, such as one or more INAs, freezing point depressants, etc., to achieve a specific freezing point (or close range of temperatures) that may or may not allow for skin supercooling. An INA can have a known activation temperature (natural freezing point) and can be in solid form (i.e., powder) or mix solution with a desired concentration to create a predictable and consistent skin freeze. With such thermal coupling materials or compounds, a desired treatment temperature protocol or algorithm can be implemented to allow for supercooling if desired, or no supercooling if desired, and to allow for predictable and controlled freezing at preferred temperatures and times.

Figure 35:
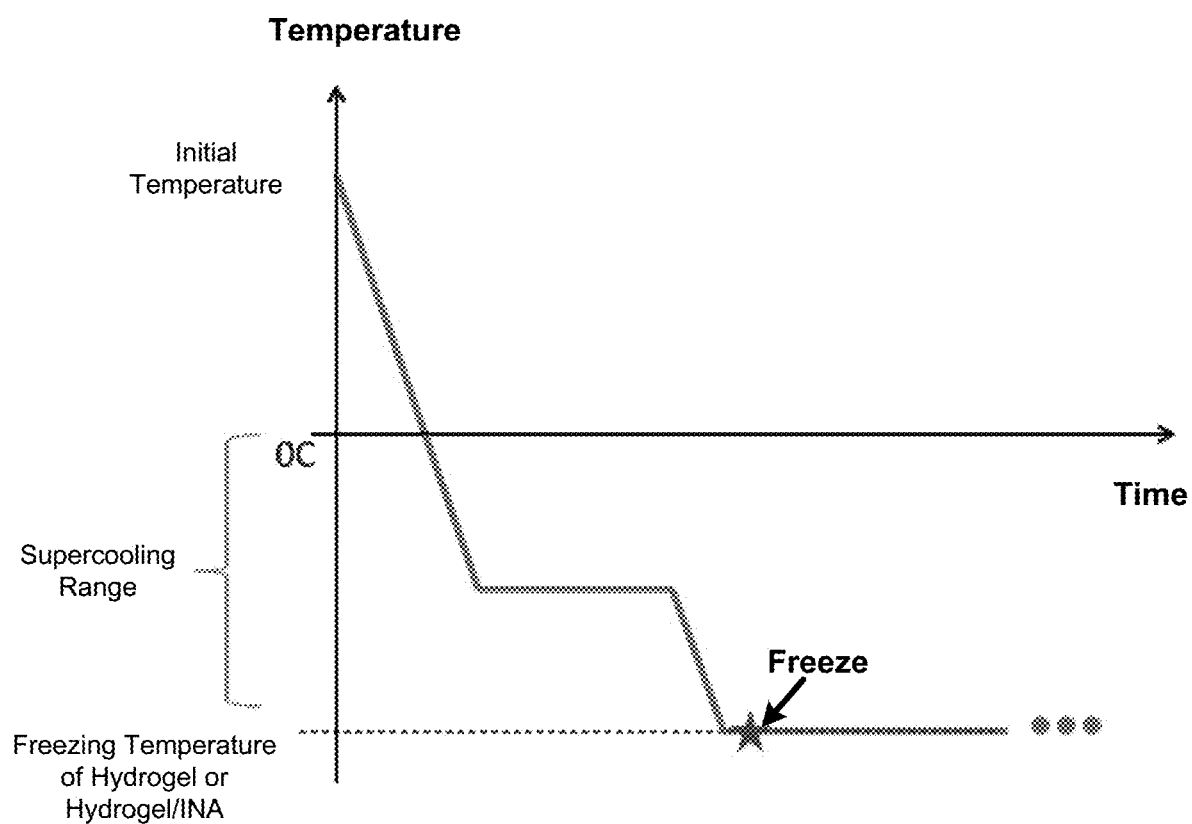
FIG. 35 is a plot of temperature versus time for triggering a freeze agent using a hydrogel.

FIG. 35 is a plot of temperature versus time for triggering a freeze agent in accordance with embodiments of the disclosed technology. The temperature profile, protocol, and/or algorithm for triggering one more freezes allows supercooling of tissue at temperatures allowed by the hydrogel or hydrogel/INA. The temperature of the targeted tissue can be kept in the supercooling temperature range for a supercooling period. The temperature of the hydrogel is then lowered to a freezing temperature to cause ice nucleation of the hydrogel or materials. When it undergoes a freeze event, the underlying targeted tissue can be at or slightly warmer than the hydrogel. In some procedures, both the hydrogel and targeted tissue are supercooled while the temperature of the temperature-controlled surface of the applicator is held generally constant. In other procedures, the targeted tissue can be partially frozen while the hydrogel is supercooled. Subsequent freezing of the hydrogel can cause further freezing of the target tissue until the desired level of freezing in the targeted tissue is achieved. Other coupling media can be used with the temperature profile shown in FIG. 35.

Figure 36:
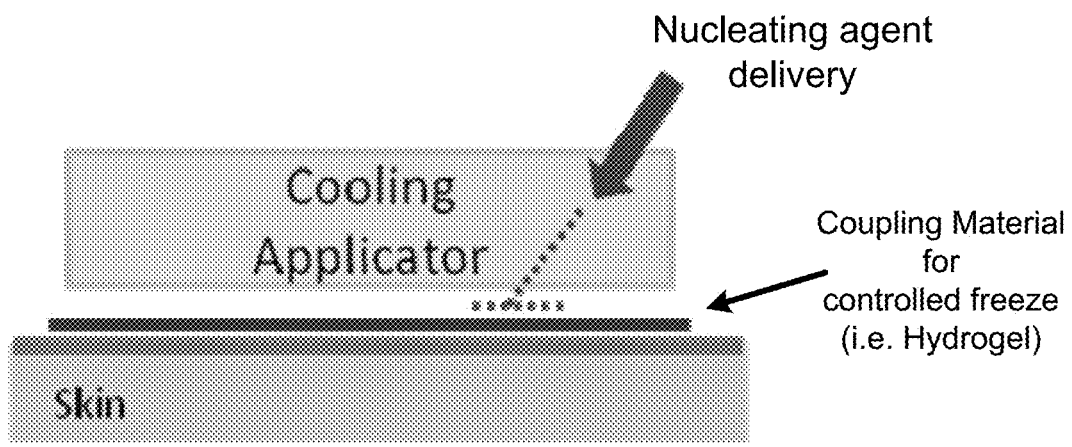
FIG. 36 shows an applicator positioned to produce a controlled freeze in a coupling material in accordance with an embodiment of the disclosed technology.

FIG. 36 shows an applicator positioned to produce a controlled freeze in a coupling media delivering the agent onto a surface of the coupling media, into the coupling media, or at another suitable location for initiating a freeze event in the coupling media. The applicator can include one or more needles (e.g., a microneedle array), fluid components (e.g., conduits, pumps, valves), reservoirs (e.g., reservoirs holding coupling media), or the like. In some embodiments, the agent is delivered out an exit port at the bottom of a cooling plate of the applicator.

Figure 37:
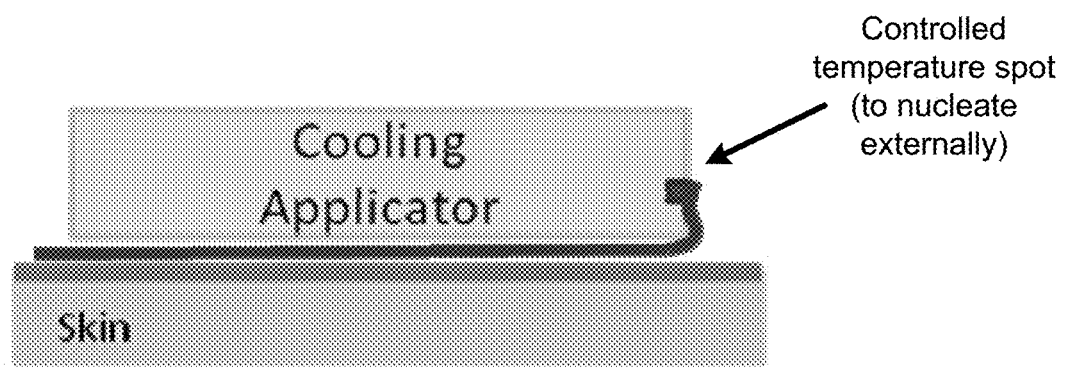
FIG. 37 shows an applicator with an external nucleating element configured to initiate a freeze event at a location external to an applicator-hydrogel interface.

FIG. 37 shows a cooling applicator with an external nucleating element configured to initiate a freeze event external to an applicator-hydrogel interface. The external nucleating element can include one or more energy emitting elements capable of initiating a freeze event. In some embodiments, an external nucleating element delivers energy (e.g., ultrasound energy, RF energy, etc.) to an edge region of the coupling agent to produce a freeze, which propagates through the coupling agent, including a region of the coupling agent directly between the cooling applicator and the tissue site. In other embodiments, a separate nucleating instrument can initiate nucleation and can be a probe with a nucleating element.

Figure 38:
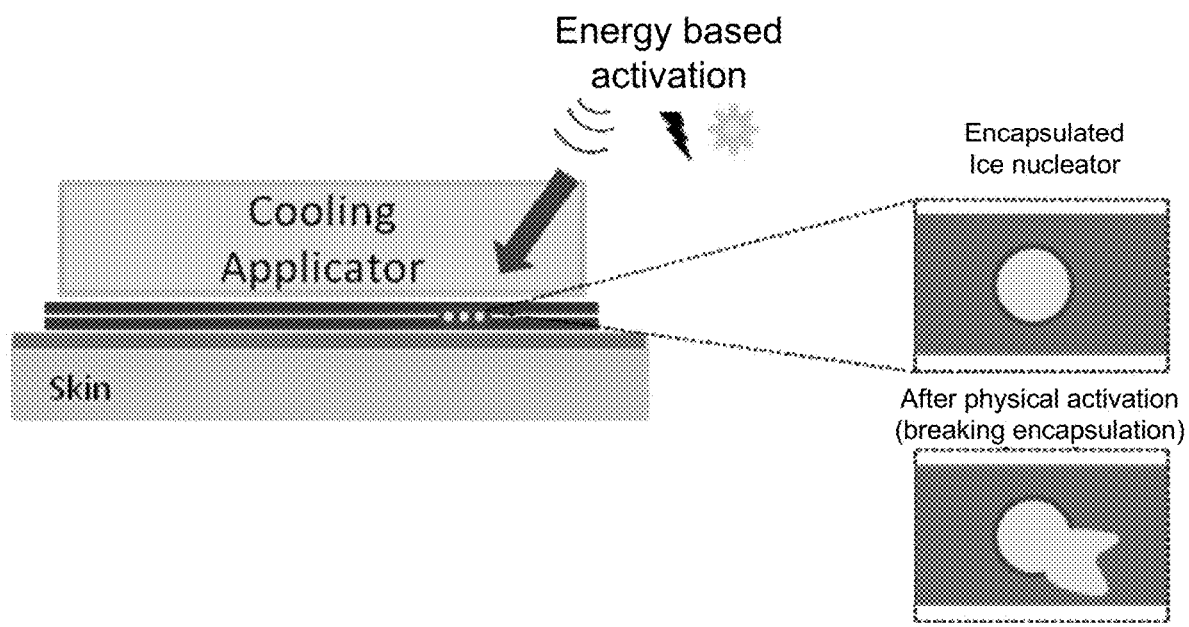
FIG. 38 is a cross-sectional view of an applicator applied to a treatment site and capable of providing energy-based activation.

FIG. 38 is a cross-sectional view of a cooling applicator that provides energy-based activation. Coupling media, hydrogels, hydrogel/INA mixtures, or other materials for generating a controlled freeze can be located between the cooling applicator and the treatment site. In some embodiments, an encapsulated ice nucleator can be part of or located within a layer of coupling media. Energy can break the encapsulation to release the ice nucleator at a desired time. This can cause a freeze event that spreads through the coupling media and into the surface of the skin. Once ice crystals contact the surface of the skin, the freeze can propagate through the skin. The actuation energy can be, without limitation, mechanical energy (e.g., vibrations, ultrasound, etc.), electrical energy, and/or electromagnetic radiation (e.g., light).

Figure 39:
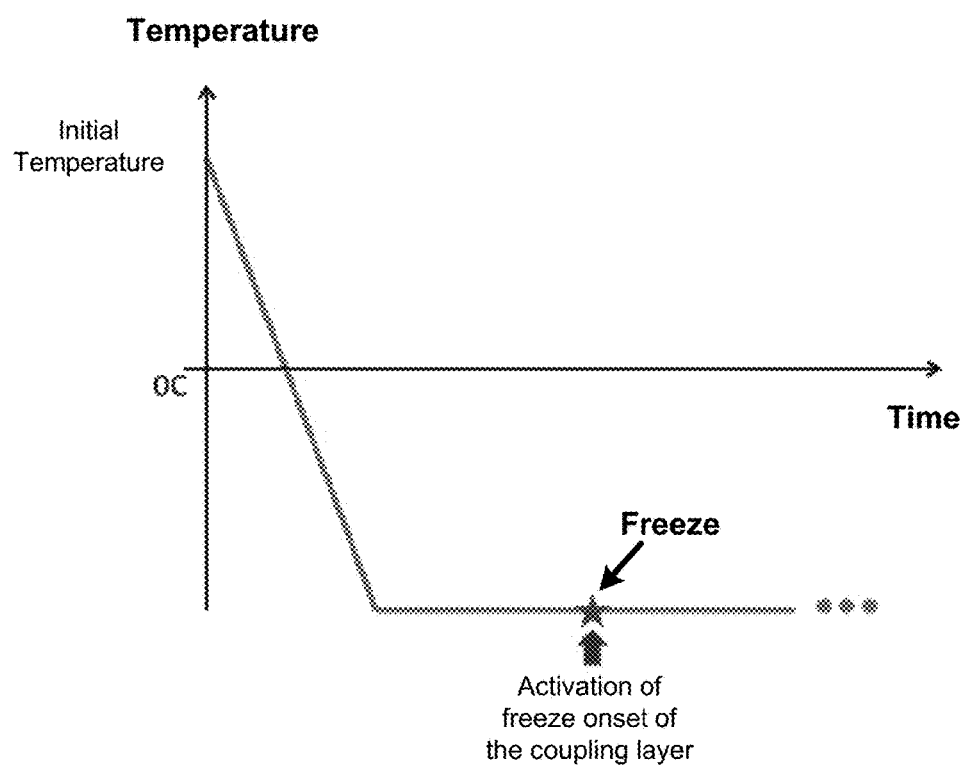
FIG. 39 is a plot of temperature versus time for supercooling skin prior to initiating a freeze event.

FIG. 39 shows a temperature profile for supercooling skin prior to initiating a freeze event. Freeze activation can be controllably initiated to control freeze onset while a temperature-controlled surface of the applicator and/or the target tissue is held at a constant steady state temperature. It may be desirable to supercool and freeze skin and subcutaneous tissue for a specific time and at a specific temperature (or temperature range) to allow controlled supercooling of a tissue volume that is sufficiently large to cause a widespread freeze upon tissue inoculation.

It may be advantageous to cool tissue and/or affect specific structures within the dermis and subcutaneous tissue, like hair, skin appendages, nerves, dermal components such as collagen, elastin, or blood microvascularity but at the same time to preserve the epidermis. Since appendages and other cells/structures may have a different lethal or injury temperature, a multi-step temperature profile may be needed. Moreover, preserving the epidermis could be beneficial in the prevention of skin pigment changes and skin scarring. Additionally, preserving the epidermis can result in more favorable healing and fewer side effects. Freezing the epidermis at a different temperature than the underlying dermis is possible by using the aforementioned techniques. Specifically, the skin bulk tissue can be supercooled at low temperatures and then the temperature of the epidermis can be raised before, for example, delivering the INA or activating nucleation. Epidermal sensitivity is reduced when the epidermis freezes at a temperature of around −5° C. or higher. If freezing below those temperatures occurs, melanocytes and/or their melanin production in the epidermis may get unduly altered causing pigmentation. So, according to some embodiments of the disclosed technology, temperature protocols can be used that cause freezing of the epidermis at or above −5° C.

Figure 40:
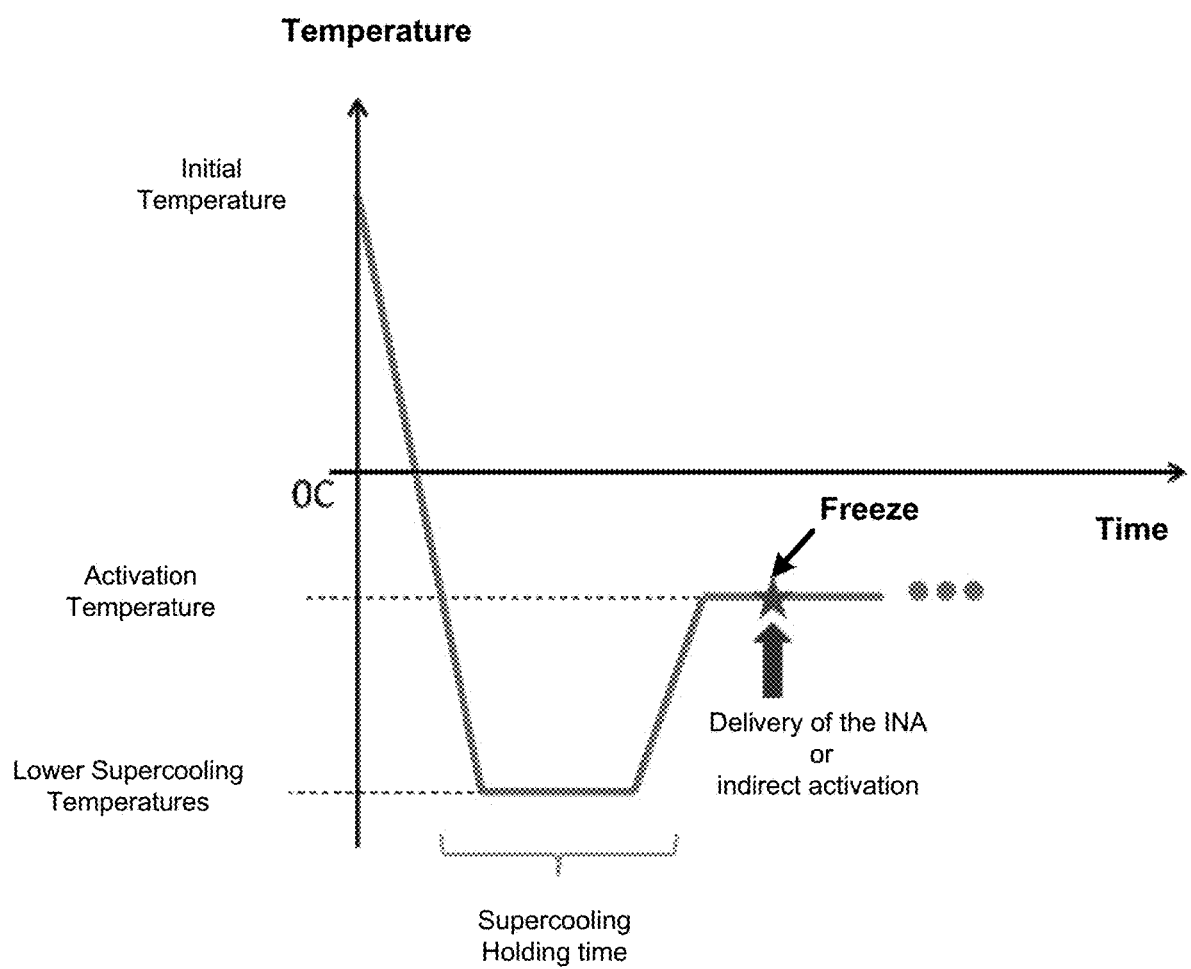
FIG. 40 is a plot of temperature versus time where, after supercooling and before freezing, a temperature of the applicator is adjusted to warm the epidermis.

FIG. 40 is a plot of temperature versus time where, after supercooling and before freezing, a temperature of the applicator is adjusted to warm the epidermis such that the applicator and/or epidermis is at a higher temperature (e.g., −6° C., −5° C., −4° C., etc.) than the supercooling temperature. After warming the epidermis, a freeze event is generated. For example, the temperature profile shows activation or delivery of INAs at a warmer activation temperature suitable for protecting tissue, such as the epidermal or upper layers of the skin. The warming rate, activation temperature, and time period for the activation temperature can be selected based on the desired tissue protection and affects to the targeted tissue. The activation holding time period can be increased or decreased to increase or decrease protection of the epidermis.

Figure 41:
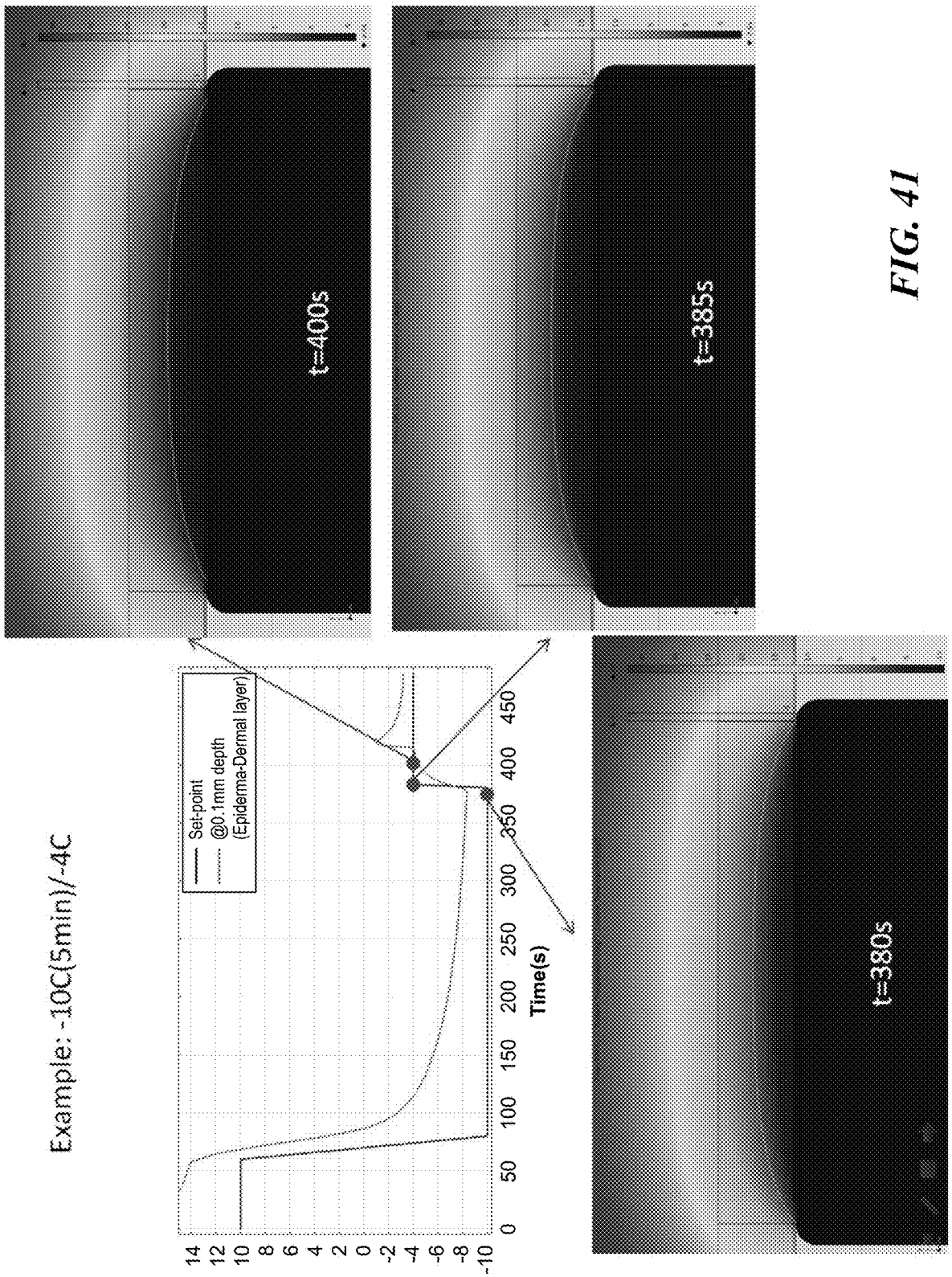
FIG. 41 shows a plot of temperature versus time for a cooling protocol and three cross-sectional views of an applicator and skin tissue and temperature distributions.

FIG. 41 shows a plot of temperature versus time for a cooling protocol and three cross-sectional views of an applicator and skin tissue temperature distributions. As shown in the plot, a temperature-controlled surface of an applicator can be held at −10° C. for 5 minutes (for supercooling) and then increased at a desired rate (e.g., 2° C./s, 2.5° C./s, etc.). A subsequent freeze event is shown by a rise of temperature after about time=400 seconds. Computational modeling (COMSOL) was used to generate the results. The model was a three-dimensional bioheat transfer model for the treatment of skin using a cooling applicator and was used to generate plots discussed herein.

The images show temperature distributions in tissue related to the temperature profile step change of the temperature-controlled surface from −10° C. to −4° C. An isotherm has been added (T=0° C.) at time=380 seconds, time=385 seconds, and time=400 seconds. The isotherm at T=0° C. is the boundary in which phase change to ice crystallization (freezing of skin) may extend the most (i.e., deeper tissue is warmer than 0° C. and will not freeze if ice nucleation were to occur since the fluid in the skin at this depth is above its freezing temperature).

Figure 42:
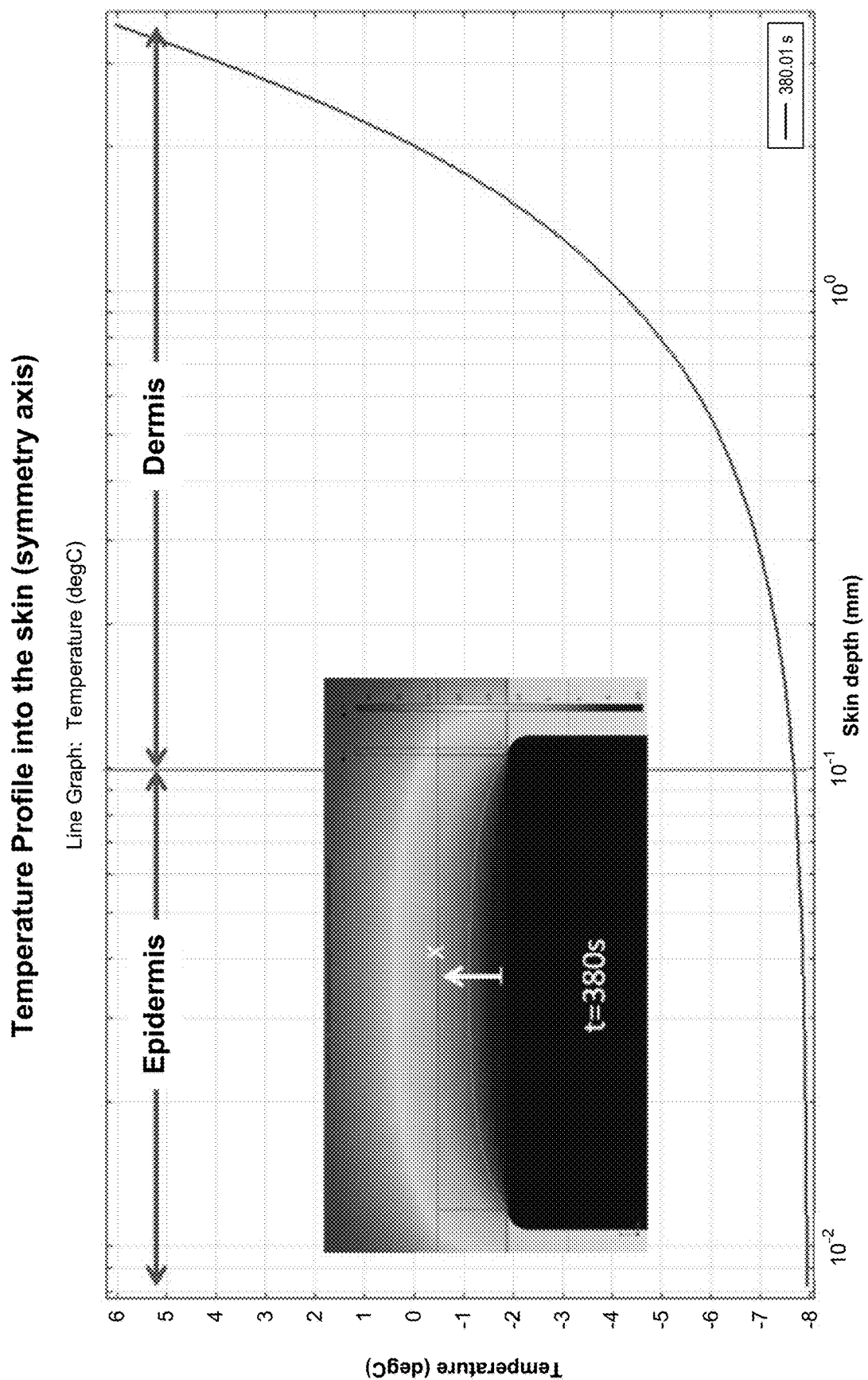
FIG. 42 shows a temperature profile in the epidermis/dermis and temperature distribution for one treatment protocol.

FIG. 42 shows a temperature profile in the epidermis/dermis (log scale) at time=380 seconds for an applicator at −10° C. showing the temperature of T=0° C. at 2 mm depth into the skin. The depth of the T=0° C. isotherm is about 2 mm. Accordingly, the freeze may extend down to about 2 mm into the skin at this time point if nucleation occurred at this time point. The temperature gradient can be observed as well, showing a gradient of T=−8° C. at the skin surface to 0° C. at a depth of 2 mm.

Figure 43:
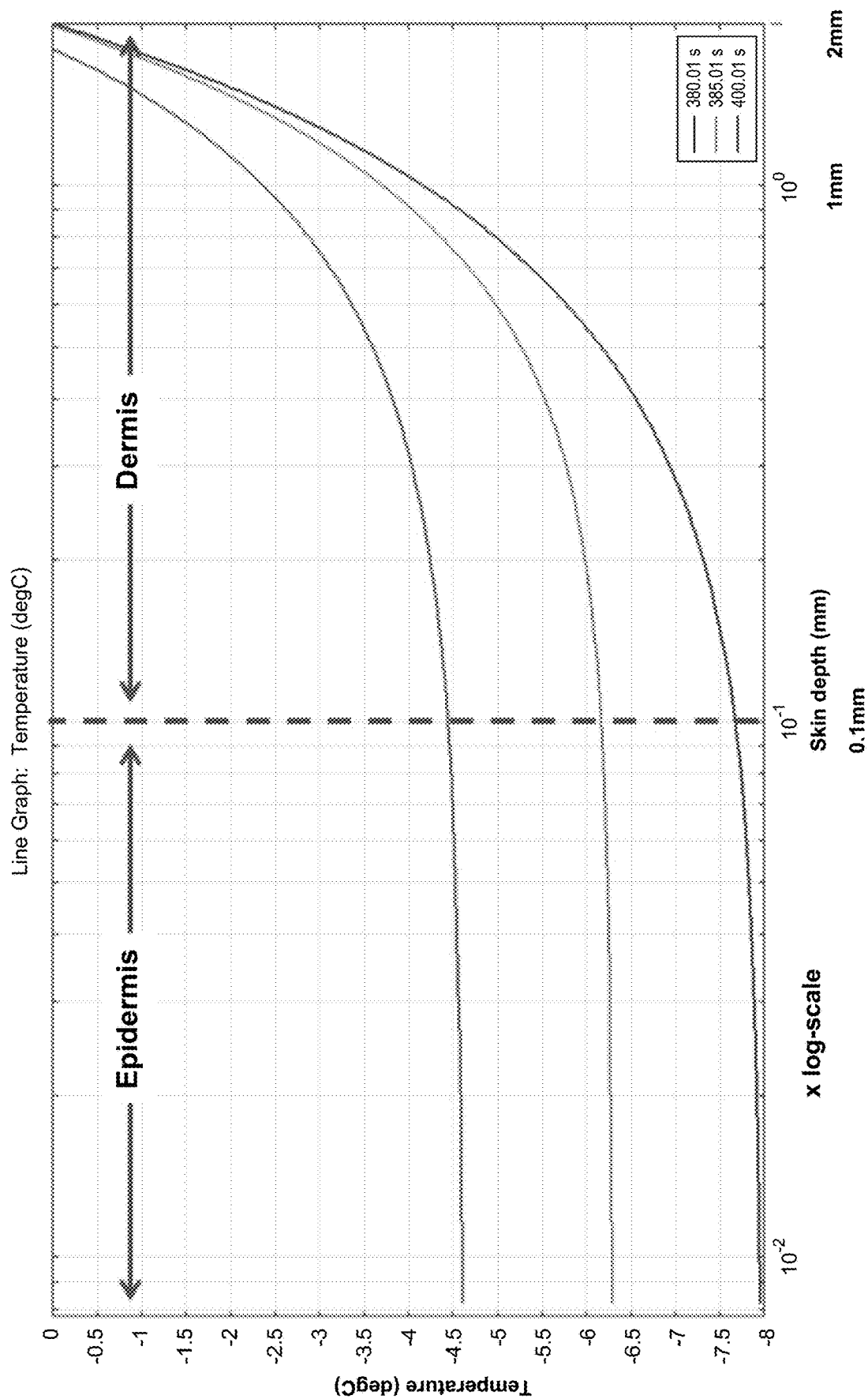
FIG. 43 shows a temperature profile into the epidermis/dermis for one treatment protocol.

FIG. 43 shows a temperature profile in the epidermis/dermis (log scale) showing the temperature as applicator step-ups from −10° C. to −4° C. at 2.5° C./s, with lines plotted for time=380 seconds, time=385 seconds, and time=400 seconds. The temperature profiles throughout the depth of the skin at time=380, time=385, and time=400 seconds, in other words, are both before and after the applicator temperature has transitioned from −10° C. to −4° C. Temperature gradients in the epidermis are above −5° C. at time=400 seconds so that a controlled freeze may be triggered. The epidermis will freeze at a more optimal temperature (>−5° C.) but with a superior extent of the skin freeze down to a depth of approximately 2 mm.

Figure 44:
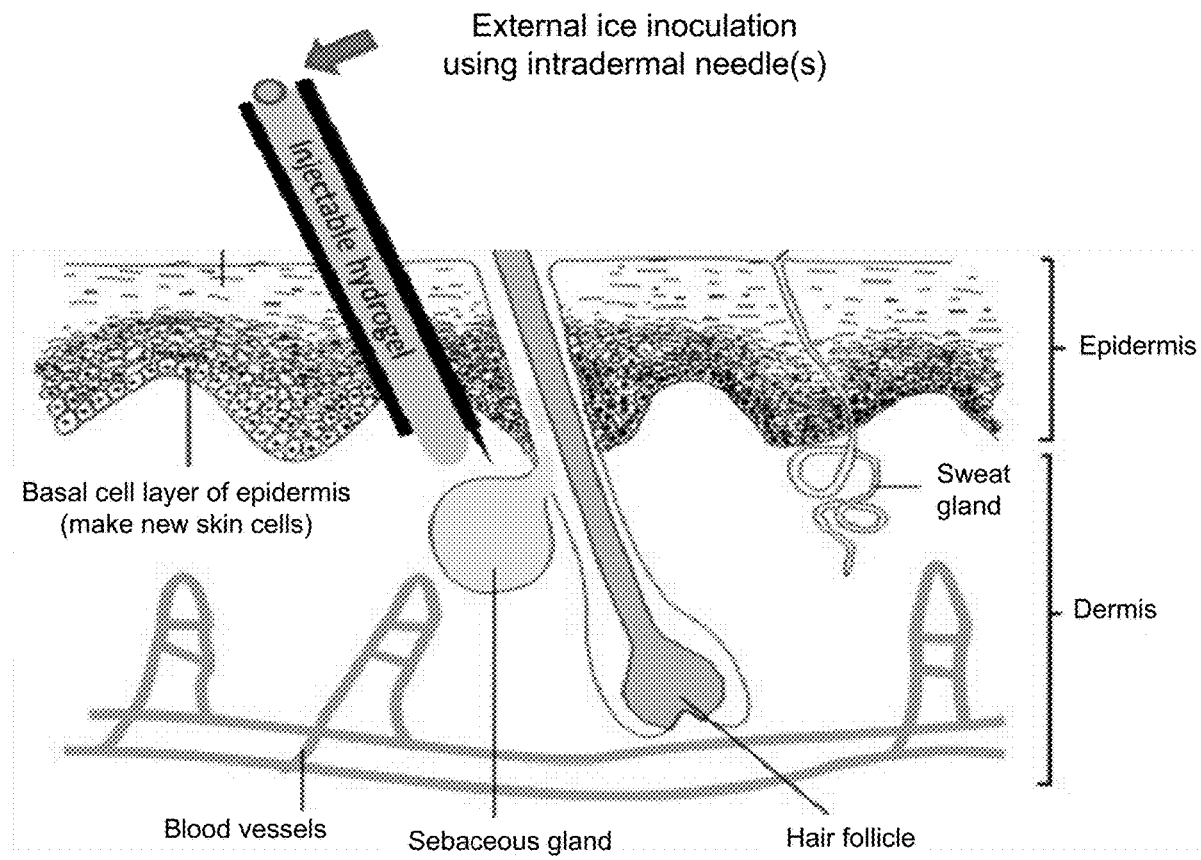
FIG. 44 shows a stage in one method of creating an intradermal tissue freeze using an injectable substance.

FIG. 44 shows one method of creating a tissue freeze using a device positioned within a subject. The device can be a needle that injects a substance at a specific location. An interior surface of the needle can be coated to facilitate delivery of the substance. The exterior surface of the needle can be coated with an agent or substance for treating tissue, targeted structures, etc. Other devices can be inserted into the subject to produce freeze events.

The injected substance can include, without limitation, hydrogel, hydrogel/INA, partially frozen water, ice nucleators, combinations thereof, or the like. An advantage of injecting an ice crystal or substance (e.g., an INA) that will create an ice crystal is that a freeze event will occur at a specific region. The freeze event can be initiated in the dermis or other lower tissue layer and not in the epidermis. This limits or minimizes damage to the epidermis. Additionally, the epidermis can be warmed to a temperature close to or above its melting/freeze temperature. In some embodiments, a freeze event can be initiated in tissue below the dermis, such as in subcutaneous tissue. After producing the freeze event, the same or different needle can inject additional substances into the tissue. The additional substances can include cryoprotective agents, liquids (e.g., warm water or saline), or other substances that can effect therapy.

Multiple injections can be made to create multiple freeze events. A first substance can be delivered into tissue to create a first freeze event, and a second substance can be delivered into other tissue to produce a second freeze event. For example, the first substance can be adapted to completely freeze at a first target region, and the second substance can be adapted to produce a partial freeze event at a second target region spaced apart from the first target region. Different levels of freezing and severity of thermal injury can be achieved even though the first and second target regions are at the same temperature. In other treatments, the first and second target regions can be at different temperatures, and the first and second substances can be selected based on those temperatures. In this manner, different types of freeze events can be generated at different locations.

With continued reference to FIG. 44, substances with thermal coupling materials or nucleators having freezing points at higher temperatures than a freezing point of fluid in skin tissue may be used synergistically with the treatment cycle to produce an intentional freeze of the material and sequentially trigger freezing propagation into the skin at yet higher temperatures. Non-targeted tissue can be warmed by the applicator (e.g., via conduction), injected warm liquid, and/or energy (e.g., RF energy). Warming cycles can be performed to warm the epidermis immediately after producing a freeze event that injures target structures, such as sebaceous gland. This can help prevent visible alterations (e.g., hyperpigmentation, hypopigmentation, etc.) to the epidermis. The injectable substance can be delivered to and around the sebaceous gland and freeze event can then be triggered by a temperature dive, dilution, energy, etc.

Figure 45:
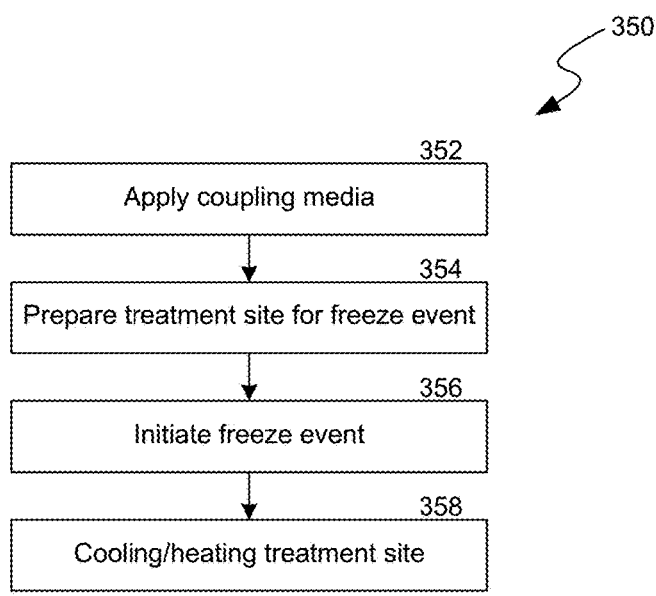
FIG. 45 is a flow diagram illustrating a method for preparing and freezing tissue in accordance with an aspect of the present technology.

FIG. 45 is a flow diagram illustrating a method 350 in accordance with an aspect of the present technology. In block 352, coupling media can be applied to the subject. In block 354, an applicator cools the tissue to a temperature suitable for a freeze event. For example, a skin surface can be lowered to a first temperature between about −2° C. and −40° C. to supercool shallow tissue. In some embodiments, the first temperature can be a temperature between −5° C. and −15° C., −5° C. and −20° C., −10° C. and −30° C., or other suitable temperature range below a freezing temperature.

In block 356, the surface of the human subject's skin is heated an amount sufficient to raise the skin surface temperature from the first temperature to a second temperature, which can be a non-supercooled temperature, while the targeted region remains in the supercooled state. For example, the epidermis can be heated to a temperature higher than about 0° C., higher than about 5° C., higher than about 10° C., higher than about 20° C., higher than about 30° C., or higher than about 35° C. There can be a temperature gradient between the targeted tissue and the skin surface such that most of the non-targeted shallow tissue is at a non-supercooled temperature.

In block 356, the device of FIG. 44 can cause nucleation at the target region to cause at least some fluid and cells in the supercooled tissue to at least partially or totally freeze. Warmed cells residing at the surface of the human subject's skin do not freeze. As such, cells at the skin surface can be protected without using a chemical cryoprotectant. However, chemical cryoprotectants can be used to inhibit or limit hyperpigmentation or hypopigmentation. In some embodiments, a probe can be inserted into the subject to cause nucleation of the supercooled tissue via a mechanical perturbation, ultrasound, or other suitable nucleation initiator. The freeze event can cause at least partial crystallization of a plurality of gland cells in the target region. The illustrated device of FIG. 44 is positioned to produce a freeze event that causes crystallization of cells in the sebaceous gland.

In block 358 of FIG. 45, the supercooled tissue can be maintained in the frozen state for a predetermined period of time longer than, for example, about 10 seconds, 12 seconds, 15 seconds, 20 seconds, or other suitable length of time sufficient to treat acne, improve a quality of hair, treat hyperhidrosis, etc. In certain embodiments, the skin is cooled/heated to keep the targeted tissue in at least a partially or totally frozen state for the predetermined time longer than about 10 seconds, 12 seconds, 15 seconds, or 20 seconds.

Heat can be applied to warm epidermal cells to a temperature above freezing while glands in the dermis are at or near the supercooled temperature. The step of applying heat can include warming a portion of most of the epidermal layer under the treatment device to a temperature above about 0° C., about 5° C., about 10° C., about 20° C., about 25° C., or about 32° C. Warming can be accomplished before, during, or after the freeze event. The subject's body heat, warm blood, or other mechanisms can naturally heat the epidermis to avoid or limit freeze damage to those cells.

If deeper tissue is not targeted, such tissue could be warmed using focused electrical currents, such as focused ultrasound or RF energy. Applicators can include one or more electrodes, transducers, or other energy-emitting elements. For example, an applicator can cool the skin surface shown in FIG. 44 to supercool the tissue, including the dermis. The applicator can deliver RF energy or focused electrical currents to the underlying non-targeted subcutaneous tissue to localize supercooling to dermal tissue. A freeze event is then initiated in the supercooled dermal tissue.

The methods disclosed herein are capable of supercooling tissue without initiating nucleation by cooling tissue at a relatively slow rate (e.g., the temperature profile can cause a slow cooling of the tissue at the target region). For example, the rate of cooling can be either equal to, slower or faster than about 0.5° C., 1° C., 2° C., 3° C., 4° C., 5° C., 6° C., 7° C., 8° C., 9° C. or 10° C. per minute. A preferred rate of cooling is about either 2° C., 4° C., or 6° C. per minute. Additionally or alternatively, a treatment device can apply a generally constant pressure during cooling to the supercooled temperature range to avoid pressure changes that would cause inadvertent nucleation. In a further embodiment, the targeted tissue can be cooled while the patient is held still (e.g., without movement of the treatment site) to avoid mechanically disturbing the supercooled tissue and unintentionally causing crystallization.

F. Suitable Computing Environments

Figure 46:
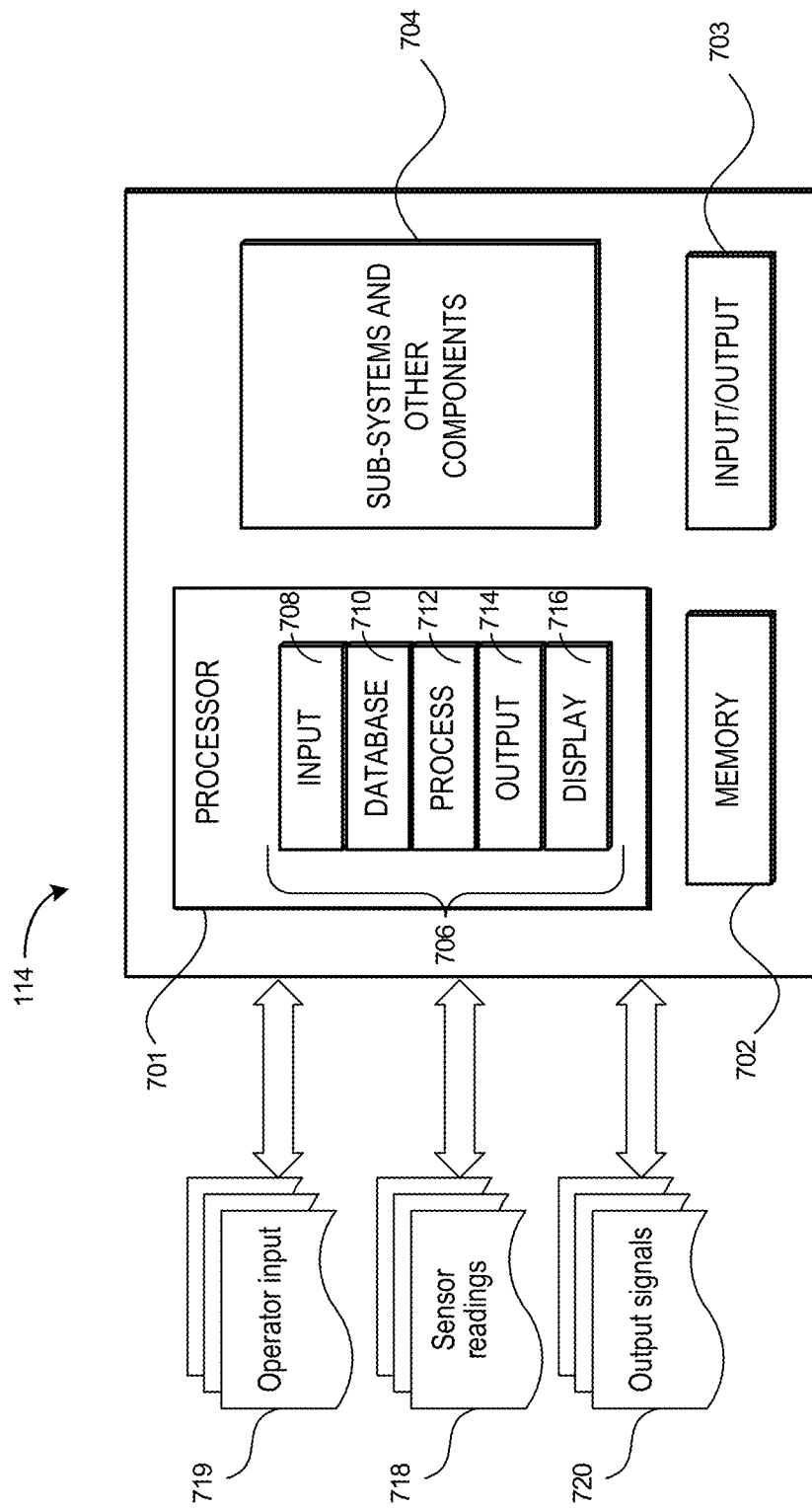
FIG. 46 is a schematic block diagram illustrating subcomponents of a computing device in accordance with an embodiment of the disclosure.

FIG. 46 is a schematic block diagram illustrating subcomponents of a computing device in the form of a controller suitable for the system 100 of FIG. 3 in accordance with an embodiment of the disclosure. The computing device 700 can include a processor 701, a memory 702 (e.g., SRAM, DRAM, flash, or other memory devices), input/output devices 703, and/or subsystems and other components 704. The computing device 700 can perform any of a wide variety of computing processing, storage, sensing, imaging, and/or other functions. Components of the computing device 700 may be housed in a single unit or distributed over multiple, interconnected units (e.g., through a communications network). The components of the computing device 700 can accordingly include local and/or remote memory storage devices and any of a wide variety of computer-readable media.

As illustrated in FIG. 46, the processor 701 can include a plurality of functional modules 706, such as software modules, for execution by the processor 701. The various implementations of source code (i.e., in a conventional programming language) can be stored on a computer-readable storage medium or can be embodied on a transmission medium in a carrier wave. The modules 706 of the processor can include an input module 708, a database module 710, a process module 712, an output module 714, and, optionally, a display module 716.

In operation, the input module 708 accepts an operator input 719 via the one or more input/output devices described above with respect to FIG. 3, and communicates the accepted information or selections to other components for further processing. The database module 710 organizes records, including patient records, treatment data sets, treatment profiles and operating records and other operator activities, and facilitates storing and retrieving of these records to and from a data storage device (e.g., internal memory 702, an external database, etc.). Any type of database organization can be utilized, including a flat file system, hierarchical database, relational database, distributed database, etc.

In the illustrated example, the process module 712 can generate control variables based on sensor readings 718 from sensors (e.g., sensor 167 of FIG. 2) and/or other data sources, and the output module 714 can communicate operator input to external computing devices and control variables to the controller 114 (FIG. 3). The output signals 720 can be used to control one or more applicators applied to the patient. In some embodiments, the output signals 720 can be commands for controlling applicators. The display module 816 can be configured to convert and transmit processing parameters, sensor readings 818, output signals 720, input data, treatment profiles, and prescribed operational parameters through one or more connected display devices, such as a display screen, printer, speaker system, etc. A suitable display module 716 may include a video driver that enables the controller 114 to display the sensor readings 718 or other status of treatment progression.

In various embodiments, the processor 701 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 702 can be standard memory, secure memory, or a combination of both memory types. By employing a secure processor and/or secure memory, the system can ensure that data and instructions are both highly secure and sensitive operations such as decryption are shielded from observation. The memory 702 can contain executable instructions for cooling the surface of the subject's skin to a temperature and controlling treatment devices in response to, for example, detection of supercooling, a partial or complete freeze event, movement of the applicator (e.g., applicator pull off), or the like. In some embodiments, the memory 702 can include nucleation instructions that, when executed, cause the controller to command an applicator to alter the composition of a coupling media, inject nucleation initiator, etc. Additionally or alternatively, the memory 702 can include thawing instructions that, when executed, causes the controller to control the applicator to heat tissue. In some embodiments, the stored instructions can be executed to control the applicators to perform the methods disclosed herein without causing undesired effects, such as significantly lightening or darkening skin one of more days after the freeze event ends. The instructions can be modified based on patient information and treatments to be performed. Other instructions and algorithms (including feedback control algorithms) can be stored and executed to perform the methods disclosed herein.

In some embodiments, the controller 114 is programmed to cause the applicator to create or maintain at least one ice crystal and to induce a freeze event. The memory 702, for example, can contain instructions that when executed cause the applicator to operate to cause one or more ice crystals to contact the subject skin so as to induce a freeze event. In one embodiment, the memory 702 contains instructions that when executed by the processor 701 cause the applicator to be a suitable temperature for supercooling target tissue and for freezing the skin without lowering a temperature of the temperature-controlled surface below a particular level. The instructions can be used to control or communicate with components of applicators. These components can include, without limitation, one or more thermoelectric elements, fluid elements, energy-emitting elements, and sensors. The thermoelectric elements can be Peltier devices capable of selectively cooling or heating the tissue. The fluid elements can be cooling channels, conduits, or other fluid elements through which fluid can flow to heat and/or cool tissue. The energy emitting elements can be radiofrequency electrodes, ultrasound electrodes, or other elements capable of delivering energy to control freezing, warm tissue, or the like.

Suitable computing environments and other computing devices and user interfaces are described in commonly assigned U.S. Pat. No. 8,275,442, titled "TREATMENT PLANNING SYSTEMS AND METHODS FOR BODY CONTOURING APPLICATIONS," which is incorporated herein in its entirety by reference.

G. Conclusion

The treatment systems, applicators, and methods of treatment can be used to treat acne, hyperhidrosis, wrinkles, subcutaneous tissue, structures (e.g., structures in the epidermis, dermis, subcutaneous fat, muscle, nerve tissue, etc.), and so on. Methods for cooling tissue and related devices and systems in accordance with embodiments of the present invention can at least partially address one or more problems associated with conventional technologies as discussed above and/or other problems whether or not such problems are stated herein. Methods for affecting skin of a human subject's body include positioning an applicator of a cooling apparatus on the subject and removing heat from a treatment site to affect the appearance of the subject's skin with or without causing an appreciable reduction of subcutaneous adipose tissue. Acne along the face can be treated without causing any reduction of subcutaneous adipose tissue wherein acne along the back can be treated while reducing of subcutaneous adipose tissue. Systems, components, and techniques for reducing subcutaneous adipose tissue are disclosed in U.S. Pat. No. 7,367,341 titled "METHODS AND DEVICES FOR SELECTIVE DISRUPTION OF FATTY TISSUE BY CONTROLLED COOLING" to Anderson et al., U.S. Patent Publication No. US 2005/0251120 titled "METHODS AND DEVICES FOR DETECTION AND CONTROL OF SELECTIVE DISRUPTION OF FATTY TISSUE BY CONTROLLED COOLING" to Anderson et al., and U.S. Patent Publication No. 2007/0255362 titled "CRYOPROTECTANT FOR USE WITH A TREATMENT DEVICE FOR IMPROVED COOLING OF SUBCUTANEOUS LIPID-RICH CELLS," the disclosures of which are incorporated herein by reference in their entireties. For example, sufficient amount of thermal energy can be removed from the site so as to reduce wrinkles by, for example, reducing the number of visible wrinkles and/or sizes of the wrinkles. In other embodiments, a sufficient amount of thermal energy is removed from the treatment site so as to tighten skin at the treatment site, or in further embodiments, to alter the tissue between a surface of the skin and subcutaneous lipid-rich cells of the subject's body. In a further embodiment, tissue is cooled to induce fibrosis that increases the firmness of tissue at the treatment site. Fibrosis can be induced in the epidermis, dermis, and/or subcutaneous tissue. Vacuum applicators can stretch, stress, and/or mechanically alter skin to increase damage and fibrosis in the skin, affect glands, control freeze events (including initiating freeze events), etc.

It will be appreciated that some well-known structures or functions may not be shown or described in detail so as to avoid unnecessarily obscuring the relevant description of the various embodiments. Although some embodiments may be within the scope of the technology, they may not be described in detail with respect to the figures. Furthermore, features, structures, or characteristics of various embodiments may be combined in any suitable manner. The technology disclosed herein can be used for improving skin and skin conditions and to perform the procedures disclosed in U.S. Provisional Application Ser. No. 61/943,250, filed Feb. 21, 2014, U.S. Pat. No. 7,367,341 entitled "METHODS AND DEVICES FOR SELECTIVE DISRUPTION OF FATTY TISSUE BY CONTROLLED COOLING" to Anderson et al., and U.S. Patent Publication No. US 2005/0251120 entitled "METHODS AND DEVICES FOR DETECTION AND CONTROL OF SELECTIVE DISRUPTION OF FATTY TISSUE BY CONTROLLED COOLING" to Anderson et al., the disclosures of which are incorporated herein by reference in their entireties. The technology disclosed herein can target tissue for tightening the skin, improving skin tone or texture, eliminating or reducing wrinkles, or increasing skin smoothness as disclosed in U.S. Provisional Application Ser. No. 61/943,250.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. In those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.).

Any patents, applications and other references, including any that may be listed in accompanying filing papers, are incorporated herein by reference. Aspects of the described technology can be modified, if necessary, to employ the systems, functions, and concepts of the various references described above to provide yet further embodiments. While the above description details certain embodiments and describes the best mode contemplated, no matter how detailed, various changes can be made. Implementation details may vary considerably, while still being encompassed by the technology disclosed herein. The various aspects and embodiments disclosed herein are for purposes of illustration and are not intended to be limiting, with the true scope and spirit being indicated by the following claims.

What is claimed is:

1. A method for treating a subject's skin, comprising:
applying a coupling media to the skin, wherein the coupling media includes an ice nucleation agent, a freezing point depressant, and either a liposome, an oil-in-water emulsion, a water-in-oil emulsion, or an oil-in-oil emulsion containing the freezing point depressant to enhance delivery of the freezing point depressant to the skin; and
cooling the coupling media and a surface of the skin with an applicator to a temperature below 0° C. to treat the skin.

2. The method of claim 1, wherein the freezing point depressant comprises propylene glycol, glycerol, and/or polyethylene glycol.

3. The method of claim 1, wherein the coupling media includes the liposome, and wherein the liposome and freezing point depressant is a propylene glycol liposome.

4. The method of claim 1, wherein the coupling media includes the liposome, and wherein the liposome further comprises water such that the freezing point depressant and the water are released into the skin after the liposome breaks down.

5. The method of claim 1, wherein the coupling media includes the liposome, wherein the method further comprises
breaking a lipid encapsulation of the liposome using ultrasound energy, temperature cycling, and/or a cleansing agent to release the freezing point depressant.

6. The method of claim 1, further comprising controlling cooling of the coupling media and the skin surface so as not to freeze the epidermis.

7. The method of claim 1, further comprising controlling cooling of the coupling media and the surface cooling so as to freeze the skin.

8. The method of claim 1, wherein the coupling media is either the oil-in-water emulsion or the water-in-oil emulsion.

9. The method of claim 8, wherein the oil-in-water emulsion or the water-in-oil emulsion is a nanoemulsion.

10. A method for treating a subject's skin, comprising:
applying a coupling media to the skin, wherein the coupling media includes an ice nucleation agent, a freezing point depressant, and either a liposome, an oil-in-water emulsion, a water-in-oil emulsion, or an oil-in-oil emulsion containing the freezing point depressant to enhance delivery of the freezing point depressant to the skin;

cooling the coupling media and a surface of the skin with an applicator to a temperature below 0° C. to treat the skin; and controlling cooling of the coupling media and the surface of the skin to predictably freeze the skin based on nucleation caused by the ice nucleation agent.

11. A method for treating a subject's skin, comprising:

applying a coupling media to a surface of the subject's skin such that an ice nucleating agent contained in the applied coupling media does not directly contact epidermal cells for a period of time;

applying an applicator to the subject's skin; and cooling the coupling media and the surface of the skin with the applicator to lower a temperature of the surface of the skin below 0° C. to cause a freeze event initiated by the ice nucleating agent so as to freeze the skin.

12. The method of claim 11, wherein cooling the coupling media and the surface of the skin include removing heat from the skin to start freezing the skin after the period of time.

13. The method of claim 11, wherein the coupling media comprises a liposome, an oil-in-water emulsion, a water-in-oil emulsion, an oil-in-oil emulsion, and/or nano-emulsion.

14. The method of claim 11, wherein the coupling media includes a freezing point depressant for lowering a freezing point of the skin.

15. The method of claim 14, wherein the freezing point depressant is configured to penetrate the skin only a shallow depth to lower a freezing point of epidermal tissue more than dermal tissue.

16. The method of claim 11, further comprising breaking apart a liposome of the coupling media to release the ice nucleating agent for initiating the freeze event.

17. The method of claim 11, wherein cooling the coupling media and the surface of the skin includes:

removing heat from the skin to supercool targeted tissue in the skin;

freezing the targeted tissue; and after freezing the targeted tissue, removing heat from and/or applying heat to the skin to keep an epidermal layer frozen while a dermal layer thaws and refreezes.

18. The method of claim 11, further comprising either:

diluting the coupling media to raise its freezing point to produce the freeze event, and/or delivering energy to activate the ice nucleating agent, and/or reducing the temperature of the coupling media to cause the freeze event after a fluid in the subject's skin has been cooled below its freezing point.

19. A system for treating a subject, comprising:

an applicator configured to reduce a temperature of a target region beneath a surface of the subject's skin to reduce the temperature of target tissue from a natural body temperature to a temperature for freezing the target tissue;

a coupling media including an ice nucleating agent, a freezing point depressant and either a liposome, an oil-in-water emulsion, a water-in-oil emulsion, or oil-in-oil emulsion containing the freezing point depressant to enhance delivery of the freezing point depressant to the skin; and a controller programmed to cause the applicator to cool the coupling media and a surface of the skin to a temperature below 0° C. to freeze the skin for a period of time.

* * * * *